US011104700B2

(12) United States Patent
Brown et al.

(10) Patent No.: US 11,104,700 B2
(45) Date of Patent: *Aug. 31, 2021

(54) OLIGONUCLEOTIDES

(71) Applicant: OXFORD UNIVERSITY INNOVATION LIMITED, Botley (GB)

(72) Inventors: Tom Brown, Oxford (GB); Afaf Helmy El-Sagheer, Oxford (GB); Pawan Kumar, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 56 days.

This patent is subject to a terminal disclaimer.

(21) Appl. No.: 16/037,155

(22) Filed: Jul. 17, 2018

(65) Prior Publication Data

US 2019/0023732 A1    Jan. 24, 2019

Related U.S. Application Data

(60) Provisional application No. 62/533,273, filed on Jul. 17, 2017.

(51) Int. Cl.
| | |
|---|---|
| *C07H 21/04* | (2006.01) |
| *C12N 15/11* | (2006.01) |
| *C07H 21/02* | (2006.01) |
| *C12Q 1/6844* | (2018.01) |

(52) U.S. Cl.
CPC ............. *C07H 21/04* (2013.01); *C07H 21/02* (2013.01); *C12N 15/11* (2013.01); *C12N 15/111* (2013.01); *C12Q 1/6844* (2013.01); *C12N 2310/11* (2013.01); *C12N 2310/141* (2013.01); *C12N 2310/313* (2013.01); *C12N 2310/314* (2013.01); *C12N 2310/315* (2013.01); *C12N 2310/317* (2013.01); *C12N 2310/318* (2013.01); *C12N 2310/3125* (2013.01); *C12N 2310/3231* (2013.01); *C12N 2310/332* (2013.01); *C12N 2310/3341* (2013.01)

(58) Field of Classification Search
CPC ...... C07H 21/04; C07H 21/02; C12Q 1/6844; C12Q 2525/113; C12N 15/11; C12N 15/111; C12N 2310/3341; C12N 2310/141; C12N 2310/314; C12N 2310/315; C12N 2310/317; C12N 2310/3125; C12N 2310/332; C12N 2310/11; C12N 2310/318; C12N 2310/3231; C12C 1/6844; C12C 2525/113

See application file for complete search history.

(56) References Cited

U.S. PATENT DOCUMENTS

| | | | |
|---|---|---|---|
| 8,846,883 | B2 | 9/2014 | Brown |
| 10,604,755 | B2 | 3/2020 | Collard et al. |
| 10,633,656 | B2 | 4/2020 | Tuschl et al. |
| 10,669,577 | B2 | 6/2020 | Ju et al. |
| 10,683,321 | B2 | 6/2020 | Dukhan et al. |
| 10,844,430 | B2 | 11/2020 | Andruzzi et al. |
| 2019/0015439 | A1* | 1/2019 | Brown ............... A61K 31/7084 |

OTHER PUBLICATIONS

"Products for DNA research," created by Glen Research, LLC, 2020 Catalog, (2020) pp. 1-176.
Makarova et al., "An updated evolutionary classification of CRISPR-Cas systems," Nat Rev Microbiology, Sep. 28, 2015, 13:722-736.
Makarova et al., "Unification of Cas protein families and a simple scenario for the origin and evolution of CRISPR-Cas systems," Biol Direct., 2011, 6:38.
Barrangou, "Diversity of CRISPR-Cas immune systems and molecular machines," Genome Biology, 2015, 16:247.
Rueda et al., "Mapping the sugar dependency for rational generation of a DNA-RNA hybrid-guided Cas9 endonuclease," Nature Communications, 2017, 8:1610.
Gagnon and Corey, "Stepping toward therapeutic CRISPR," Proc. Natl. Acad. Sci., Dec. 22, 2015, 12:15536-15537, USA.
Rahdar et al., "Synthetic CRISPR RNA-Cas9-guided genome editing in human cells," Proc. Natl. Acad. Sci., Nov. 16, 2015, 112:E7110-71 17, USA.
Liang et al., "Rapid and highly efficient mammalian cell engineering via Cas9 protein transfection," J. Biotechnol., 2015, 208:44-53.
Zuris et al., "Cationic lipid-mediated delivery of proteins enables efficient protein-based genome editing in viro and in vivo," Nat. Biotechnot, Jan. 2015, 33:73-80.
Yu et al., "Improved delivery of Cas9 protein/gRNA complexes using lipofectamine CRISPRMAX," Biotechnol. Lett., Feb. 18, 2016, 38:919-929.

(Continued)

*Primary Examiner* — Lawrence E Crane
(74) *Attorney, Agent, or Firm* — Barnes & Thornburg LLP

(57) ABSTRACT

The present invention relates to novel oligonucleotides comprising at least one locked nucleoside and at least one triazole inter-nucleoside linkage linkage of Formula A or Formula B Formula A Formula B and methods of making the same.

22 Claims, 25 Drawing Sheets

Specification includes a Sequence Listing.

(56) References Cited

OTHER PUBLICATIONS

El-Sagheer and Brown, Chem Soc Rev, Feb. 2010, 39:1388-1405.
Fujino et al., "Chimeric RNA oligonucleotides incorporating triazole-linked trinucleotides: synthesis and function as mRNA in cell-free translation reactions," J Org Chem, 2016, 81:8967-8976.
Fujino et al., "Chimeric RNA oligonucleotides with triazole and phosphate linkages: synthesis and RNA interference," Chem Asian J, 2015, 10: 2683-2688.
Isobe and Fujino, "Triazole-linked analogues of DNA and RNA synthesis and function," Chem Rec, 2014, 14:41-51.
Varizhuk et al., "Synthesis of triazole-linked oligonucleotides with high affinity to DNA complements and an analysis of their compatibility with biosystems," J Org Chem, Jun. 3, 2013, 78:5964-5969.
Varizhuk et al., "Synthesis, characterization and in vitro activity of thrombin-binding DNA aptamers with triazole internucleotide linkages," Eur J Med Chem, Jun. 25, 2013, 67:90-97.
El-Sagheer and Brown, "Click nucleic acid ligation: applications in biology and nanotechnology," Acc Chem Res, 2012, 45:1258-1267.
El-Sagheer et al., "Biocompatible artificial DNA linker that is read through by DNA polymerases and is functional in *Escherichia coli*," Proc Natl Acad Sci, Jul. 12, 2011, 108(28):11338-11343.
El-Sagheer and Brown, "Efficient RNA synthesis by in vitro transcription of a triazole-modified DNA template," Chemical Commun, Nov. 28, 2011, 47(44):12057-12058.
Birts et al., "Transcription of click linked DNA in human cells," Angew Chem Int Ed, 2014, 53:2362-2365.
Dallmann et al., "Structure and dynamics of triazole-linked DNA: biocompatibility explained," Chem Eur J, 2011, 17:14714-14717.
Madhuri and Kumar, "Design and synthesis of dephosphono DNA analogues containing 1, 2, 3-triazole linker and their UV-melting studies with DNA/RNA," Nucleosides, Nucleotides and Nucleic Acids, Feb. 3, 2012, 31(2):97-111.
El-Sagheer and Brown, "Combined nucleobase and backbone modifications enhance DNA duplex stability and preserve biocompatibility," Chem Sci, 2014, 5:253-259.
Shivalingam et al., "Molecular requirements of high-fidelity replication-competent DNA backbones for orthogonal chemical ligation," J Am Chem Soc, Jan. 18, 2017, 139:1575-1583.
Palframan et al., "Synthesis of triazole-linked morpholino oligonucleotides via Cu catalysed cycloaddition," Org Biomol Chem, 2016, 14:3112-3119.
Singh and Wengel, "Universality of LNA-mediated high-affinity nucleic acid recognition," Chem Commun, 1998, 1247-1248.
Obika et al., "Stability and structural features of the duplexes containing nucleoside analogues with a fixed N-type conformation, 2'-O,4'-C-methyleneribonucleosides," Tetrahedron Lett, 1998, 39:5401-5404.
Kaur, Babu, and Maiti, "Perspectives on chemistry and therapeutic applications of locked nucleic acid (LNA)," Chem Rev, 2007, 107:4672-4697.
Watts, "Locked nucleic acid: Tighter is different," Chem Commun, May 2013, 49:5618-5620.
Obika et al., "2'-O,4'-C-methylene bridged nucleic acid (2',4'-BNA): Synthesis and triplex forming properties," Bioorg Med Chem, 2001, 9:1001-1011.
Miller and Kool, "A simple method for electrophilic functionalization of DNA," Org Lett, Sep. 19, 2002, 4(21):3599-3601.
Miller and Kool, "Versatile 5'-Functionalization of oligonucleotides on solid support: Amines, azides, thiols, and thioethers via phosphorus chemistry," J Org Chem, Mar. 5, 2004, 69:2404-2410.
Chan et al., "Polytriazoles as copper(I)-stabilizing ligands in catalysis," Org Lett, Jul. 30, 2004, 6(17):2853-2855.
Bood, M., et al. "Fluorescent nucleobase analogues for base-base FRET in nucleic acids: synthesis, photophysics and applications," BEILSTEIN Journal of Organic Chemistry, 2018, 14, 114-29.
Minuth, M. and Richert, C., "A Nucleobase Analogue that Pairs Strongly with Adenine," Angewandte Chemie International Edition, 2013, 52, 10874-7.
Makarova et al., Methods in Molecular Biology, 2015, 1311:47-75.

* cited by examiner

SEQUENCE LISTING

```
<160> NUMBER OF SEQ ID NOS: 40

<210> SEQ ID NO 1
<211> LENGTH: 81
<212> TYPE: DNA
<213> ORGANISM: Artificial Sequence
<220> FEATURE:
<223> OTHER INFORMATION: modified template (ON15)
<220> FEATURE:
<221> NAME/KEY: modified_base
<222> LOCATION: (23)..(23)
<223> OTHER INFORMATION: m5c
<220> FEATURE:
<221> NAME/KEY: misc_feature
<222> LOCATION: (23)..(24)
<223> OTHER INFORMATION: triazole linkage
<220> FEATURE:
<221> NAME/KEY: misc_feature
<222> LOCATION: (24)..(24)
<223> OTHER INFORMATION: n is LNA thymidine

<400> SEQUENCE: 1
gcattcgagc aacgtaagat cgnnagcaca caatctcaca ctctggaatt cacactgaca        60
atactgccga cacacataac c                                                  81

<210> SEQ ID NO 2
<211> LENGTH: 80
<212> TYPE: DNA
<213> ORGANISM: Artificial Sequence
<220> FEATURE:
<223> OTHER INFORMATION: unmodified template

<400> SEQUENCE: 2
acgttagcac gaagaggcat cttagcacac aatctcacac tctggaattc acactgacaa        60
tactcgcgaa cacacccaat                                                    80

<210> SEQ ID NO 3
<211> LENGTH: 19
<212> TYPE: DNA
<213> ORGANISM: Artificial Sequence
<220> FEATURE:
<223> OTHER INFORMATION: primer used for modified template
<220> FEATURE:
<221> NAME/KEY: misc_feature
<222> LOCATION: (1)..(1)
<223> OTHER INFORMATION: t derivatised with amidohexylfuorescein

<400> SEQUENCE: 3
tggttatgtg tgtcggcag                                                     19

<210> SEQ ID NO 4
```

```
<211> LENGTH: 19
<212> TYPE: DNA
<213> ORGANISM: Artificial Sequence
<220> FEATURE:
<223> OTHER INFORMATION: primer used for unmodified template
<220> FEATURE:
<221> NAME/KEY: misc_feature
<222> LOCATION: (1)..(1)
<223> OTHER INFORMATION: t derivatised with amidohexylfuorescein

<400> SEQUENCE: 4
tattgggtgt gttcgcgag                                                    19

<210> SEQ ID NO 5
<211> LENGTH: 13
<212> TYPE: DNA
<213> ORGANISM: Artificial Sequence
<220> FEATURE:
<223> OTHER INFORMATION: modified oligonucleotide ON2
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: n is LNA thymidine

<400> SEQUENCE: 5
cgacgnntgc agc                                                          13

<210> SEQ ID NO 6
<211> LENGTH: 13
<212> TYPE: DNA
<213> ORGANISM: Artificial Sequence
<220> FEATURE:
<223> OTHER INFORMATION: modified oligonucleotide ON3
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage

<400> SEQUENCE: 6
cgacgnttgc agc                                                          13

<210> SEQ ID NO 7
<211> LENGTH: 13
<212> TYPE: DNA
<213> ORGANISM: Artificial Sequence
<220> FEATURE:
<223> OTHER INFORMATION: modified oligonucleotide ON5
<220> FEATURE:
<221> NAME/KEY: misc_feature
<222> LOCATION: (6)..(6)
<223> OTHER INFORMATION: n is 5-methylcytosine LNA
<220> FEATURE:
<221> NAME/KEY: misc_feature
<222> LOCATION: (6)..(7)
<223> OTHER INFORMATION: triazole linkage

<400> SEQUENCE: 7
cgacgnttgc agc                                                          13
```

```
<210> SEQ ID NO 8
<211> LENGTH: 13
<212> TYPE: DNA
<213> ORGANISM: Artificial Sequence
<220> FEATURE:
<223> OTHER INFORMATION: modified oligonucleotide ON6
<220> FEATURE:
<221> NAME/KEY: misc_feature
<222> LOCATION: (6)..(6)
<223> OTHER INFORMATION: n is 5-methylcytosine LNA
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: n is LNA thymidine

<400> SEQUENCE: 8
cgacgnntgc agc                                                          13

<210> SEQ ID NO 9
<211> LENGTH: 13
<212> TYPE: DNA
<213> ORGANISM: Artificial Sequence
<220> FEATURE:
<223> OTHER INFORMATION: modified oligonucleotide ON8
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: misc_feature
<222> LOCATION: (5)..(5)
<223> OTHER INFORMATION: n is LNA thymidine
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage
<220> FEATURE:
<221> NAME/KEY: misc_feature
<222> LOCATION: (10)..(10)
<223> OTHER INFORMATION: n is LNA thymidine

<400> SEQUENCE: 9
cganntctnn agc                                                          13

<210> SEQ ID NO 10
<211> LENGTH: 13
<212> TYPE: DNA
<213> ORGANISM: Artificial Sequence
<220> FEATURE:
<223> OTHER INFORMATION: modified oligonucleotide ON9
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: modified_base
<222> LOCATION: (9)..(9)
<223> OTHER INFORMATION: m5c
<220> FEATURE:
```

```
<221> NAME/KEY: misc_feature
<222> LOCATION: (9)..(10)
<223> OTHER INFORMATION: triazole linkage

<400> SEQUENCE: 10
cganttctnt agc                                                        13

<210> SEQ ID NO 11
<211> LENGTH: 13
<212> TYPE: DNA
<213> ORGANISM: Artificial Sequence
<220> FEATURE:
<223> OTHER INFORMATION: modified oligonucleotide ON11
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: misc_feature
<222> LOCATION: (7)..(7)
<223> OTHER INFORMATION: n is 5-methylcytosine LNA

<400> SEQUENCE: 11
cgacgnntgc agc                                                        13

<210> SEQ ID NO 12
<211> LENGTH: 13
<212> TYPE: DNA
<213> ORGANISM: Artificial Sequence
<220> FEATURE:
<223> OTHER INFORMATION: modified oligonucleotide ON12
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: triazole linkage
<220> FEATURE:
<221> NAME/KEY: modified_base
<222> LOCATION: (7)..(7)
<223> OTHER INFORMATION: m5c

<400> SEQUENCE: 12
cgacgnntgc agc                                                        13

<210> SEQ ID NO 13
<211> LENGTH: 13
<212> TYPE: DNA
<213> ORGANISM: Artificial Sequence
<220> FEATURE:
<223> OTHER INFORMATION: modified oligonucleotide ON13
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: misc_feature
<222> LOCATION: (5)..(5)
<223> OTHER INFORMATION: n is 5-methylcytosine LNA
<220> FEATURE:
<221> NAME/KEY: modified_base
<222> LOCATION: (9)..(9)
<223> OTHER INFORMATION: m5c
```

<220> FEATURE:
<221> NAME/KEY: misc_feature
<222> LOCATION: (9)..(10)
<223> OTHER INFORMATION: triazole linkage
<220> FEATURE:
<221> NAME/KEY: misc_feature
<222> LOCATION: (10)..(10)
<223> OTHER INFORMATION: n is 5-methylcytosine LNA

<400> SEQUENCE: 13
cganntctnn agc                                                        13

<210> SEQ ID NO 14
<211> LENGTH: 13
<212> TYPE: DNA
<213> ORGANISM: Artificial Sequence
<220> FEATURE:
<223> OTHER INFORMATION: modified oligonucleotide ON14
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: triazole linkage
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: triazole linkage
<220> FEATURE:
<221> NAME/KEY: modified_base
<222> LOCATION: (10)..(10)
<223> OTHER INFORMATION: m5c

<400> SEQUENCE: 14
cganntctnn agc                                                        13

<210> SEQ ID NO 15
<211> LENGTH: 81
<212> TYPE: DNA
<213> ORGANISM: Artificial Sequence
<220> FEATURE:
<223> OTHER INFORMATION: modified oligonucleotide ON15
<220> FEATURE:
<221> NAME/KEY: modified_base
<222> LOCATION: (23)..(23)
<223> OTHER INFORMATION: m5c
<220> FEATURE:
<221> NAME/KEY: misc_feature
<222> LOCATION: (23)..(24)
<223> OTHER INFORMATION: triazole linkage
<220> FEATURE:
<221> NAME/KEY: misc_feature
<222> LOCATION: (24)..(24)
<223> OTHER INFORMATION: n is LNA thymidine

<400> SEQUENCE: 15
gcattcgagc aacgtaagat cgnnagcaca caatctcaca ctctggaatt cacactgaca    60
atactgccga cacacataac c                                              81

<210> SEQ ID NO 16
<211> LENGTH: 25
<212> TYPE: DNA

```
<213> ORGANISM: Artificial Sequence
<220> FEATURE:
<223> OTHER INFORMATION: splint used for ON8 and ON9

<400> SEQUENCE: 16 tttttgcta gagaagtcgt ttttt                                            25

<210> SEQ ID NO 17
<211> LENGTH: 25
<212> TYPE: DNA
<213> ORGANISM: Artificial Sequence
<220> FEATURE:
<223> OTHER INFORMATION: Splint used for ON13 and ON14

<400> SEQUENCE: 17 tttttgctg gagaggtcgt ttttt                                            25

<210> SEQ ID NO 18
<211> LENGTH: 18
<212> TYPE: DNA
<213> ORGANISM: Artificial Sequence
<220> FEATURE:
<223> OTHER INFORMATION: splint used in synthesis of an 81-mer template
      incorporating a single LNA-tiazole linkage

<400> SEQUENCE: 18
tgtgtgctag cgatctta                                                   18

<210> SEQ ID NO 19
<211> LENGTH: 23
<212> TYPE: DNA
<213> ORGANISM: Artificial Sequence
<220> FEATURE:
<223> OTHER INFORMATION: ON 18
<220> FEATURE:
<221> NAME/KEY: misc_feature
<222> LOCATION: (23)..(23)
<223> OTHER INFORMATION: n is 3'-alkyne 5'-methylcytosine

<400> SEQUENCE: 19
gcattcgagc aacgtaagat cgn                                             23

<210> SEQ ID NO 20
<211> LENGTH: 58
<212> TYPE: DNA
<213> ORGANISM: Artificial Sequence
<220> FEATURE:
<223> OTHER INFORMATION: ON 32
<220> FEATURE:
<221> NAME/KEY: misc_feature
<222> LOCATION: (1)..(1)
<223> OTHER INFORMATION: n is 5'-azide (N3) LNA thymidine

<400> SEQUENCE: 20
nagcacacaa tctcacactc tggaattcac actgacaata ctgccgacac acataacc       58

<210> SEQ ID NO 21
<211> LENGTH: 13
<212> TYPE: DNA
<213> ORGANISM: Artificial Sequence
<220> FEATURE:
<223> OTHER INFORMATION: ON 33
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
```

```
<223> OTHER INFORMATION: normal phosphodiester linkage
<220> FEATURE:
<221> NAME/KEY: modified_base
<222> LOCATION: (7)..(7)
<223> OTHER INFORMATION: m5c

<400> SEQUENCE: 21
cgacgcctgc agc                                                        13

<210> SEQ ID NO 22
<211> LENGTH: 13
<212> TYPE: DNA
<213> ORGANISM: Artificial Sequence
<220> FEATURE:
<223> OTHER INFORMATION: ON 34
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage
<220> FEATURE:
<221> NAME/KEY: misc_feature
<222> LOCATION: (7)..(7)
<223> OTHER INFORMATION: n is 5-methylcytosine LNA

<400> SEQUENCE: 22
cgacgcntgc agc                                                        13

<210> SEQ ID NO 23
<211> LENGTH: 13
<212> TYPE: DNA
<213> ORGANISM: Artificial Sequence
<220> FEATURE:
<223> OTHER INFORMATION: DNA target

<400> SEQUENCE: 23
gctgcaggcg tcg                                                        13

<210> SEQ ID NO 24
<211> LENGTH: 13
<212> TYPE: RNA
<213> ORGANISM: Artificial Sequence
<220> FEATURE:
<223> OTHER INFORMATION: RNA target

<400> SEQUENCE: 24
gcugcaggcg ucg                                                        13

<210> SEQ ID NO 25
<211> LENGTH: 13
<212> TYPE: DNA
<213> ORGANISM: Artificial Sequence
<220> FEATURE:
<223> OTHER INFORMATION: ON 1
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage

<400> SEQUENCE: 25
cgacgcttgc agc                                                        13
```

```
<210> SEQ ID NO 26
<211> LENGTH: 13
<212> TYPE: DNA
<213> ORGANISM: Artificial Sequence
<220> FEATURE:
<223> OTHER INFORMATION: ON 4
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (6)..(7)
<223> OTHER INFORMATION: normal phosphodiester linkage
<220> FEATURE:
<221> NAME/KEY: misc_feature
<222> LOCATION: (7)..(7)
<223> OTHER INFORMATION: n is LNA thymidine

<400> SEQUENCE: 26
cgacgcntgc agc                                                        13

<210> SEQ ID NO 27
<211> LENGTH: 13
<212> TYPE: DNA
<213> ORGANISM: Artificial Sequence
<220> FEATURE:
<223> OTHER INFORMATION: ON35
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: normal phosphodiester linkage
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (9)..(10)
<223> OTHER INFORMATION: normal phosphodiester linkage
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (10)..(10)
<223> OTHER INFORMATION: m5c

<400> SEQUENCE: 27
cgacctctcc agc                                                        13

<210> SEQ ID NO 28
<211> LENGTH: 13
<212> TYPE: DNA
<213> ORGANISM: Artificial Sequence
<220> FEATURE:
<223> OTHER INFORMATION: ON36
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(5)
<223> OTHER INFORMATION: normal phosphodiester linkage
<220> FEATURE:
<221> NAME/KEY: misc_feature
<222> LOCATION: (5)..(5)
<223> OTHER INFORMATION: n is 5-methylcytosine LNA
<220> FEATURE:
```

```
<221> NAME/KEY: modified_base
<222> LOCATION: (9)..(9)
<223> OTHER INFORMATION: m5c
<220> FEATURE:
<221> NAME/KEY: misc_feature
<222> LOCATION: (9)..(10)
<223> OTHER INFORMATION: normal phosphodiester linkage
<220> FEATURE:
<221> NAME/KEY: misc_feature
<222> LOCATION: (10)..(10)
<223> OTHER INFORMATION: n is 5-methylcytosine LNA

<400> SEQUENCE: 28
cgacntctcn agc                                                      13

<210> SEQ ID NO 29
<211> LENGTH: 18
<212> TYPE: DNA
<213> ORGANISM: Artificial Sequence
<220> FEATURE:
<223> OTHER INFORMATION: primer used for PCR of an 81-mer template
      incorporating a single LNA-triazole linkage - modified template

<400> SEQUENCE: 29
gcattcgagc aacgtaag                                                 18

<210> SEQ ID NO 30
<211> LENGTH: 18
<212> TYPE: DNA
<213> ORGANISM: Artificial Sequence
<220> FEATURE:
<223> OTHER INFORMATION: primer used for PCR of an 81-mer template
      incorporating a single LNA-triazole linkage - modified template

<400> SEQUENCE: 30
ggttatgtgt gtcggcag                                                 18

<210> SEQ ID NO 31
<211> LENGTH: 18
<212> TYPE: DNA
<213> ORGANISM: Artificial Sequence
<220> FEATURE:
<223> OTHER INFORMATION: primer used for PCR of an 81-mer template
      incorporating a single LNA-triazole linkage - unmodified template

<400> SEQUENCE: 31
attgggtgtg ttcgcgag                                                 18

<210> SEQ ID NO 32
<211> LENGTH: 18
<212> TYPE: DNA
<213> ORGANISM: Artificial Sequence
<220> FEATURE:
<223> OTHER INFORMATION: primer used for PCR of an 81-mer template
      incorporating a single LNA-triazole linkage - unmodified template

<400> SEQUENCE: 32
acgttagcac gaagaggc                                                 18

<210> SEQ ID NO 33
<211> LENGTH: 13
<212> TYPE: DNA
<213> ORGANISM: Artificial Sequence
<220> FEATURE:
<223> OTHER INFORMATION: DNA target

<400> SEQUENCE: 33
gctgcaagcg tcg                                                      13
```

```
<210> SEQ ID NO 34
<211> LENGTH: 13
<212> TYPE: RNA
<213> ORGANISM: Artificial Sequence
<220> FEATURE:
<223> OTHER INFORMATION: RNA target

<400> SEQUENCE: 34
gcugcaagcg ucg                                                         13

<210> SEQ ID NO 35
<211> LENGTH: 13
<212> TYPE: DNA
<213> ORGANISM: Artificial Sequence
<220> FEATURE:
<223> OTHER INFORMATION: ON7
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (9)..(9)
<223> OTHER INFORMATION: m5c

<400> SEQUENCE: 35
cgacttctct agc                                                         13

<210> SEQ ID NO 36
<211> LENGTH: 13
<212> TYPE: DNA
<213> ORGANISM: Artificial Sequence
<220> FEATURE:
<223> OTHER INFORMATION: ON 10
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (5)..(5)
<223> OTHER INFORMATION: n is LNA thymidine
<220> FEATURE:
<221> NAME/KEY: modified_base
<222> LOCATION: (9)..(9)
<223> OTHER INFORMATION: m5c
<220> FEATURE:
<221> NAME/KEY: misc_feature
<222> LOCATION: (10)..(10)
<223> OTHER INFORMATION: n is LNA thymidine

<400> SEQUENCE: 36
cgacntctcn agc                                                         13

<210> SEQ ID NO 37
<211> LENGTH: 13
<212> TYPE: DNA
<213> ORGANISM: Artificial Sequence
<220> FEATURE:
<223> OTHER INFORMATION: DNA target

<400> SEQUENCE: 37
gctagagaag tcg                                                         13

<210> SEQ ID NO 38
<211> LENGTH: 13
<212> TYPE: RNA
<213> ORGANISM: Artificial Sequence
<220> FEATURE:
```

```
-continued

<223> OTHER INFORMATION: RNA target

<400> SEQUENCE: 38
gcuagagaag ucg                                                    13

<210> SEQ ID NO 39
<211> LENGTH: 13
<212> TYPE: DNA
<213> ORGANISM: Artificial Sequence
<220> FEATURE:
<223> OTHER INFORMATION: DNA target

<400> SEQUENCE: 39
gctggagagg tcg                                                    13

<210> SEQ ID NO 40
<211> LENGTH: 13
<212> TYPE: RNA
<213> ORGANISM: Artificial Sequence
<220> FEATURE:
<223> OTHER INFORMATION: RNA target

<400> SEQUENCE: 40
gcuagagaag ucg                                                    13
```

OLIGONUCLEOTIDES

CROSS REFERENCE TO RELATED APPLICATIONS

This application claims the benefit under 35 U.S.C. § 119(e) of U.S. Provisional Patent Application No. 62/533,273, filed Jul. 17, 2017, the entire disclosure of which is incorporated herein by reference.

The project leading to this application has received funding from the European Union's Horizon 2020 research and innovation programme under the Marie Sklodowska-Curie grant agreement no: 656872.

SEQUENCE LISTING

Incorporated by reference in its entirety is a computer-readable nucleotide/amino acid sequence listing submitted concurrently herewith and identified as follows: One 13.7 KB ASCII (Text) file named "280045SeqList.txt"_created on Oct. 5, 2018.

INTRODUCTION

The present invention relates to oligonucleotides.

BACKGROUND OF THE INVENTION

Oligonucleotides (ONs) are fundamental to many areas of molecular biology and are essential tools in technologies such as DNA sequencing, forensic and genetic analysis. They can also be used therapeutically.

Oligonucleotides containing triazole inter-nucleoside linkages have attracted considerable attention in the last decade.[1-6] The most intensively studied of these is the biocompatible triazole-linkage shown in Formula (i) below which has recently emerged as an important tool in the chemical synthesis of long pieces of DNA.[7]

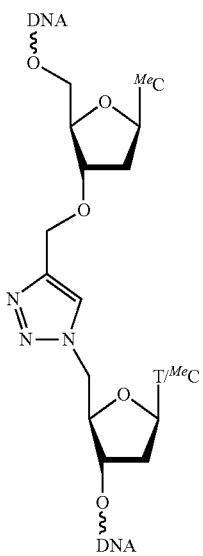

(i)

The triazole linkage shown in Formula (i) above is a mimic of natural phosphodiester-linked DNA and is functional in bacterial and human cells.[8-10] However, oligonucleotides incorporating this linkage form less stable duplexes with complementary RNA/DNA targets compared to unmodified DNA strands.[11,12] This makes them unfit for use as antisense oligonucleotides where high binding affinity for the target nucleic acid is essential.

This problem was partially addressed by the introduction of an aminoethylphenoxazine nucleobase (G-clamp) on the 3'-side of the triazole linkage (see Formula (ii) below), which significantly enhances the thermal stability of the modified duplex.[13]

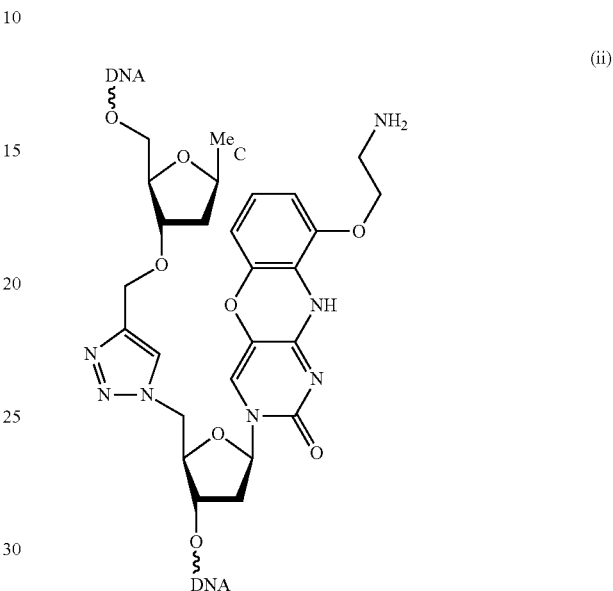

(ii)

However, G-clamp present in Formula (ii) is mildly mutagenic[14] and, being a mimic of 2'-deoxycytidine, it does not provide a solution for all nucleobase combinations.

Recently, oligonucleotides featuring triazole-linked morpholino nucleotides (see Formula (iii) below) have been shown to hybridize to their RNA targets with slightly improved affinity compared to triazole alone.[15] However, the resulting duplexes remain thermally less stable than their unmodified counterparts.

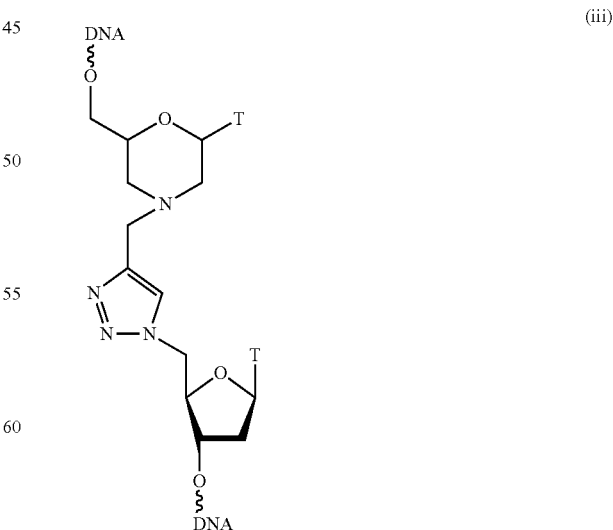

(iii)

The use of triazole inter-nucleoside linkages improves stability of the ON to nucleases. However, in view of the foregoing, there is clearly a need for further improved triazole-linked oligonucleotides. In particular, there is a need for further improved triazole-linked oligonucleotides that possess improved binding affinities for complimentary DNA and/or RNA strands.

The present invention was devised with the foregoing in mind.

SUMMARY OF THE INVENTION

According to one aspect of the present invention, there is provided an oligonucleotide as defined herein.

According to a second aspect of the present invention, there is provided a process for making an oligonucleotide as defined herein.

According to a third aspect of the present invention, there is provided an oligonucleotide as defined herein for use in therapy.

According to a fourth aspect of the present invention, there is provided a use of an oligonucleotide as defined herein, as antisense RNA or interference RNA (RNAi, e.g. siRNA or miRNA) or an RNA component of a CRISPR-Cas system (e.g. crRNA, tracrRNA or gRNA).

According to another aspect of the present invention, there is provided the use of an oligonucleotide as defined herein as:

a template for amplification in a polymerase chain reaction (PCR):

as a template in a DNA replication process;

as a template in a transcription process to provide a corresponding RNA transcript, or as a template in a reverse transcription process to provide a corresponding DNA transcript;

as template in a translation process to produce a corresponding protein or peptide; or to guide one or more proteins of interest to a target DNA or RNA.

According to another aspect of the present invention, there is provided a method for amplifying an oligonucleotide sequence as defined herein.

According to an eighth aspect of the present invention, there is provided a method for replicating an oligonucleotide sequence as defined herein.

According to a ninth aspect of the present invention, there is provided a method for producing a ribonucleic acid (RNA) sequence or deoxyribonucleic acid (DNA) sequence as defined herein.

TCT CAC ACT CTG GAA TTC ACA CTG ACA ATA CTG CCG ACA CAC ATA ACC (SEQ ID NO: 15).

Figure 20:
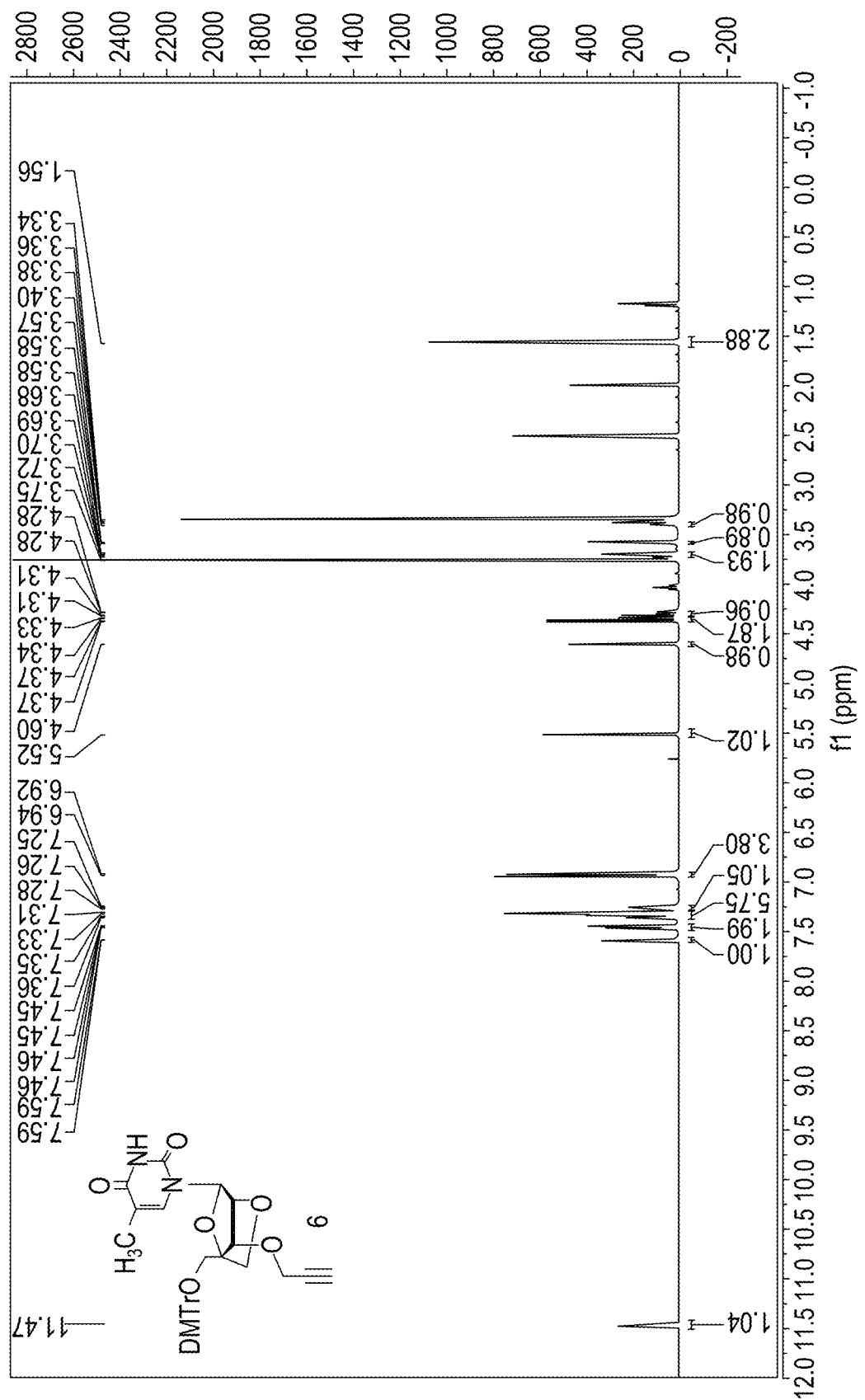

FIG. 20 shows the $^1$H NMR spectrum of 5'-O-(4,4'-dimethoxytrityl)-3'-O-propargyl-LNA thymidine (6).

Figure 21:
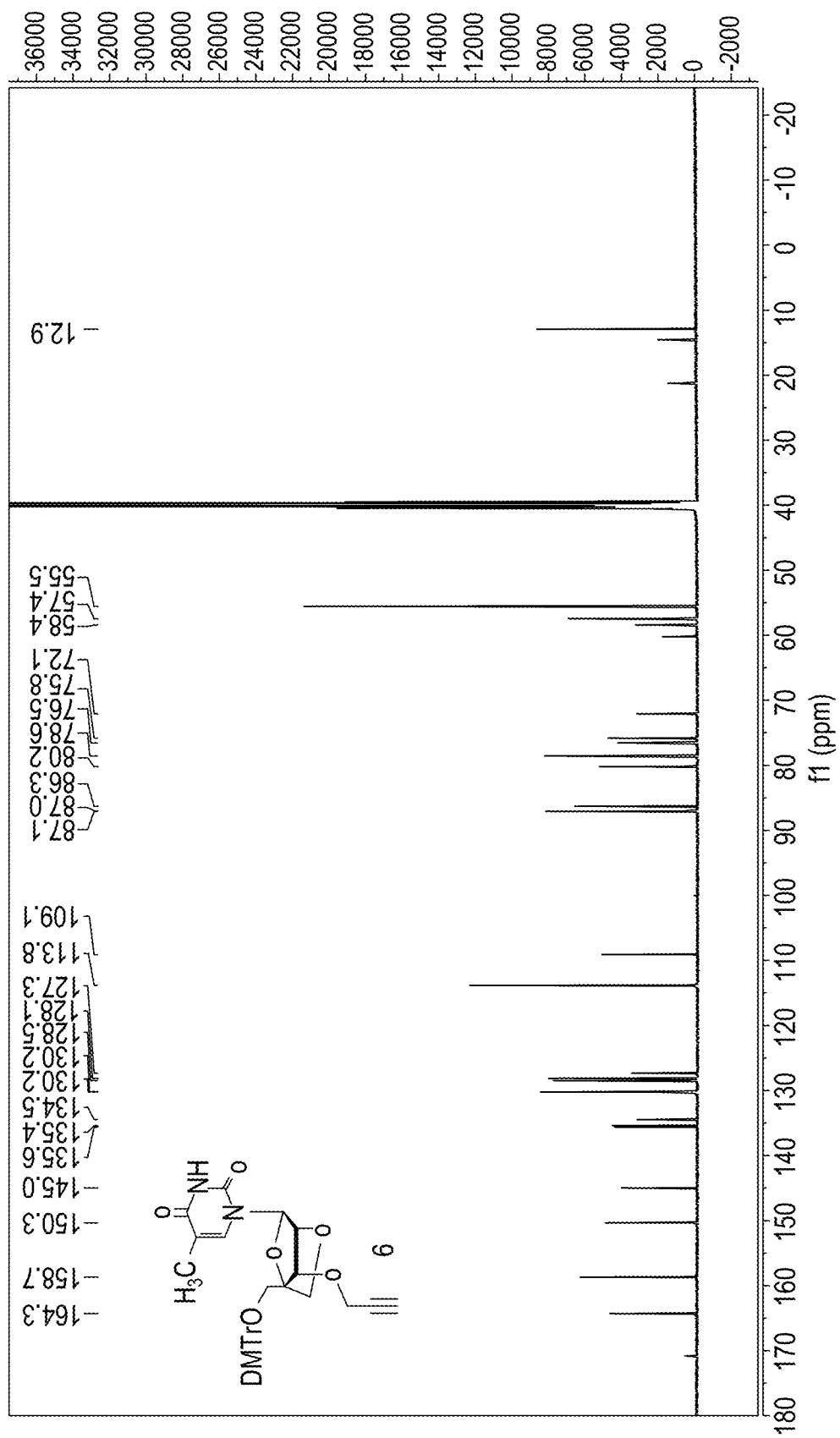

FIG. 21 shows the $^{13}$C NMR spectrum of 5'-O-(4,4'-dimethoxytrityl)-3'-O-propargyl-LNA thymidine (6).

Figure 22:
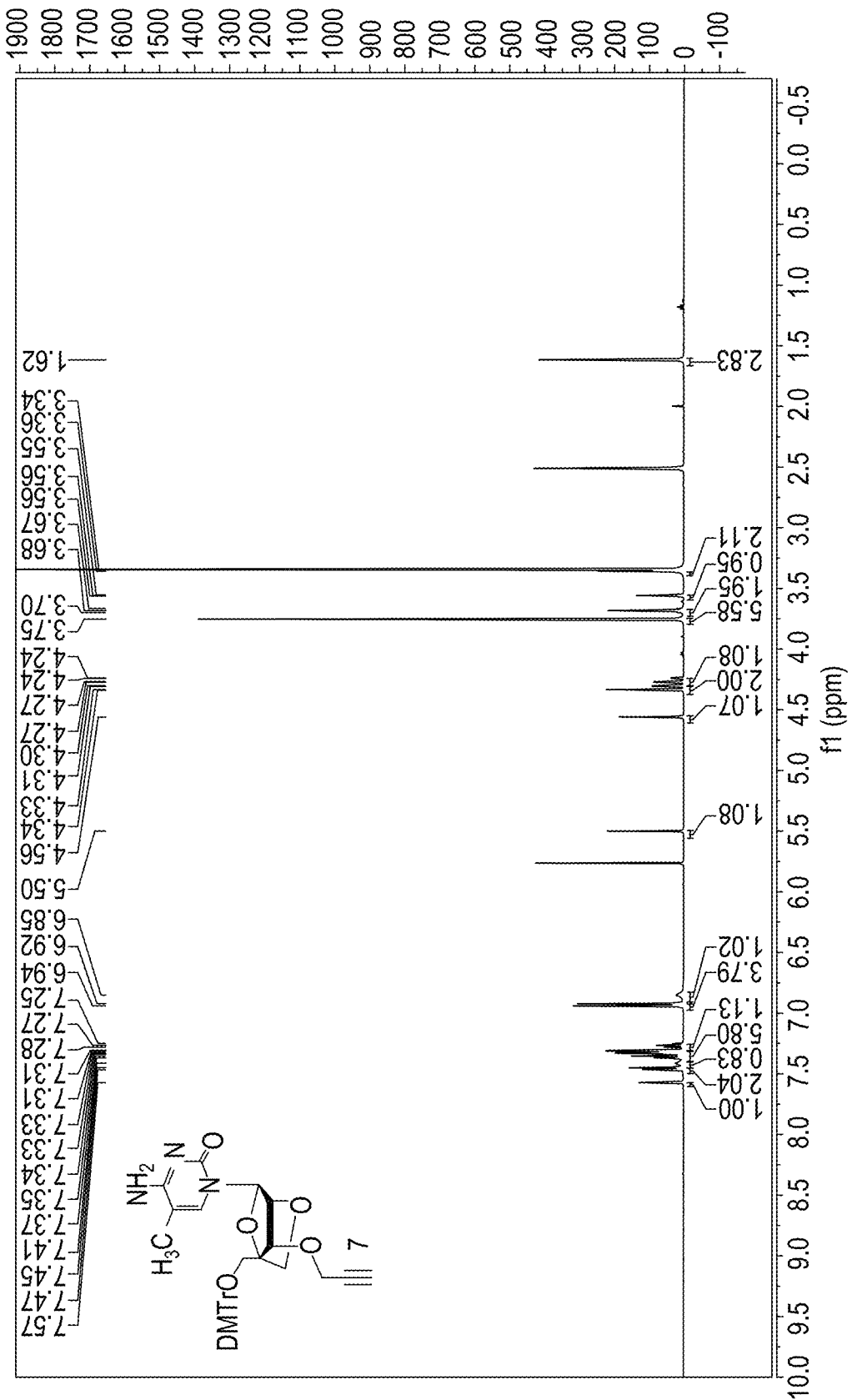

FIG. 22 shows the $^1$H NMR spectrum of 5'-O-(4,4'-dimethoxytrityl)-3'-O-propargyl-5-methyl LNA cytidine (7).

Figure 23:
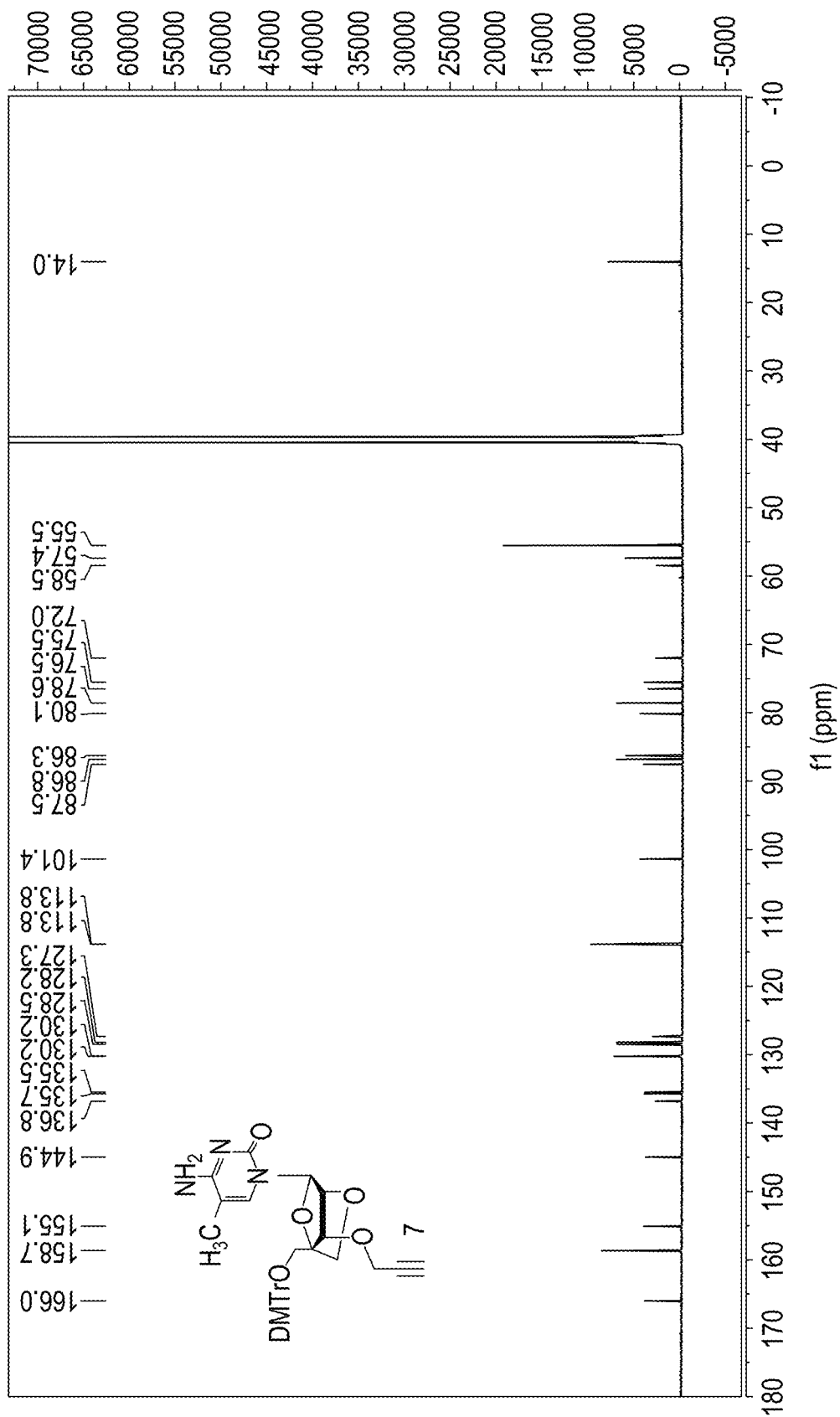

FIG. 23 shows the $^{13}$C NMR spectrum of 5'-O-(4,4'-dimethoxytrityl)-3'-O-propargyl-5-methyl LNA cytidine (7).

Figure 24:
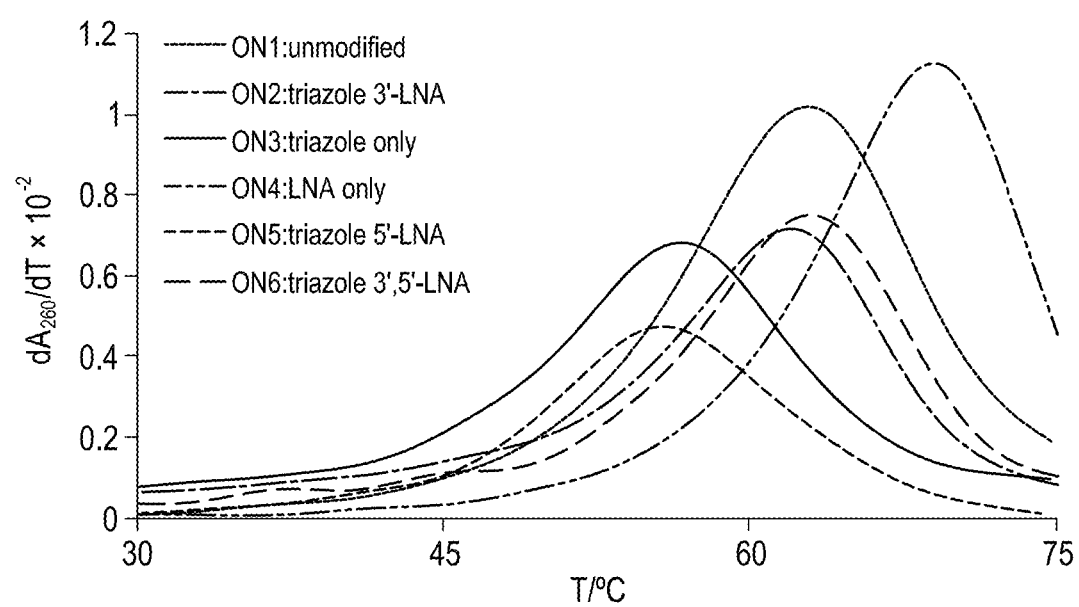

FIG. 24 shows the UV melting studies (derivatives of melting curves). DNA:RNA hybrid duplex containing a triazole linkage are stabilized by the introduction of LNA next to the triazole linkage (compare ON2 and ON3) For sequences see Table 5.

Figure 25:
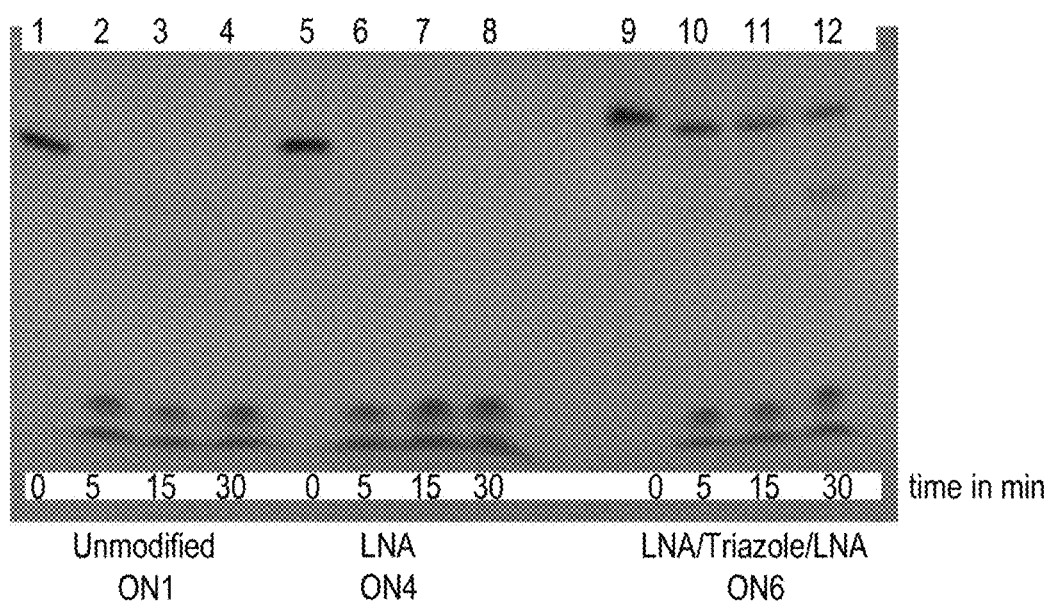

FIG. 25 shows LNA triazole stabilisation of oligonucleotides to 3'-exonuclease digestion. The unmodified ON (lanes 2-4) and LNA ON (lanes 6-8) were fully digested within 5 min whereas the LNA-triazole-LNA ON was still visible after 30 min (lane 12).

Figure 26:
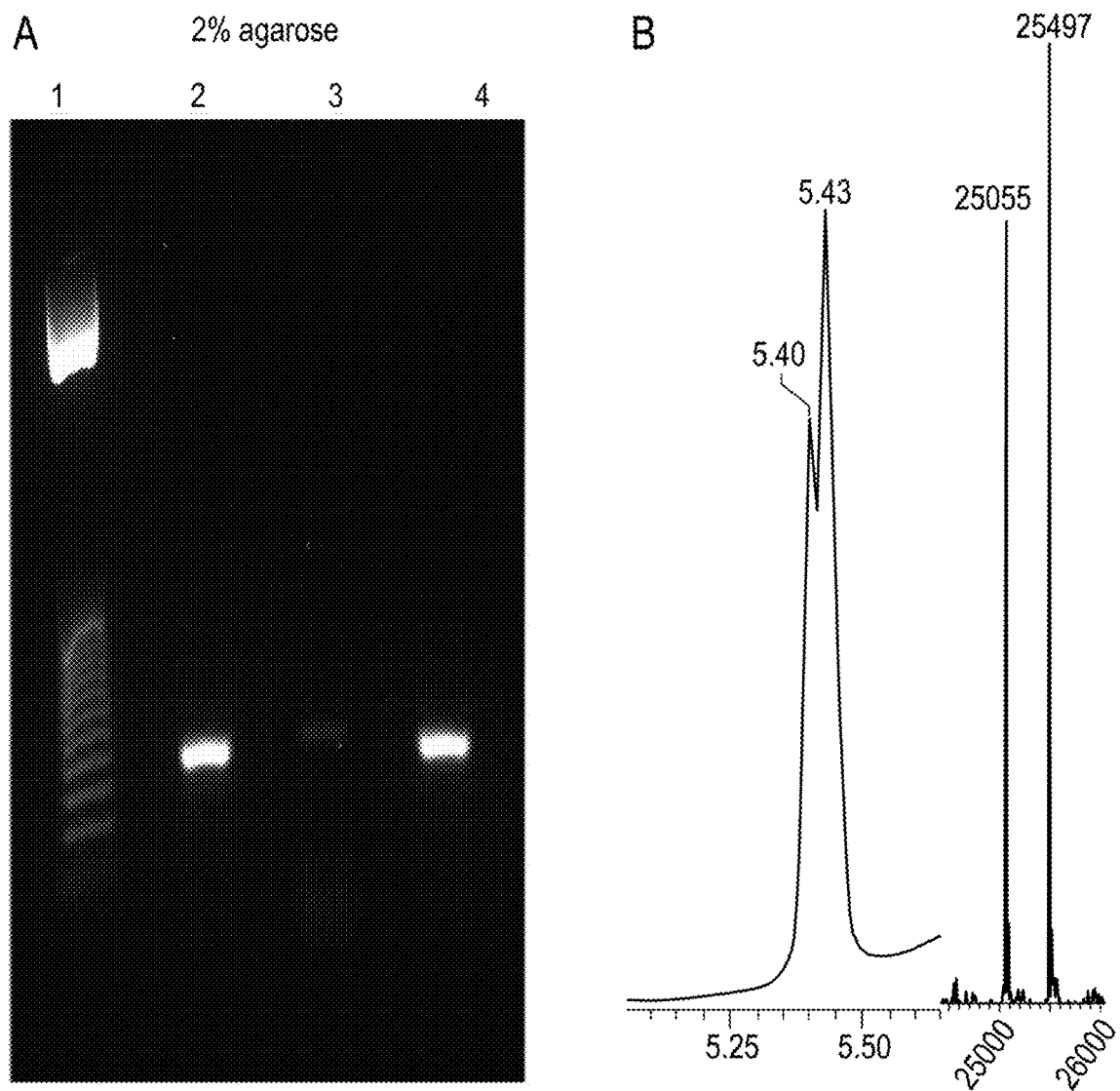

FIG. 26 shows LNA triazole DNA template is correctly amplified by PCR. A) 2% agarose gel using template GCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 1) where t represent triazole linkage and TL is LNA thymidine. Lane 1; 25 bp ladder. Lane 2; PCR reaction using modified template. Lane 3; negative control, PCR reaction with primers but no template. Lane 4; positive control, PCR reaction with unmodified template. B) UV trace from HPLC of HPLC/mass spec and ESI mass spectrum of the PCR product (both strands). [M+A] strand 1: calc. 25053, found 25055. Strand 2: calc. 25496, found 25497.

DETAILED DESCRIPTION OF THE INVENTION

Definitions

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or examples of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

The phrase "oligonucleotide of the invention" means those oligonucleotides which are disclosed herein, both generically and specifically.

The term "oligonucleotide" refers to a polynucleotide strand. It will be appreciated by those skilled in the art that an oligonucleotide has a 5' and a 3' end and comprises a sequence of nucleosides linked together by inter-nucleoside linkages.

The terms "oligonucleotide analogue" and "nucleotide analogue" refer to any modified synthetic analogues of oligonucleotides or nucleotides respectively that are known in the art. Examples of oligonucleotide analogues include peptide nucleic acids (PNAs), morpholino oligonucleotides, phosphorothioate oligonucleotides, phosphorodithioate oligonucleotides, alkylphosphonate oligonucleotides, acylphosphonate oligonucleotides and phosphoramidate oligonucleotides.

The term "nucleobase analogue" refers to any analogues of nucleobases known in the art. The skilled person will appreciate there to be numerous natural and synthetic nucleobase analogues available in the art which could be employed in the present invention. As such, the skilled person will readily be able to identify suitable nucleobase analogues for use in the present invention. Commonly available nucleobase analogues are commercially available from a number of sources (for example, see the Glen Research catalogue (http://www.glenresearch.com/Catalog/contents.php). It will also be appreciated that the term "nucleobase analogue" covers: universal/degenerate bases (e.g. 3-nitropyrrole, 5-nitroindole and hypoxanthine); fluorescent bases (e.g. tricyclic cytosine analogues (tCO, tCS) and 2-aminopurine); base analogues bearing reactive groups selected from alkynes, thiols or amines; and base analogues that can crosslink oligonucleotides to DNA, RNA or proteins (e.g. 5-bromouracil or 3-cyanovinyl carbazole).

The nucleobase or nucleobase analogue is attached to a sugar moiety (typically ribose or deoxyribose) or a ribose or deoxyribose mimic, for example a chemically modified sugar derivative (e.g. a chemically modified ribose or deoxyribose) or a cyclic group that functions as a synthetic mimic of a ribose or deoxyribose sugar moiety (e.g. the morpholino ring present in morpholino oligonucleotides). The term "nucleoside" is used herein to refer to a moiety composed of a sugar/a ribose or deoxyribose mimic bound to a nucleobase/nucleobase analogue. The term nucleoside as used herein excludes the inter-nucleoside linkage that connects adjacent nucleosides together. An "inter-nucleoside linkage" is a linking group that connects the rings of the sugar/ribose or deoxyribose mimic of adjacent nucleosides.

The terms "locked nucleic acid", "LNA" or "locked nucleoside" are used herein to refer to nucleic acids or nucleosides comprising a ribose or deoxyribose moiety in which the conformation of the ribose or deoxyribose ring is fixed or locked in a specific conformation, typically by a bridging group. Typically the bridging group connects the 2' and 4' carbon atoms of the ribose or deoxyribose rings and locks the ribose or deoxyribose in the 3'-endo conformation (which is often found in A-form duplexes). Examples of locked nucleic acid/nucleoside structures are well known in the art and are commercially available.

Oligonucleotides of the Invention

According to one aspect of the present invention, there is provided an oligonucleotide or oligonucleotide analogue having a 5' and a 3' end and comprising a sequence of nucleosides linked together by inter-nucleoside linkages, wherein at least one inter-nucleoside linkage is a triazole linker moiety and at least one nucleoside present in the portion of the oligonucleotide positioned at the 3' end of the triazole linker moiety is a locked nucleoside.

It will be appreciated by those skilled in the art that an inter-nucleoside linkage will have a 5' end (or 5' side) that links to the nucleoside on the 5' side, and 3' end (or 3' side) that links to the nucleoside on the 3' side of linkage. The 3' and 5' nomenclature is well established in the nucleic acid field.

The inventors have surprisingly found that the provision of a locked nucleoside on the 3' end of the triazole linker moiety is associated with a notable increase in thermal melting temperature of duplexes formed by the hybridisation of the oligonucleotide of the invention with a complimentary DNA or RNA strand.

In addition, the oligonucleotides of the present invention are much more stable to nuclease degradation when compared to corresponding oligonucleotides comprising just locked nucleosides alone. This indicates that the oligonucleotides of the present invention will be suitable for use in vivo.

The combination of the two aforementioned advantages (namely the increased nuclease stability together with the increase in the thermal melting temperatures observed upon binding of the oligonucleotides of the present invention to complimentary DNA or RNA stands) makes the oligonucleotides of the present invention particularly advantageous.

In an embodiment, the at least one locked nucleoside is either directly attached to the 3' end of the triazole linker moiety or it is positioned up to 5 nucleosides along from the 3' end of the triazole linker moiety. In a further embodiment, the at least one locked nucleoside is either directly attached to the 3' end of the triazole linker moiety or it is positioned up to 4 nucleosides along from the 3' end of this triazole linker moiety. In an embodiment, the at least one locked nucleoside is either directly attached to the 3' end of the triazole linker moiety or it is positioned up to 1, 2 or 3 nucleosides along from the 3' end of this linker moiety. It will be appreciated that when the locked nucleoside is positioned up to 1, 2, 3, 4, 5 or 6 nucleosides along from 3' end of the triazole linker moiety, the nucleosides positioned in between the 3' end of the triazole linker moiety and the locked nucleoside will be non-locked nucleosides (in which any ribose or deoxyribose sugar moiety present is not conformationally locked).

In a particular embodiment of the invention, the at least one locked nucleoside is directly attached to the 3' end of the triazole linker moiety.

In a further embodiment, the at least one locked nucleoside is directly attached to the 3' end of the triazole linker moiety at the 4' carbon of the locked ribose or deoxyribose ring.

The oligonucleotide may comprise multiple locked nucleosides in its sequence, for example there may be two, three, four, five or more locked nucleosides present. The additional locked nucleosides may be present at any position in the oligonucleotide.

In an embodiment, a further locked nucleoside is present in the portion of the oligonucleotide attached to the 5' end of the triazole linker moiety. In a particular embodiment, a further locked nucleoside is either directly attached to the 5' end of the triazole linker moiety or is positioned up to 5 (for example up to 2, 3 or 4) nucleosides along from the 5' end of the triazole linker moiety. In a further embodiment, a further locked nucleoside is directly attached to the 5' end of the triazole linker moiety. Suitably, the linker is attached to the 3' carbon atom of the ribose or deoxyribose ring of the locked nucleoside.

In a particular embodiment, the oligonucleotide comprises at least two locked nucleosides, one of which is directly attached to the 3' end of the triazole linker moiety and the other of which is directly linked to the 5' end of the triazole linker moiety. This particular embodiment of the invention is associated with even greater nuclease stability when compared to the oligonucleotides of the invention with just one locked nucleoside present at the 3' end of the triazole linkage. It is therefore expected that the oligonucleotides of this embodiment of the invention will be particularly suitable for in vivo applications.

The Triazole Linker Moiety

Any suitable triazole linker moiety known in the art may be used in the oligonucleotides of the present invention. The triazole linker moiety is an inter-nucleoside linkage that acts as a mimic of the phosphodiester linkages found in naturally occurring polynucleotides. Thus, any suitable phosphodiester mimic comprising a triazole ring that is known in the art may be used as an inter-nucleoside linkage in the oligonucleotides of the present invention.

Examples of suitable triazole linker moieties include any one of the triazole inter-nucleoside linkers described in U.S. Pat. No. 8,846,883, the entire contents of which are incorporated herein by reference. U.S. Pat. No. 8,846,883 describes how these triazole inter-nucleoside linkages can be formed by "click" chemistry in which an oligonucleotide with a terminal azide reacts with another oligonucleotide with a terminal alkyne group to form an inter-nucleoside linkage comprising a triazole ring.

In an embodiment, the triazole linker moiety is a group of Formula A or Formula B shown below:

Formula A

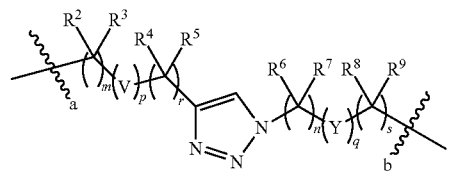

Formula B

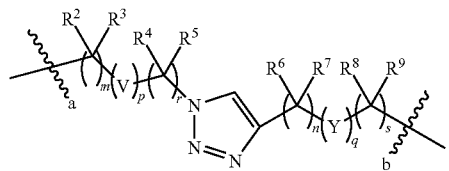

wherein:
- ⌇ₐ denotes the 5' end of the triazole linker moiety;
- ⌇ᵦ denotes the 3' end of triazole linker moiety;
- $R^2$, $R^3$, $R^4$, $R^5$, $R^6$, $R^7$, $R^8$ and $R^9$ are each independently selected from hydrogen or (1-4C)alkyl, wherein each (1-4C)alkyl is optionally substituted with one or more $NH_2$, OH or SH;
- V and Y are independently selected from O, S or $NR^x$, wherein $R^x$ is selected from hydrogen or (1-4C)alkyl;
- m, n, r and s are integers independently selected from 0, 1 or 2; and
- p and q are integers independently selected from 0 or 1;
- with the proviso that the sum of integers m, n, p, q, r and s is either 0, 1, 2, 3, 4, 5 or 6.

In a particular embodiment, the triazole linker moiety is of Formula A or B shown above, wherein:
- $R^2$, $R^3$, $R^4$, $R^5$, $R^6$, $R^7$, $R^8$ and $R^9$ are each independently selected from hydrogen or (1-4C)alkyl;
- V and Y are independently selected from O or $NR^x$, wherein $R^x$ is selected from hydrogen or (1-4C)alkyl;
- m, n, r and s are integers independently selected from 0 to 2; and
- p and q are integers independently selected from 0 or 1;
- with the proviso that the sum of integers m, n, p, q, r and s is either 0, 1, 2, 3, 4 or 5.

In a further embodiment, the triazole linker moiety is of Formula A or B shown above, wherein:
- $R^2$, $R^3$, $R^4$, $R^5$, $R^6$, $R^7$, $R^8$ and $R^9$ are hydrogen; V and Y are O;
- m, n, r and s are integers independently selected from 0 or 1; and
- p and q are integers independently selected from 0 or 1;
- with the proviso that the sum of integers m, n, p, q, r and s is either 1, 2, 3, 4 or 5.

In a further embodiment, the triazole linker moiety is selected from any one of the following structures:

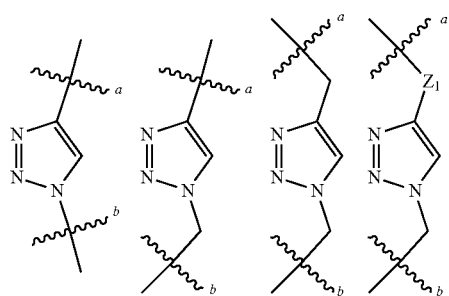

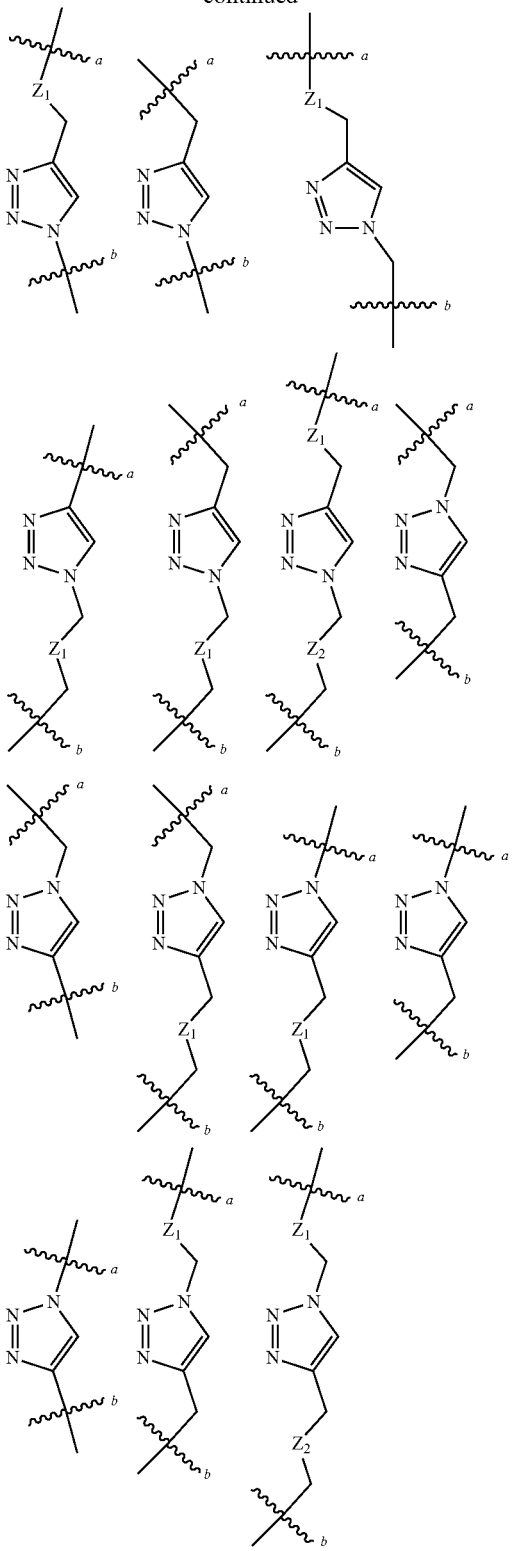

wherein:
$Z_1$ and $Z_2$ are independently selected from O or NH;
⌇ₐ denotes the 5' end of the triazole linker moiety; and
⌇ᵦ denotes the 3' end of triazole linker moiety.

In yet a further embodiment, the triazole linker moiety is selected from any one of the following structures:

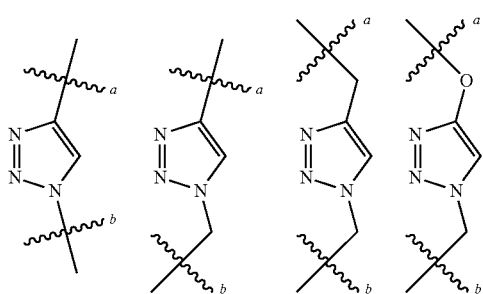

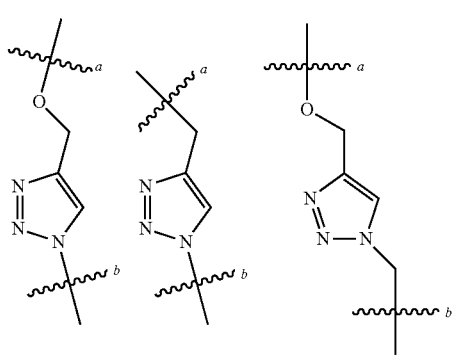

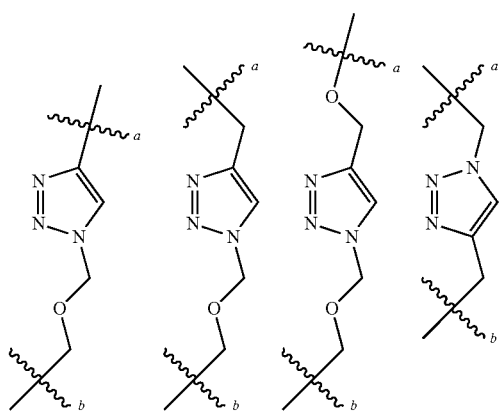

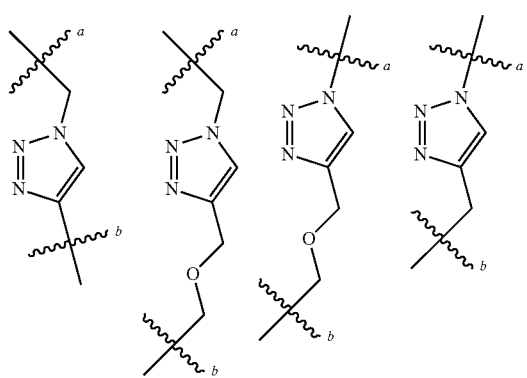

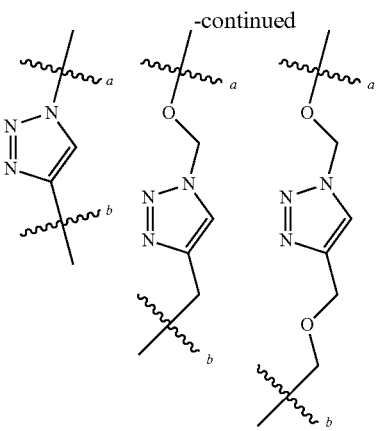

wherein:
$\sim_a$ denotes the 5' end of the triazole linker moiety; and
$\sim_b$ denotes the 3' end of triazole linker moiety.

In a particular embodiment, the triazole linker moiety has the following structural formula:

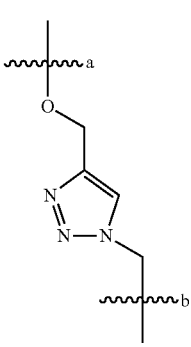

wherein:
$\sim_a$ denotes the 5' end of the triazole linker moiety; and
$\sim_b$ denotes the 3' end of triazole linker moiety.

The Locked Nucleoside

Locked nucleic acids are well known in the art. Any suitable locked nucleoside may be used in the present invention. Typically, the locked nucleoside has the general structure shown below:

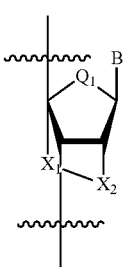

wherein:
$Q_1$ is selected from $CR^pR^q$, O, S or $NR^a$, wherein $R^p$ and $R^q$ are each independently selected from H, (1-4C)alkyl or halo, and $R^a$ is selected from hydrogen or (1-4C) alkyl;
B is a nucleobase or nucleobase analogue; and
one of $X_1$ and $X_2$ is selected from $(CR^aR^b)_x$ (where x is selected from 1 or 2) and the other is selected from CR$^a$R$^b$, O, NR$^c$ or S, wherein R$^a$ and R$^b$ are independently selected from hydrogen, (1-2C)alkyl, hydroxy, amino, halo or mercapto, and R$^c$ is selected from hydrogen or a (1-6C)alkyl; or one of X$_1$ and X$_2$ is O and the other is NR$^c$.

Suitably, Q$_1$ is selected from CH$_2$, CF$_2$, O or S, particularly O or S. In a particular embodiment, Q$_1$ is O.

Suitably, one of X$_1$ and X$_2$ is selected from O, NR$^c$ or S and the other of X$_1$ and X$_2$ is CH$_2$, wherein R$^c$ is selected from hydrogen or a (1-6C)alkyl.

In a particular embodiment, X$_1$ is CH$_2$ and X$_2$ is O.

In another embodiment, the oligonucleotide comprises one or more dinucleotide moieties of the formula:

Formula (II)

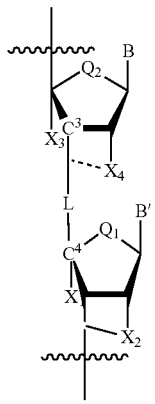

wherein:
C$^3$ is a 3' carbon;
C$^4$ is a 4' carbon;
Q$_1$ has any one of the definitions set out hereinbefore;
Q$_2$ is selected from CR$^p$R$^q$, O, S or NR$^a$, wherein R$^p$ and R$^q$ are each independently selected from H, (1-4C)alkyl or halo, and R$^a$ is selected from hydrogen or (1-4C) alkyl;
B and B' are each independently a nucleobase or nucleobase analogue;
X$_1$ and X$_2$ each have any one of the definitions set out hereinbefore;
one of X$_3$ and X$_4$ is (CR$^d$R$^e$)$_y$ (wherein y is selected from 1 or 2) and the other is CR$^d$R$^e$, O, NR$^f$ or S, wherein R$^d$ and R$^e$ are independently selected from hydrogen, (1-2C)alkyl, hydroxy, amino, halo or mercapto, and R$^f$ is selected from hydrogen or a (1-6C)alkyl; or one of X$_3$ and X$_4$ is O and the other is NR$^c$; or one of X$_3$ and X$_4$ is H and the other is selected from H, OH or NH$_2$; and L is triazole linking moiety as defined hereinbefore.

Suitably, Q$_2$ is selected from CH$_2$, CF$_2$, O or S, particularly O or S and most particularly O.

In an embodiment, one of X$_3$ and X$_4$ is H and the other is selected from H or OH. Suitably, X$_3$ and X$_4$ are both H.

In an alternative embodiment, one of X$_3$ and X$_4$ is selected from O, NR$^f$ or S and the other of X$_3$ and X$_4$ is CH$_2$, wherein R$^f$ is selected from hydrogen or a (1-6C)alkyl. Suitably, one of X$_3$ and X$_4$ is O, and the other of X$_3$ and X$_4$ is CH$_2$. Most suitably, X$_3$ is CH$_2$ and X$_4$ is O.

In a particular embodiment, the oligonucleotide comprises a dinucleotide moiety having one of the structural formulae shown below:

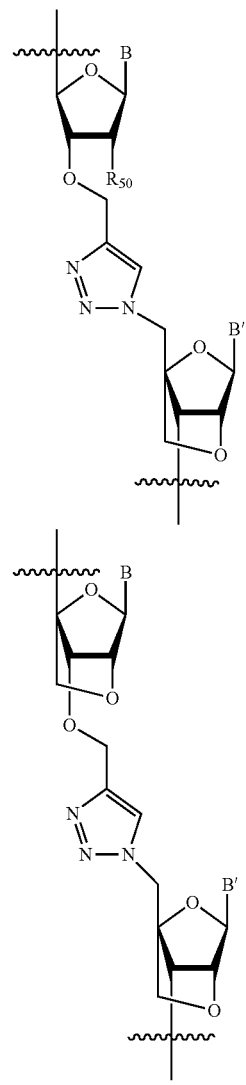

wherein B and B' are each independently a nucleobase and R$_{50}$ is H, OH, OCH$_3$ or F.

Suitably, R$_{50}$ is H or OH.

Synthesis

The oligonucleotides of the present invention can be prepared using techniques known in the art.

The preparation of oligonucleotides comprising one or more locked nucleosides in their sequence is known in the art. 16-19

Similarly, techniques to form triazole inter-nucleoside linker moieties by ligating two oligonucleotide strands, one bearing a terminal azide group and the other bearing a terminal alkyne group, are known in the art, see for example, U.S. Pat. No. 8,846,883, the entire contents of which are incorporated herein by reference.

Further examples of how to synthesize the oligonucleotides of the present invention are set out in the accompanying examples.

Uses and Applications

The oligonucleotides of the present invention may be used for a wide variety of applications in fields such as, for example, medicine, genetic testing, gene editing, diagnostics, agriculture, industrial biotechnology, biological research and forensics.

It will be appreciated that certain oligonucleotides of the present invention will have potential therapeutic applications. Examples include antisense RNA oligonucleotides of the present invention as well as certain siRNA and miRNA oligonucleotides.

Another example, is oligonucleotides associated with Clustered Regularly Interspaced Short Palindromic Repeats in combination with CRISPR Associated sequences (CRISPR-Cas) systems, such as for example CRISPR RNA (crRNA), pre-crRNA, tracrRNA and guideRNA (gRNA). Such oligonucleotides find therapeutic utility in the treatment of diseases via e.g. gene therapy as well as in the treatment of infections via selective killing of pathogenic organisms.

Thus, in one aspect, the present invention provides an oligonucleotide as defined herein for use in therapy. Examples of potential therapeutic uses of such oligonucleotides include the treatment of cancer, genetic disorders and infections.

The present invention further relates to the use of the oligonucleotides of the present invention as
(i) antisense RNA;
(ii) exon skipping RNA;
(iii) interference RNA (e.g. siRNA or miRNA) or
(iv) an RNA component of a CRISPR-Cas system.

In addition to potential therapeutic applications, the oligonucleotides of the present invention may also be used for a whole range of additional applications, such as, for example:
a template for amplification in a polymerase chain reaction (PCR);
as a template in a DNA replication process;
as a template in a transcription process to provide a corresponding RNA transcript, or as a template in a reverse transcription process to provide a corresponding DNA transcript;
as template in a translation process to produce a corresponding protein or peptide; or
to guide one or more proteins of interest to a target DNA or RNA.

Illustrative Examples of Oligonucleotides in CRISPR-Cas Systems

In general terms, there are two main classes of CRISPR-Cas systems (Makarova et al. *Nat Rev Microbiol.* 13:722-736 (2015)), which encompass five major types and 16 different subtypes based on cas gene content, cas operon architecture, Cas protein sequences, and process steps (Makarova et al. *Biol Direct.* 6:38 (2011); Makarova and Koonin *Methods Mol Biol.* 1311:47-75 (2015); Barrangou, R. *Genome Biology* 16:247 (2015)). This classification in either Class 1 or Class 2 is based upon the Cas genes involved in the interference stage.

Class 1 systems have a multi-subunit crRNA-effector complex such as Cascade-Cas3, whereas Class 2 systems have a crRNA-effector complex having a single Cas protein, such as Cas9, Cas12 (previously referred to as Cpf1) and Cas 13a (previously referred to as C2c2). For Type II systems there is a second RNA component tracrRNA which hybridises to crRNA to form a crRNA:tracr RNA duplex, these two RNA components may be linked to form single guide RNA.

RNA components in such CRISPR-Cas systems may be adapted to be an oligonucleotide in accordance with the invention. It would be a matter of routine for a person of ordinary skill in the art to synthesize a crRNA, pre-crRNA, tracrRNA or guideRNA having at least one inter-nucleoside linkage which is a triazole linker moiety between two nucleosides with a locked nucleoside positioned at the 3' end of the triazole linker moiety, and which retains the desired function of the RNA component (e.g., to guide the crRNA: effector complex to a target site). Standard methods are known in the art for testing whether oligonucleotides of the invention when used as such CRISPR RNA components retain the desired function (e.g. by comparing the desired function to that of a control CRISPR RNA component which has the same nucleosides without any-triazole linker moieties between nucleosides or locked nucleosides).

The term "CRISPR RNA components" or "RNA component of a CRISPR-Cas system" is used herein, as in most CRISPR-Cas systems, the nucleic acid sequences which guide the effector protein(s) to a desired target sequence are RNA components. However, CRISPR hybrid DNA/RNA polynucleotides which can also function to guide effector protein(s) to a desired target site in a DNA or RNA sequence are also known in the art—see for example Rueda et al. (Mapping the sugar dependency for rational generation of a DNA-RNA hybrid-guided Cas9 endonuclease, Nature Communications 8, Article Number: 1610 (2017)). Accordingly, reference to CRISPR RNA components herein may also encompass hybrid RNA/DNA components such as crDNA/RNA, tracrDNA/RNA or gDNA/RNA.

Advantageously the oligonucleotides of the invention may have particular utility in in vivo gene therapy applications. For example, one way of carrying out in vivo therapy using a Type II CRISPR-Cas system involves delivering the Cas9 and tracrRNA via a virus, which can assemble inactive complexes inside of cells. The crRNA can then be administered later to assemble and selectively activate CRISPR/Cas9 complexes, which would then go on to target and edit specific sites in the human genome, such as disease relevant genes (Gagnon and Corey, Proc. Natl. Acad. Sci. USA 112:15536-15537, 2015; Randar, et al, Proc. Natl. Acad. Sci. USA 112:E7110-7117, 2015). For this gene therapy approach to work the crRNA should be extremely resistant to nucleases and cellular degradation, as well as confer high activity and specificity to the assembled CRISPR/Cas9 complex. Hence, the increased stability of the oligonucleotides of the invention to degradation is highly desirable. Alternatively, crRNA:effector complexes (i.e. CRISPR-Cas complexes, such as CRISPR/Cas9) can be assembled in vitro and directly transfected into cells for genome editing (Liang, et al, J. Biotechnol. 208:44-53, 2015; Zuris, et al, Nat. Biotechnol. 33:73-80, 2015). Special transfection reagents, such as CRISPRMAX (Yu, et al, Biotechnol. Lett. 38:919-929, 2016), have been developed for this purpose. Oligonucleotides of the invention when used as crRNAs may improve this approach by offering stability against degradation.

Accordingly, the oligonucleotides of the invention when used as CRISPR RNA components can advantageously be used for the various applications of CRISPR-Cas systems known in the art including: gene-editing, gene activation (CRISPRa) or gene interference (CRISPRi), base-editing, multiplex engineering (CRISPRm), DNA amplification, diagnostics (e.g. SHERLOCK or DETECTR), cell recording (e.g. CAMERA), typing bacteria, antimicrobial applications, synthesising new chemicals etc.

Suitably, in diagnostic applications such as SHERLOCK and DETECTR the oligonucleotides of the invention can be used as RNA components such as the "sacrificial RNA molecules" used to create a signal.

EXAMPLES

In this section, ON is an abbreviation for oligonucleotide.

Figure 1:
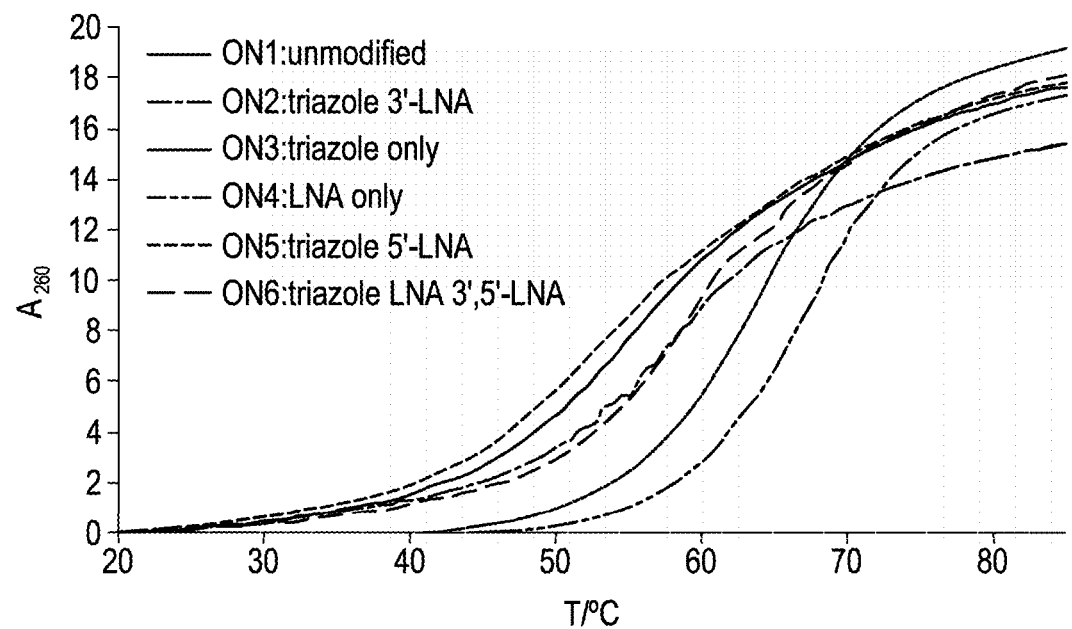
FIG. 1 shows representative melting curves for duplexes containing a single triazole linkage (MeC-T step, left against DNA target and right against RNA target). For sequences see Table 5.
Figure 1:
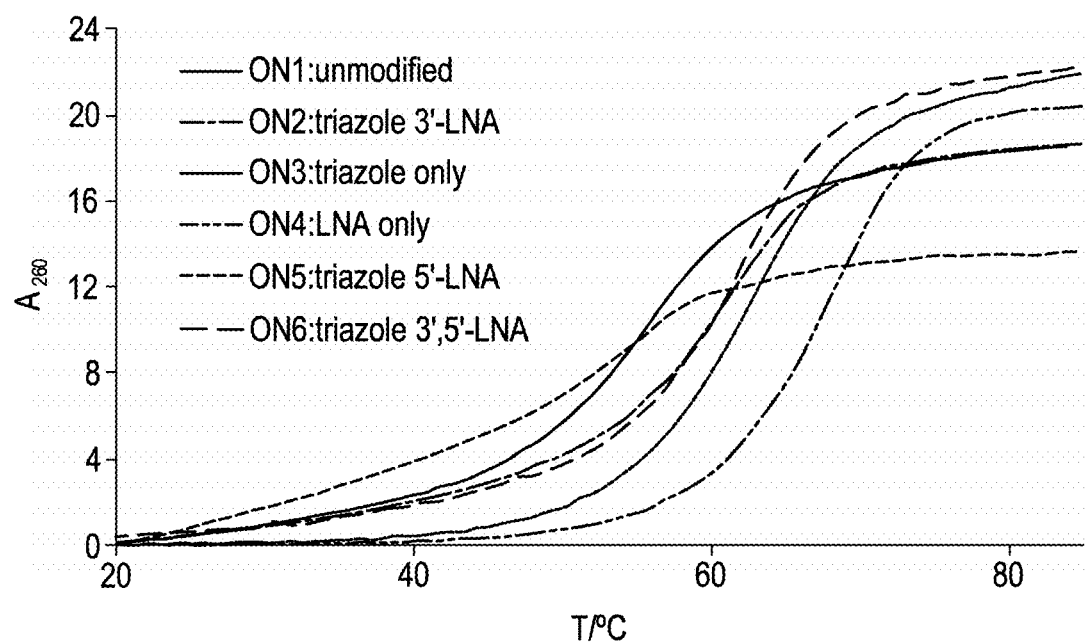

Embodiments of the invention will be described, by way of example only, with reference to the accompanying drawings, in which:

FIG. 1 shows representative melting curves for duplexes containing a single triazole linkage (MeC-T step, left against DNA target and right against RNA target). For sequences see Table 5.

Figure 2:
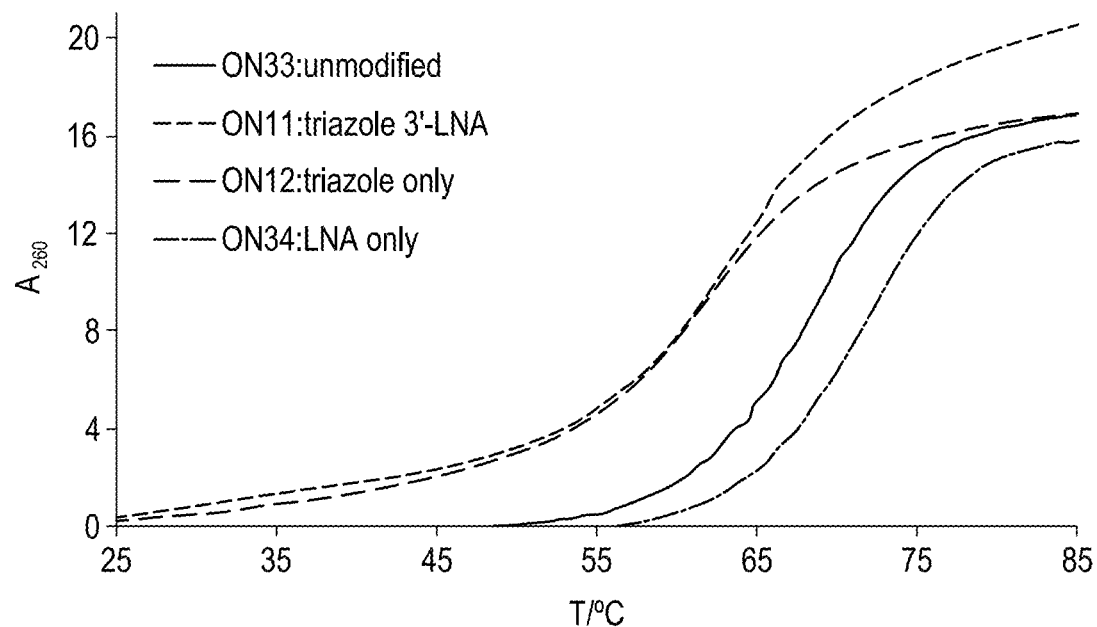
FIG. 2 shows representative melting curves for duplexes containing a single triazole linkage (MeC-MeC step, left against DNA target and right against RNA target). For sequences see Table 1.
Figure 2:
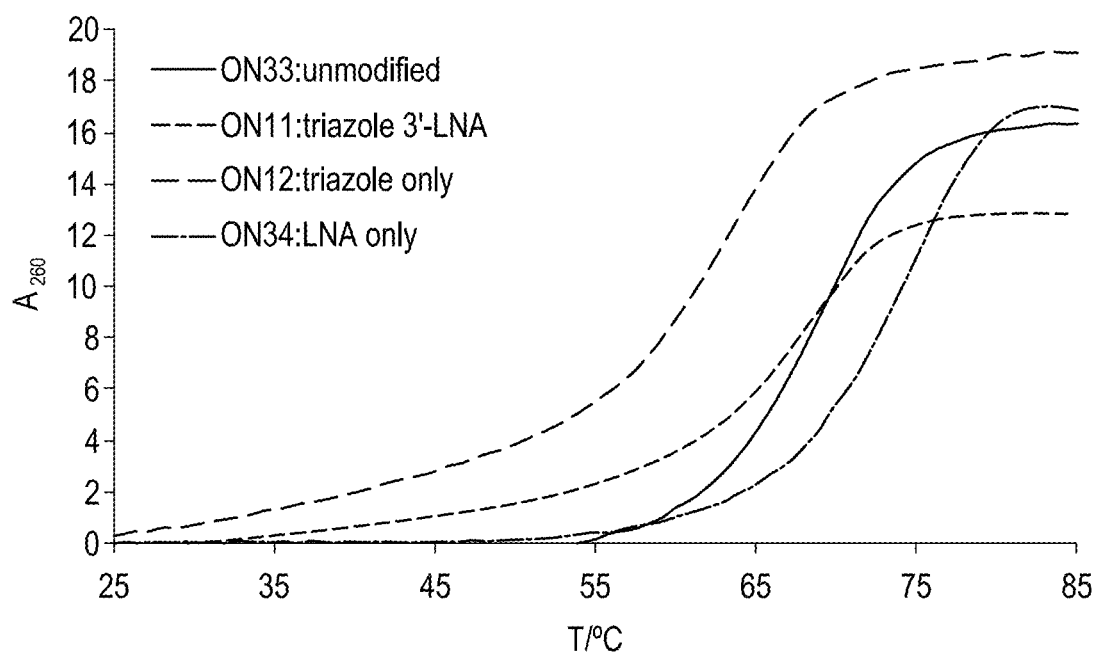

FIG. 2 shows representative melting curves for duplexes containing a single triazole linkage (MeC-MeC step, left against DNA target and right against RNA target). For sequences see Table 1.

Figure 3:
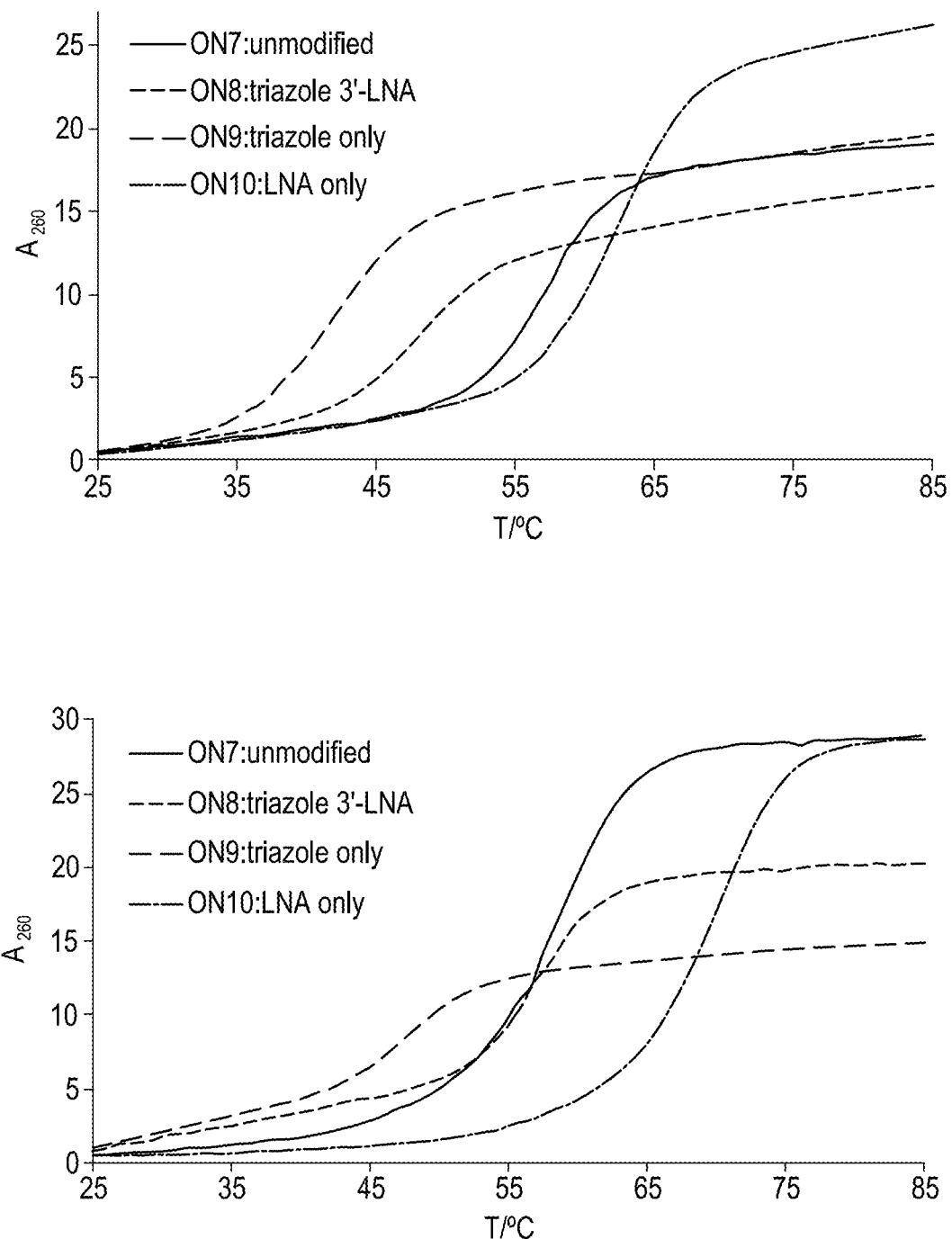
FIG. 3 shows representative melting curves for duplexes incorporating two triazole linkages (MeC-T steps, left against DNA target and right against RNA target). For sequences see Table 6.

FIG. 3 shows representative melting curves for duplexes incorporating two triazole linkages (MeC-T steps, left against DNA target and right against RNA target). For sequences see Table 6.

Figure 4:
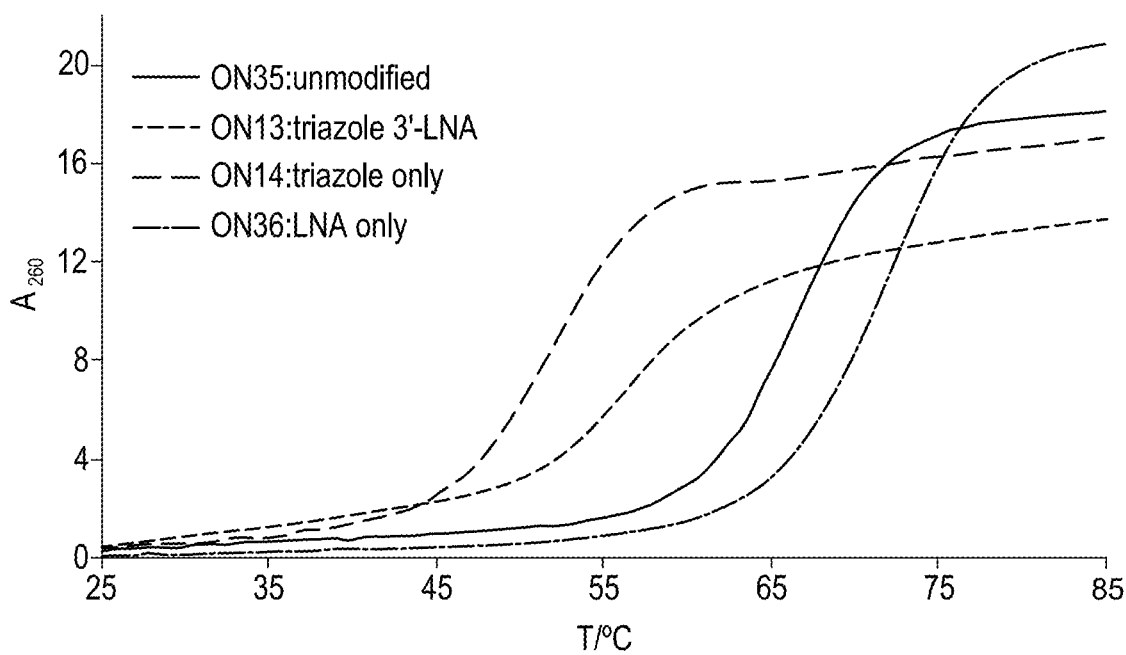
FIG. 4 shows representative melting curves for duplexes incorporating two triazole linkages (MeC-MeC steps, left against DNA target and right against RNA target). For sequences see Table 4.
Figure 4:
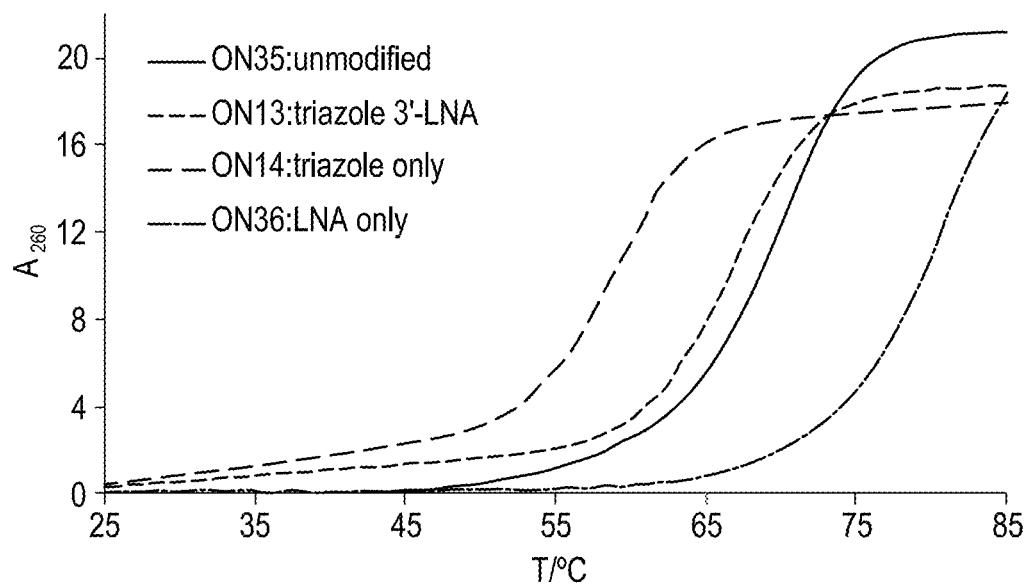

FIG. 4 shows representative melting curves for duplexes incorporating two triazole linkages (MeC-MeC steps, left against DNA target and right against RNA target). For sequences see Table 4.

Figure 5:
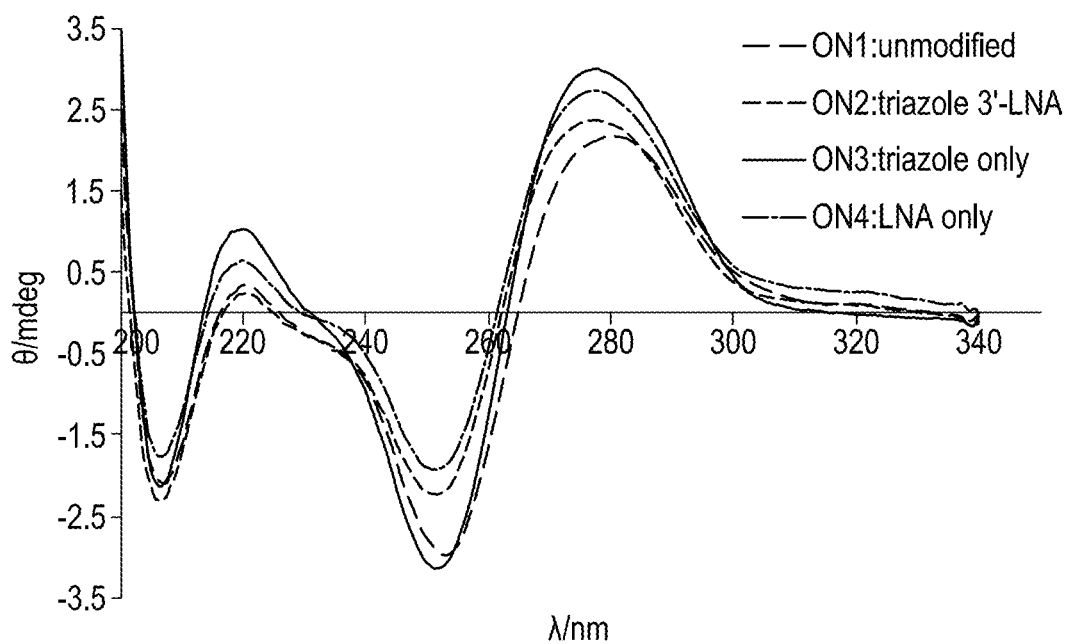
FIG. 5 shows representative CD curves for duplexes containing a single triazole linkage (MeC-T step, left against DNA target; right against RNA target). For sequences see Table 5.
Figure 5:
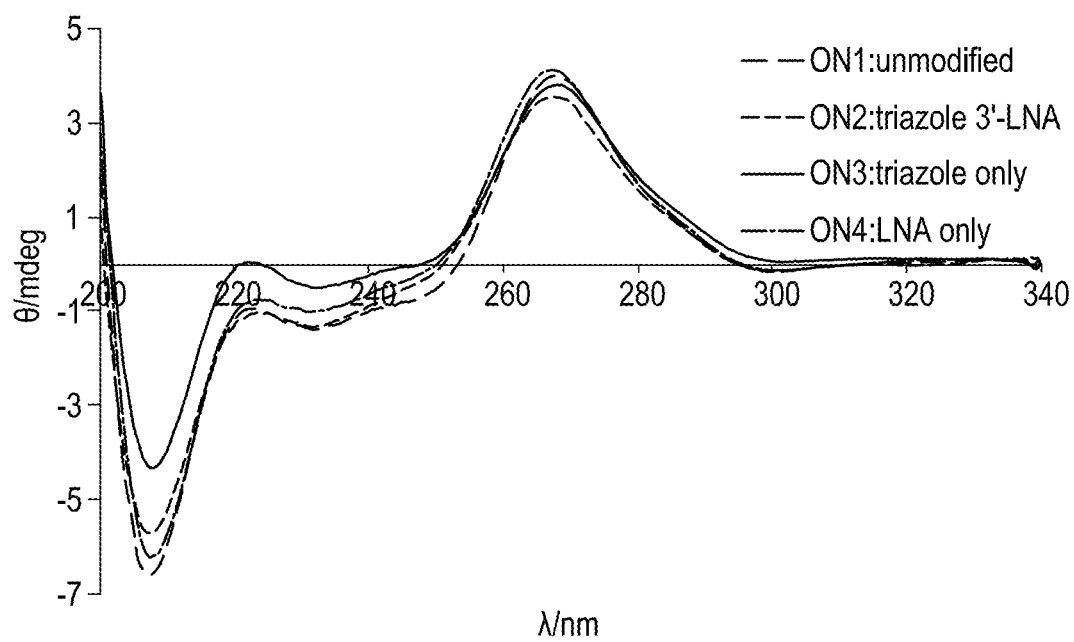

FIG. 5 shows representative CD curves for duplexes containing a single triazole linkage (MeC-T step, left against DNA target; right against RNA target). For sequences see Table 5.

Figure 6:
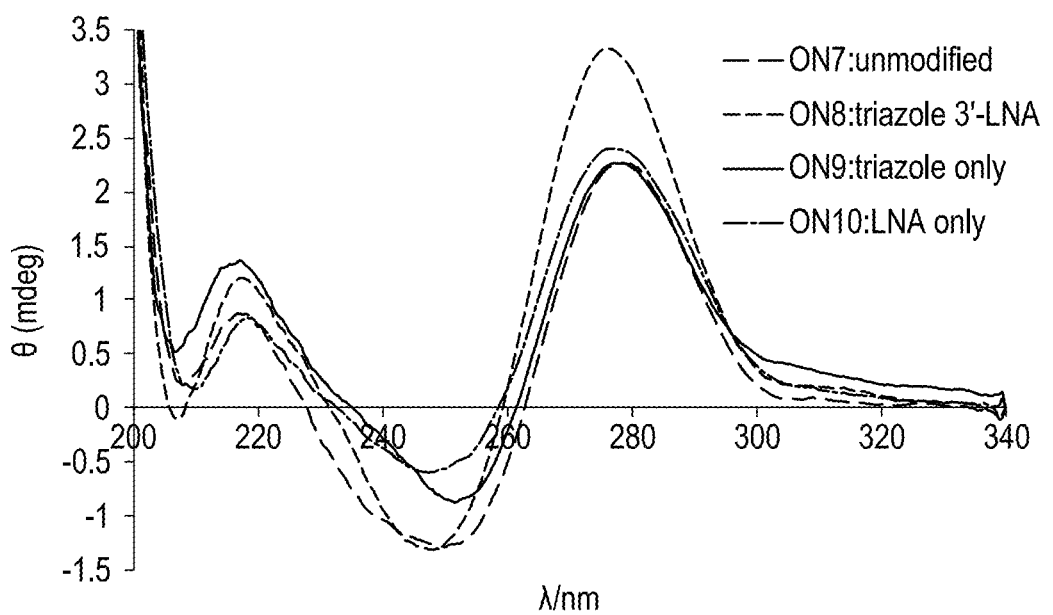
FIG. 6 shows representative CD curves for duplexes incorporating two triazole linkages (MeC-T step, left against DNA target; right against RNA target). For sequences see Table 6.
Figure 6:
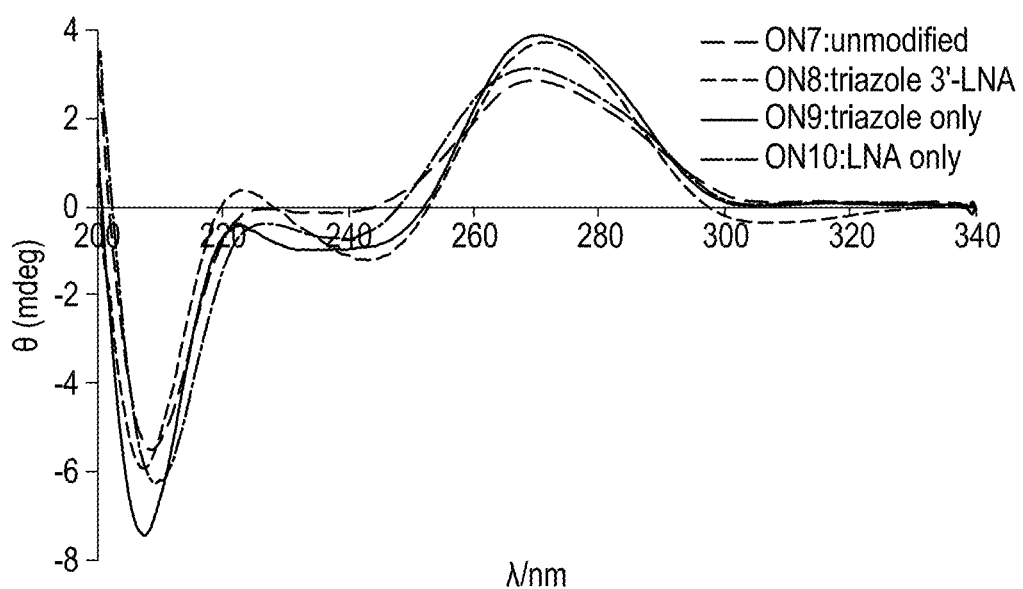

FIG. 6 shows representative CD curves for duplexes incorporating two triazole linkages (MeC-T step, left against DNA target; right against RNA target). For sequences see Table 6.

Figure 7:
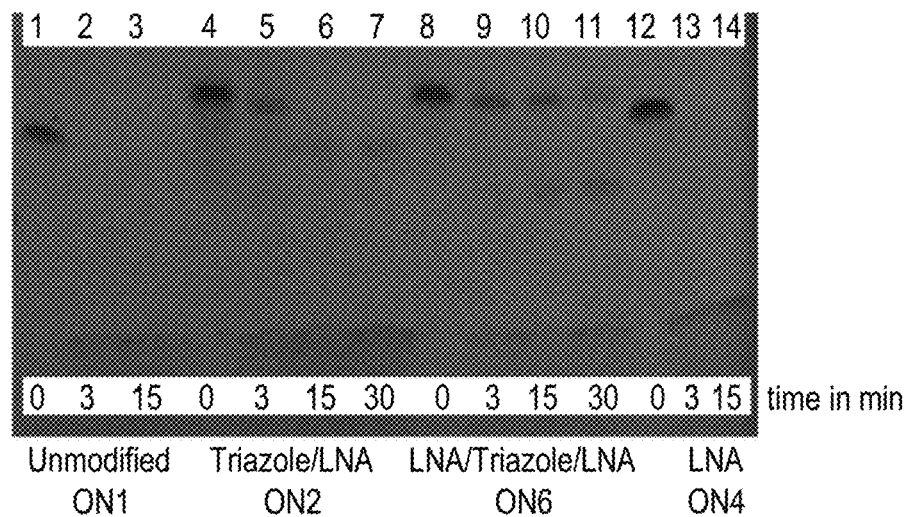
FIG. 7 shows LNA triazole stabilises oligonucleotides to 3'-exonuclease digestion. The ON1: unmodified (lanes 1-3) and ON2: triazole 3'-LNA (lanes 4-7), ON6: triazole 3',5'-LNA (lanes 8-11), ON4: LNA only (lane 12-14).

FIG. 7 shows LNA triazole stabilises oligonucleotides to 3'-exonuclease digestion. The ON1: unmodified (lanes 1-3) and ON2: triazole 3'-LNA (lanes 4-7), ON6: triazole 3',5'-LNA (lanes 8-11), ON4: LNA only (lane 12-14).

Figure 8:
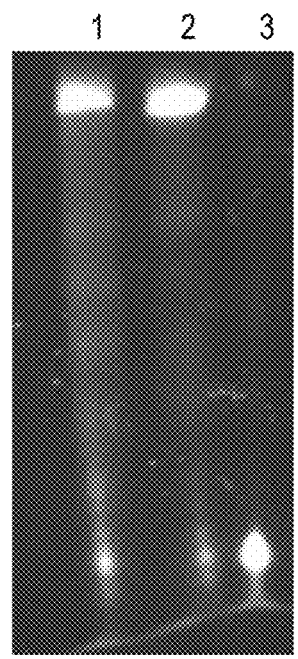
FIG. 8 shows the 10% denaturing polyacrylamide gel from linear copying reaction. Lane 1; Linear copying reaction using modified template (ON15) 5'-dGCA TTC GAG CAA CGT AAG ATC G$^{Me}$Ct$^L$ AGC ACA CAA TCT CAC ACT CTG GAA TTC ACA CTG ACA ATA CTG CCG ACA CAC ATA ACC (SEQ ID NO: 1) where represent triazole linkage and T$^L$ is LNA thymidine. Lane 2; Linear copying reaction using unmodified template 5'-dACGT-TAGCACGAAGAGGCATCTTAGCACACAATCT-CACACTCTGGAATTCACACTG ACAATACTCGCGAACACACCCAAT (SEQ ID NO: 2). Lane 3; negative control: linear copying reaction using modified template without enzyme. For modified template: Full length product mass; found 26025, calc. 26025. A relatively small peak at 26337 (full length+A) was also observed. For unmodified template: Full length product mass; found 25695, calc. 25695. No M+A product was observed for control. Primer used: 5'-dFTGGT-TATGTGTGTCGGCAG (SEQ ID NO: 3) (for modified template), 5'-dFTATTGGGTGTGTTCGCGAG (SEQ ID NO: 4) (for unmodified template), F is amidohexylfuorescein.

FIG. 8 shows the 10% denaturing polyacrylamide gel from linear copying reaction. Lane 1; Linear copying reaction using modified template (ON15) 5'-dGCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 1) where represent triazole linkage and T$^L$ is LNA thymidine. Lane 2; Linear copying reaction using unmodified template 5'-dACGTTAGCACGAAGAGGCATCT-TAGCACACAATCTCACACTCTGGAATTCACACTG ACAATACTCGCGAACACACCCAAT (SEQ ID NO: 2). Lane 3; negative control: linear copying reaction using modified template without enzyme. For modified template: Full length product mass; found 26025, calc. 26025. A relatively small peak at 26337 (full length+A) was also observed. For unmodified template: Full length product mass; found 25695, calc. 25695. No M+A product was observed for control. Primer used: 5'-dFTGGT-TATGTGTGTCGGCAG (SEQ ID NO: 3) (for modified template), 5'-dFTATTGGGTGTGTTCGCGAG (SEQ ID NO: 4) (for unmodified template), F is amidohexylfluorescein.

Figure 9:
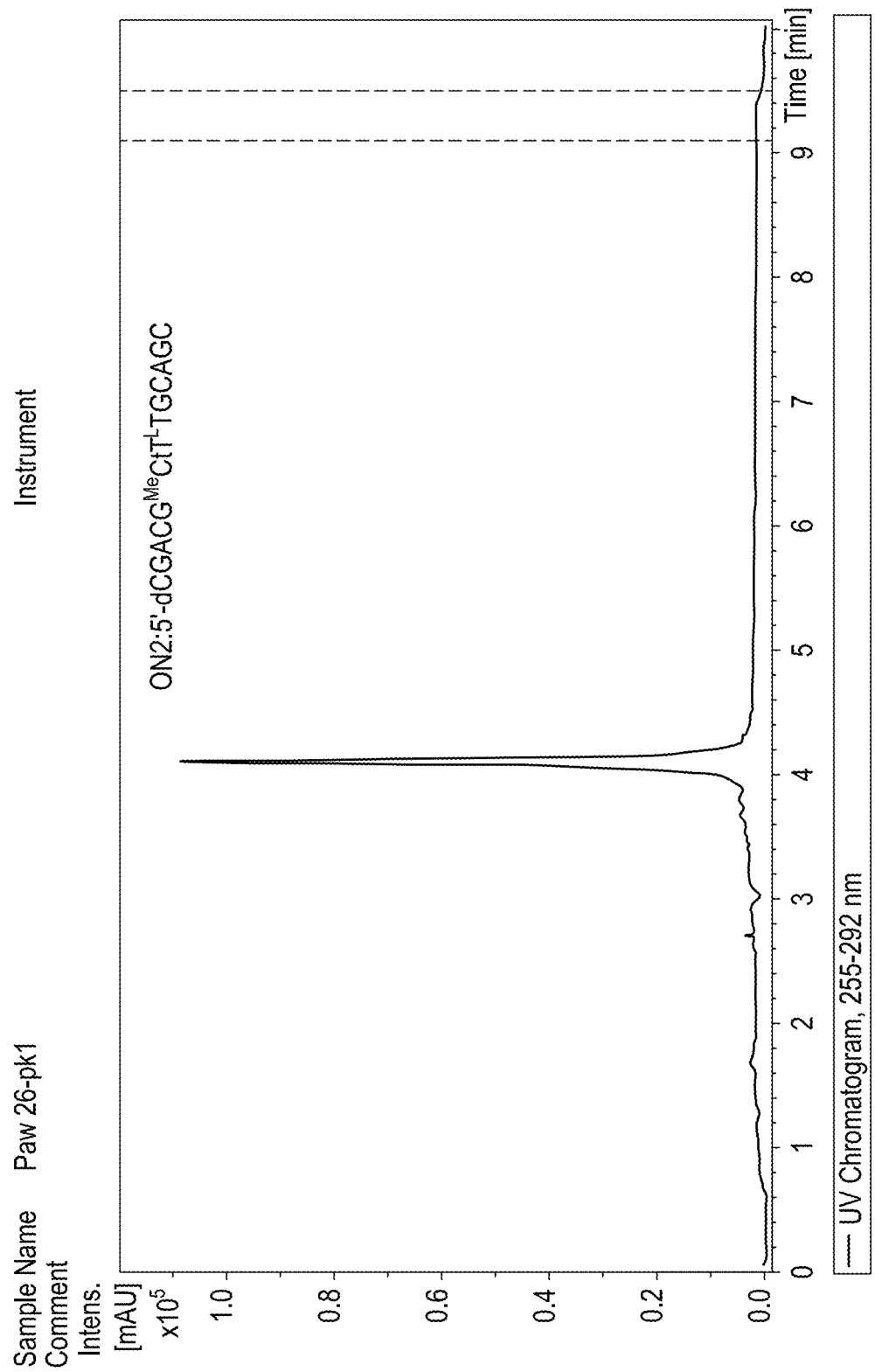
FIG. 9 shows the UV trace from HPLC of HPLC/mass spec for modified oligonucleotide ON2: 5'-dCGACG $^{Me}$C-tT$^L$TGCAGC (SEQ ID NO: 5).

FIG. 9 shows the UV trace from HPLC of HPLC/mass spec for modified oligonucleotide ON2: 5'-dCGACG $^{Me}$Ct-T$^L$TGCAGC (SEQ ID NO: 5).

Figure 10:
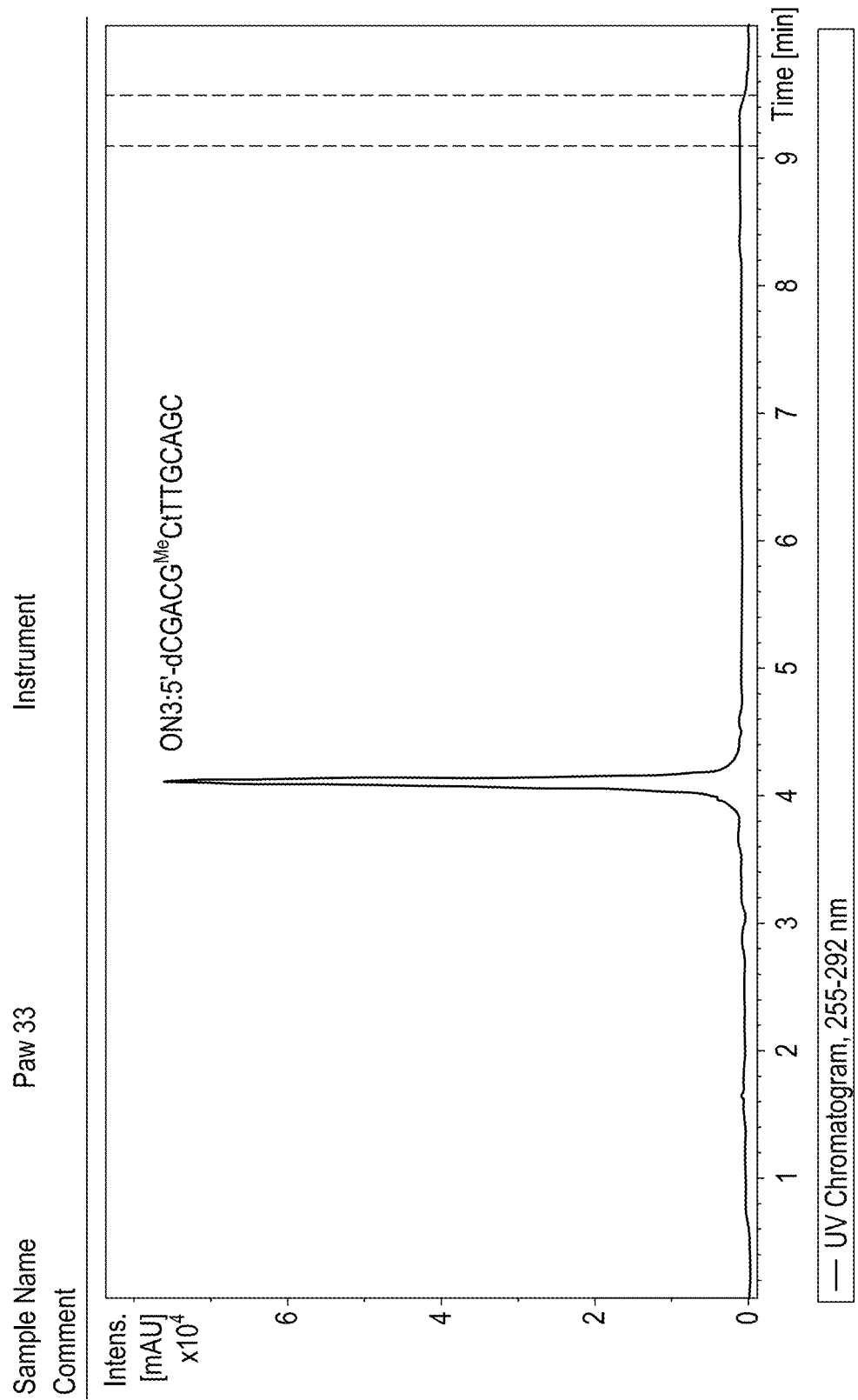
FIG. 10 shows the UV trace from HPLC of HPLC/mass spec for modified oligonucleotide ON3: 5'-dCGACG $^{Me}$C-tTTGCAGC (SEQ ID NO: 6).

FIG. 10 shows the UV trace from HPLC of HPLC/mass spec for modified oligonucleotide ON3: 5'-dCGACG $^{Me}$C-tTTGCAGC (SEQ ID NO: 6).

Figure 11:
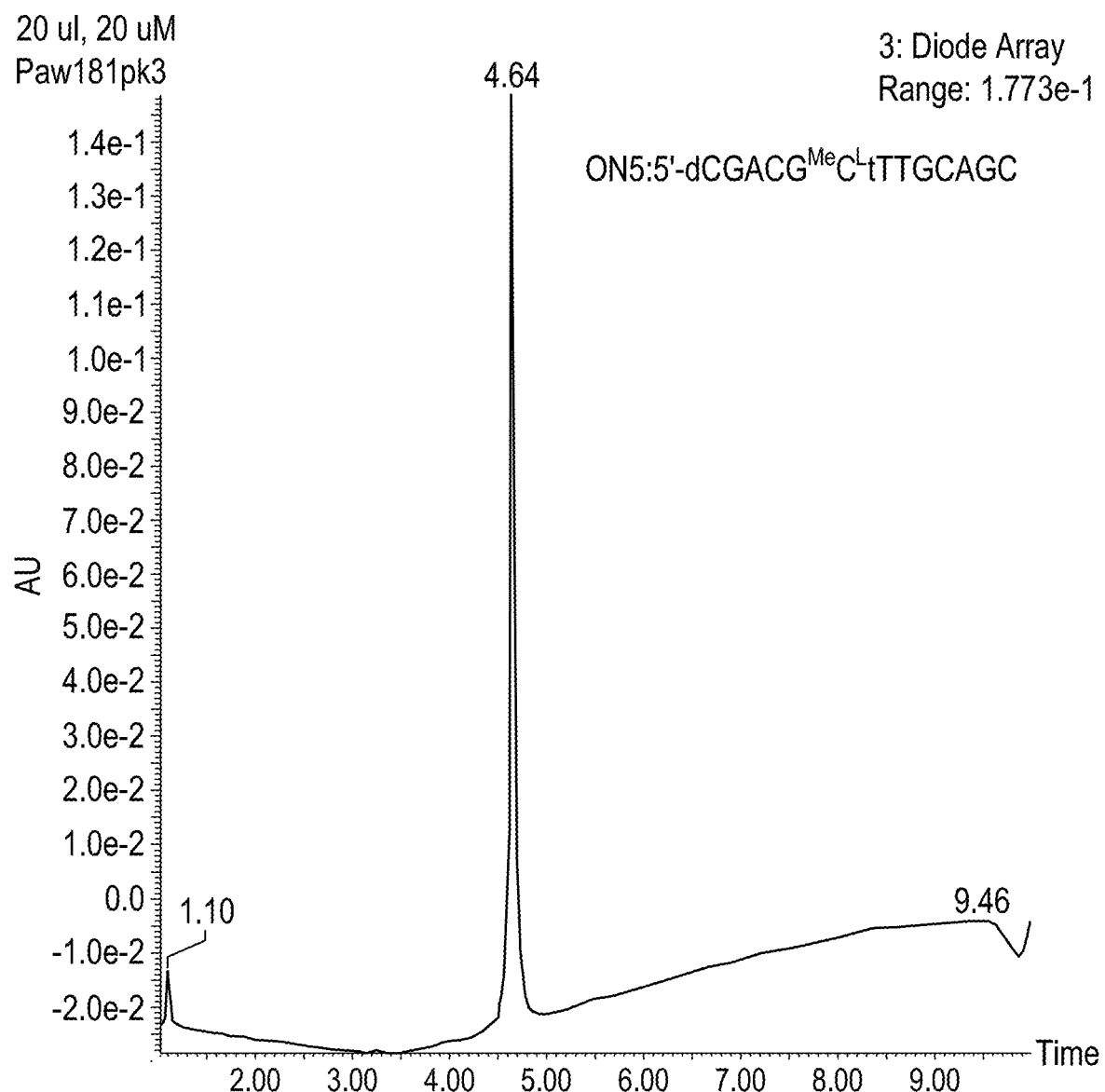
FIG. 11 shows the UV trace from HPLC of HPLC/mass spec for modified oligonucleotide ON5: 5'-dCGACG $^{Me}$C$^L$tTTGCAGC (SEQ ID NO: 7).

FIG. 11 shows the UV trace from HPLC of HPLC/mass spec for modified oligonucleotide ON5: 5'-dCGACG $^{Me}$C$^L$tTTGCAGC (SEQ ID NO: 7).

Figure 12:
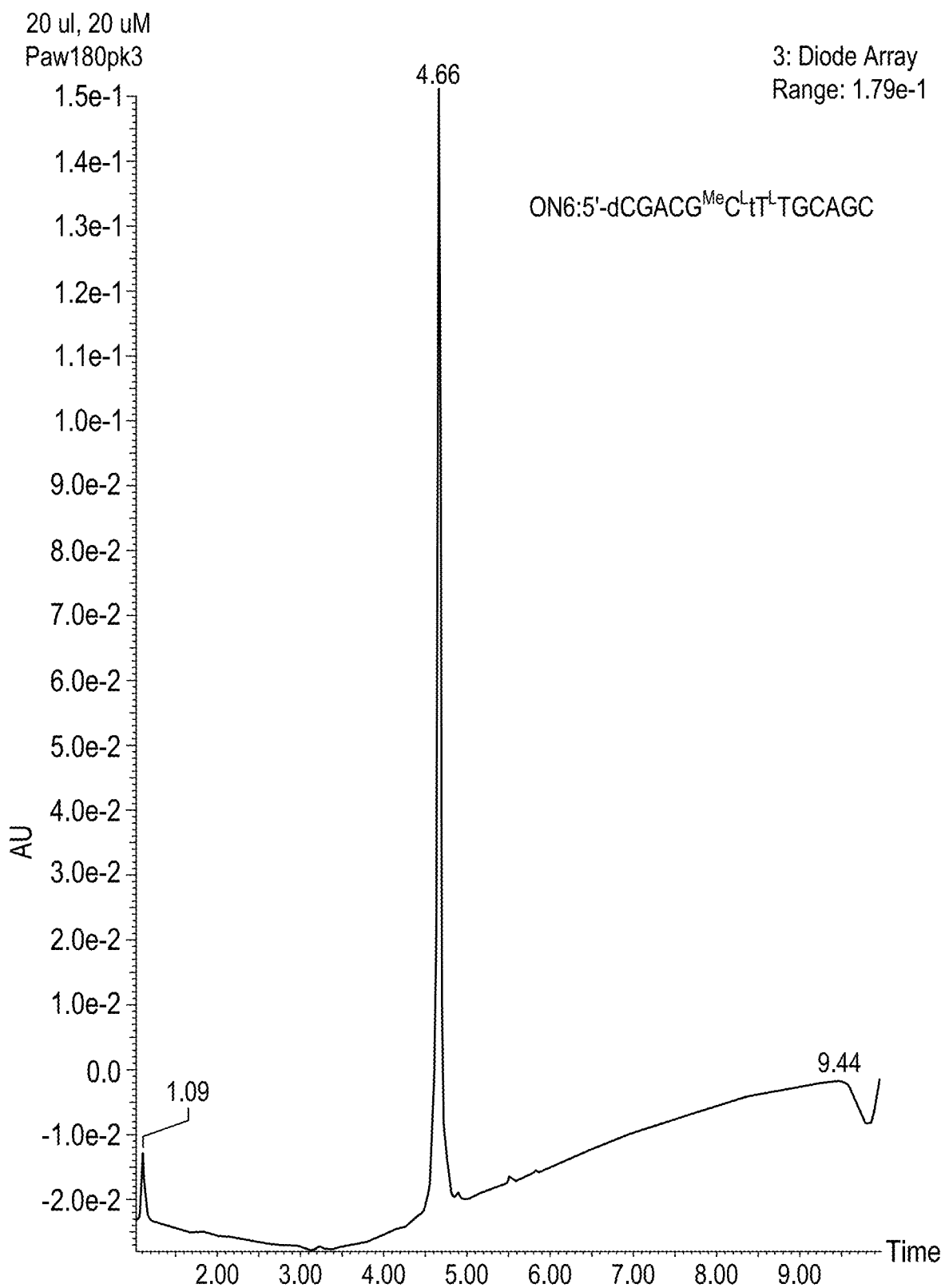
FIG. 12 shows the UV trace from HPLC of HPLC/mass spec for modified oligonucleotide ON6: 5'-dCGACG $^{Me}$C$^L$t-T$^L$TGCAGC (SEQ ID NO: 8).

FIG. 12 shows the UV trace from HPLC of HPLC/mass spec for modified oligonucleotide ON6: 5'-dCGACG $^{Me}$C$^L$t-TLTGCAGC (SEQ ID NO: 8).

Figure 13:
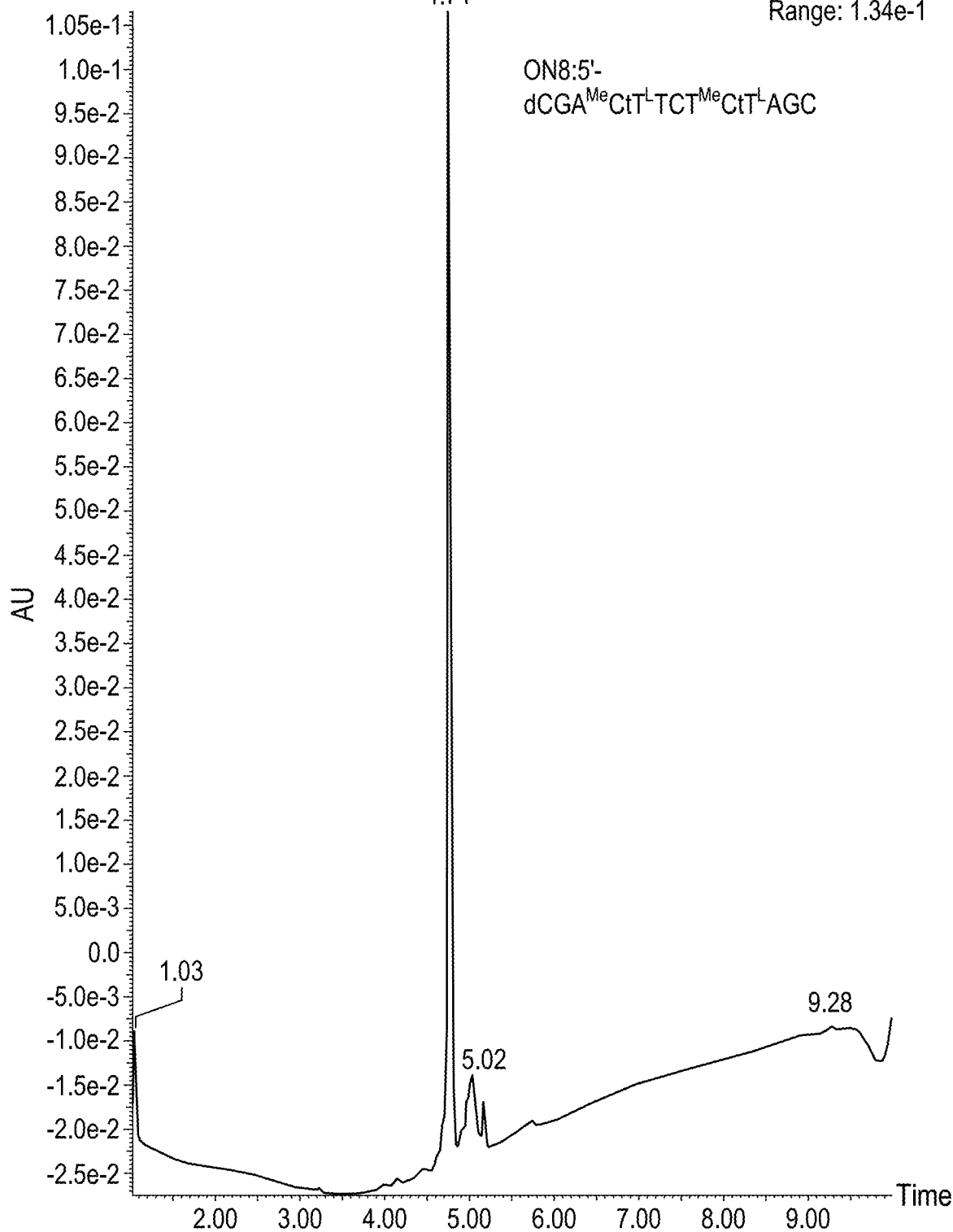
FIG. 13 shows the UV trace from HPLC of HPLC/mass spec for modified oligonucleotide ON8: 5'-dCGA$^{Me}$Ct-T$^L$TCT$^{Me}$CtT$^L$AGC (SEQ ID NO: 9).

FIG. 13 shows the UV trace from HPLC of HPLC/mass spec for modified oligonucleotide ON8: 5'-dCGA$^{Me}$CtT$^L$TCT$^{Me}$CtT$^L$AGC (SEQ ID NO: 9).

Figure 14:
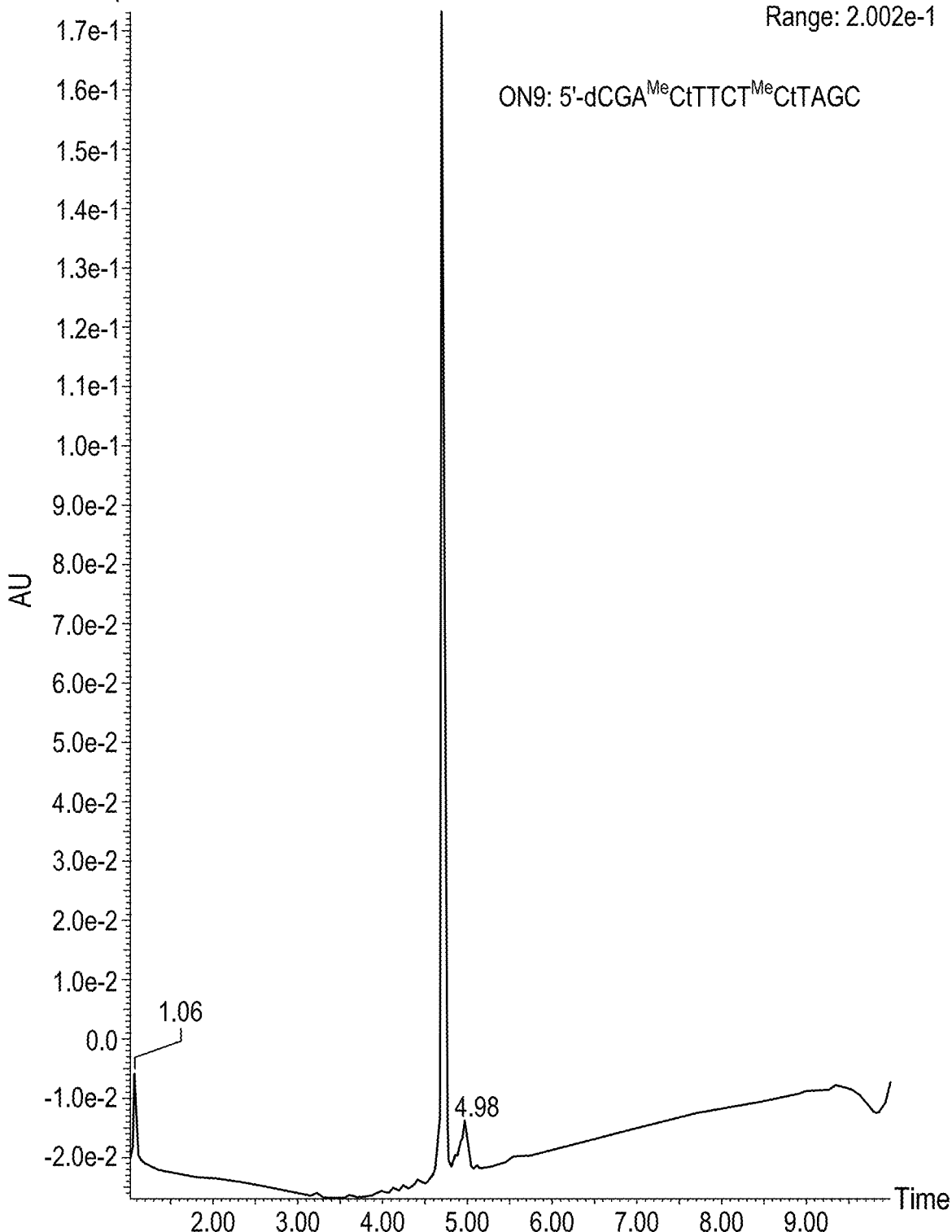
FIG. 14 shows the UV trace from HPLC of HPLC/mass spec for modified oligonucleotide ON9: 5'-dCGA$^{Me}$C-tTTCT$^{Me}$CtTAGC (SEQ ID NO: 10).

FIG. 14 shows the UV trace from HPLC of HPLC/mass spec for modified oligonucleotide ON9: 5'-dCGA$^{Me}$CtTTCT$^{Me}$CtTAGC (SEQ ID NO: 10).

Figure 15:
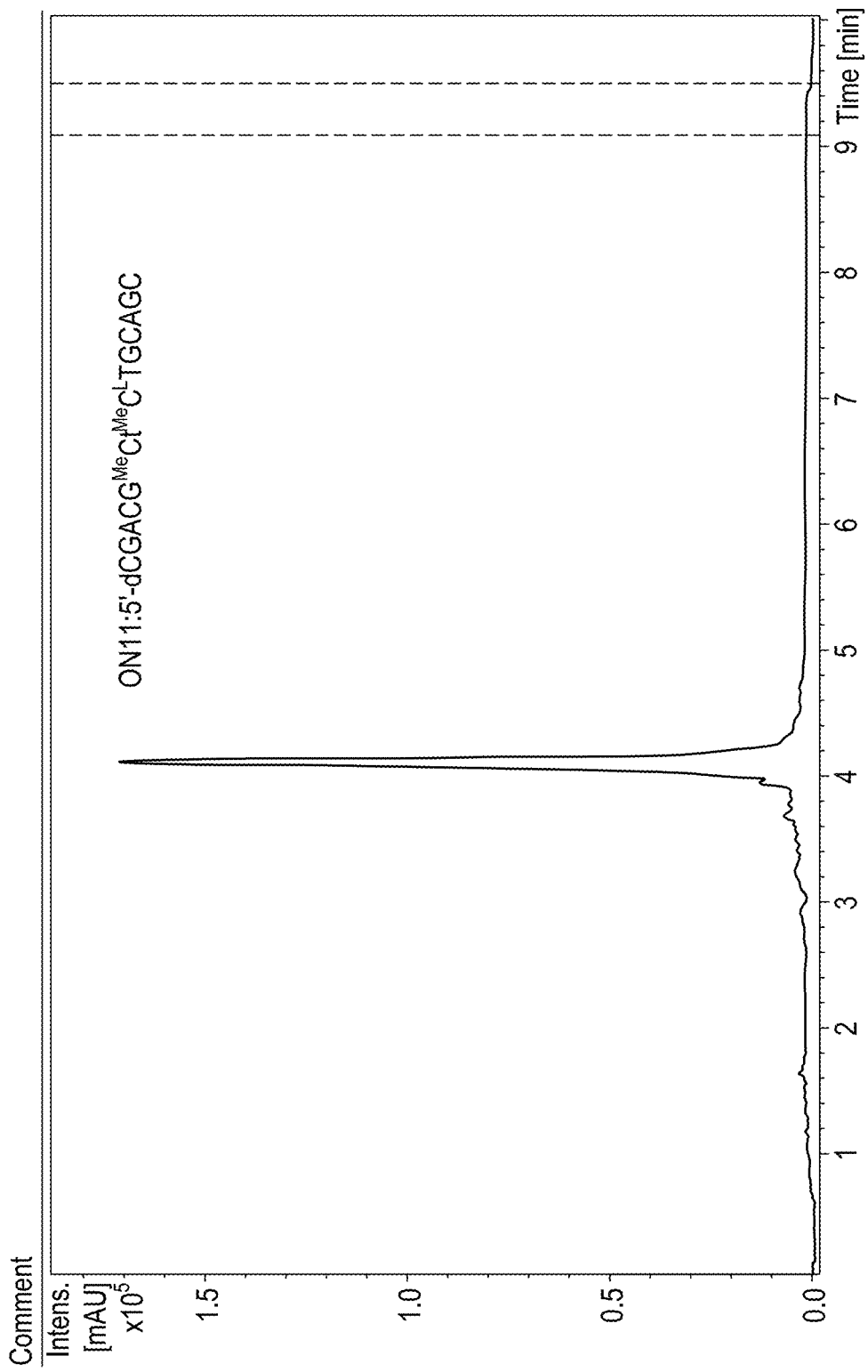
FIG. 15 shows the UV trace from HPLC of HPLC/mass spec for modified oligonucleotide ON11: 5'-dCGACG $^{Me}$C-t$^{Me}$C$^L$TGCAGC (SEQ ID NO: 11).

FIG. 15 shows the UV trace from HPLC of HPLC/mass spec for modified oligonucleotide ON11: 5'-dCGACG $^{Me}$Ct$^{Me}$CLTGCAGC (SEQ ID NO: 11).

Figure 16:
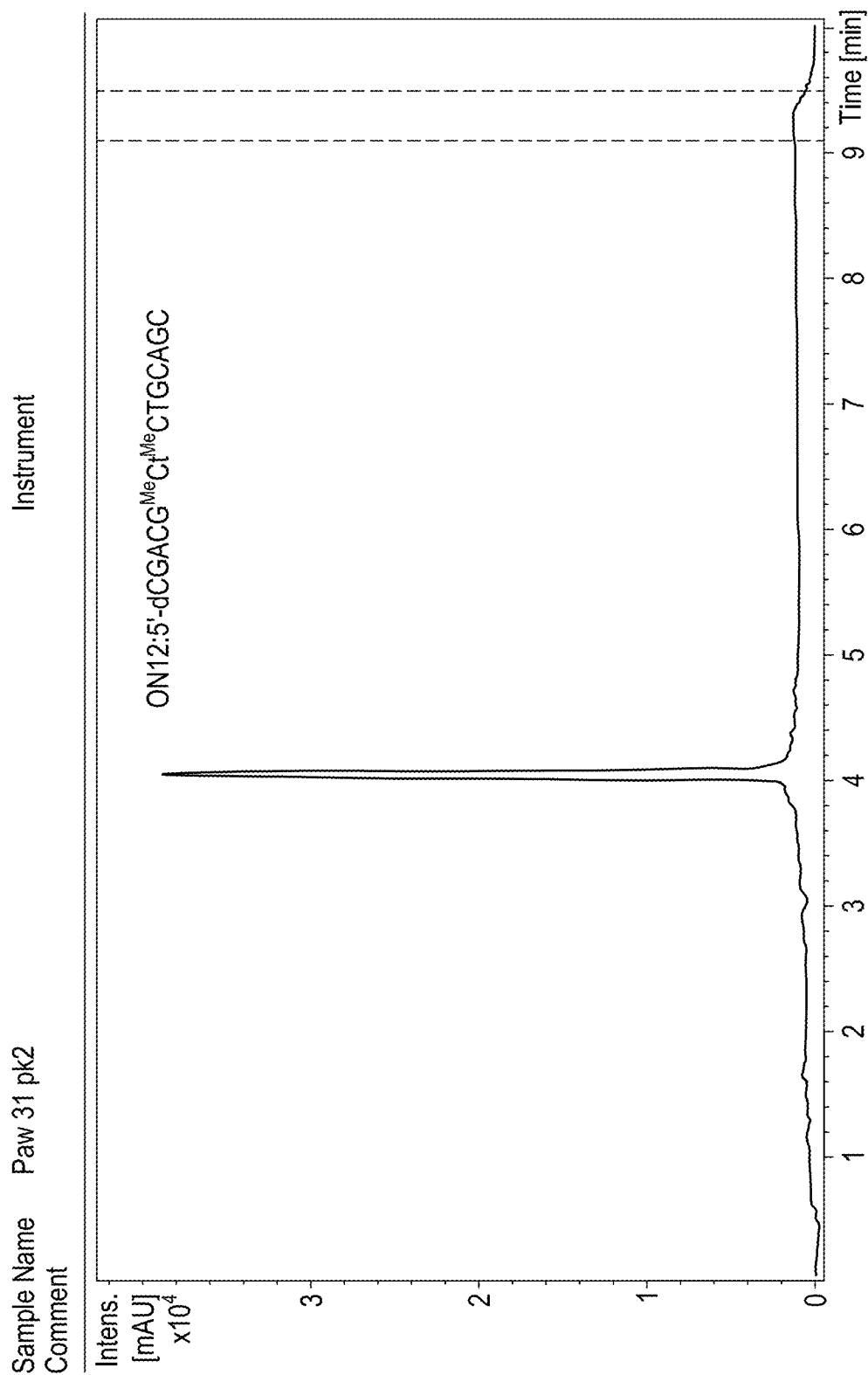
FIG. 16 shows the UV trace from HPLC of HPLC/mass spec for modified oligonucleotide ON12:'-dCGACG $^{Me}$Ct$^{Me}$CTGCAGC (SEQ ID NO: 12).

FIG. 16 shows the UV trace from HPLC of HPLC/mass spec for modified oligonucleotide ON12: 5'-dCGACG $^{Me}$Ct$^{Me}$CTGCAGC (SEQ ID NO: 12).

Figure 17:
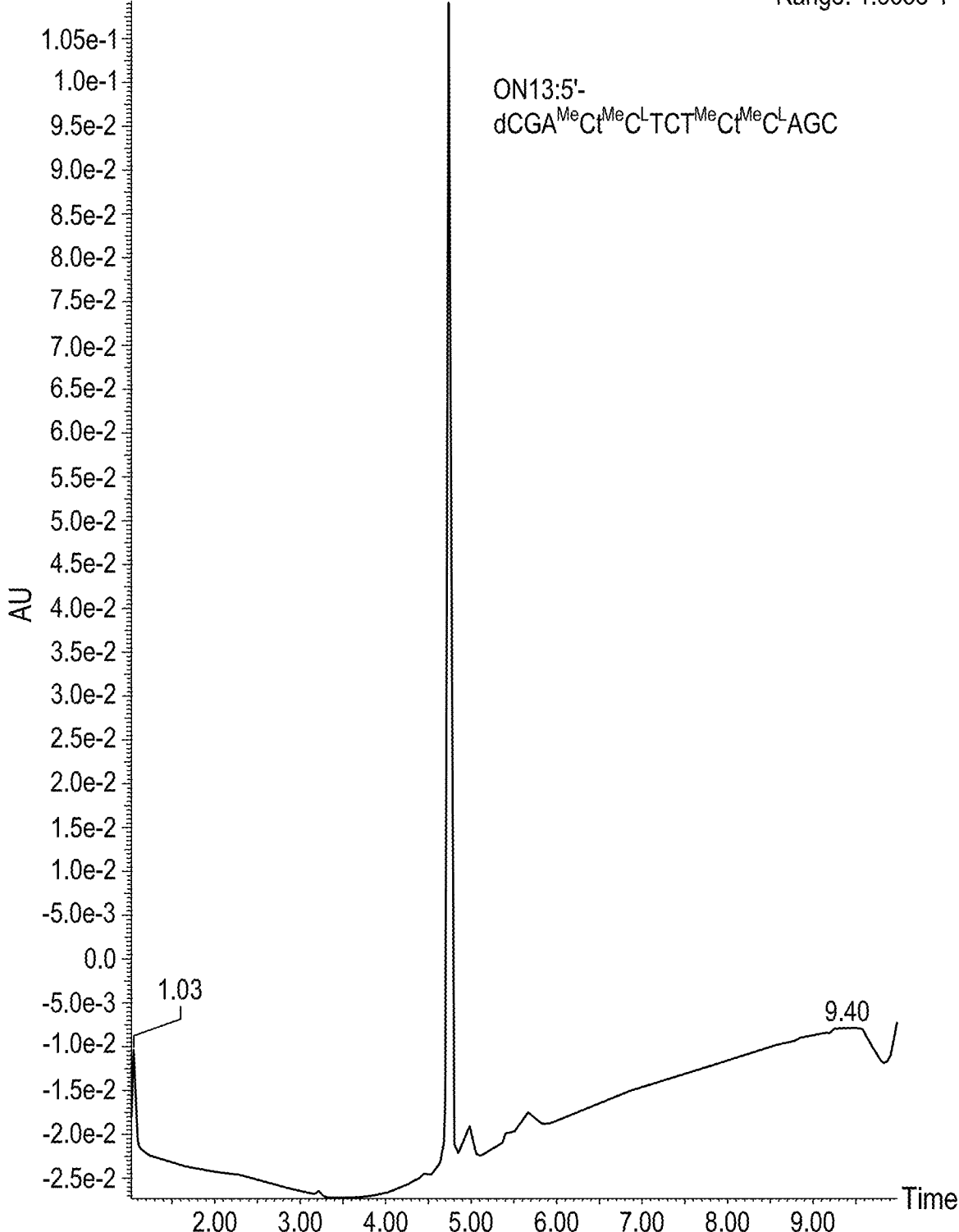
FIG. 17 shows the UV trace from HPLC of HPLC/mass spec for modified oligonucleotide ON13: 5'-dCGA$^{Me}$Ct$^{Me}$-C$^L$TCT$^{Me}$Ct$^{Me}$C$^L$AGC (SEQ ID NO: 13).

FIG. 17 shows the UV trace from HPLC of HPLC/mass spec for modified oligonucleotide ON13: 5'-dCGA$^{Me}$Ct$^{Me}$C$^L$TCT$^{Me}$Ct$^{Me}$C$^L$AGC (SEQ ID NO: 13).

Figure 18:
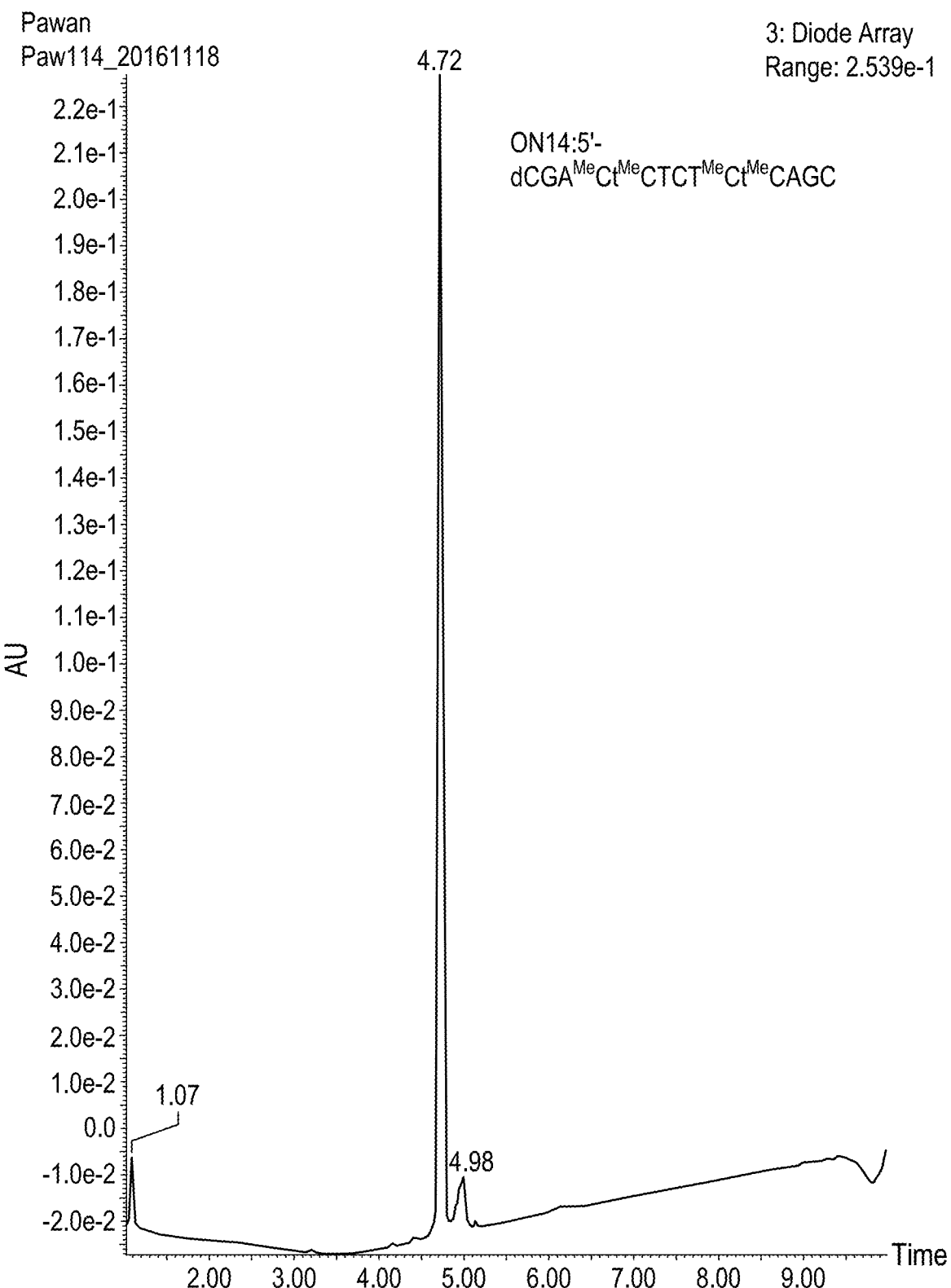
FIG. 18 shows the UV trace from HPLC of HPLC/mass spec for modified oligonucleotide ON14: 5'-dCGA$^{Me}$Ct$^{Me}$C-TCT$^{Me}$Ct$^{Me}$CAGC (SEQ ID NO: 14).

FIG. 18 shows the UV trace from HPLC of HPLC/mass spec for modified oligonucleotide ON14: 5'-dCGA$^{Me}$Ct$^{Me}$C-TCT$^{Me}$Ct$^{Me}$CAGC (SEQ ID NO: 14).

Figure 19:
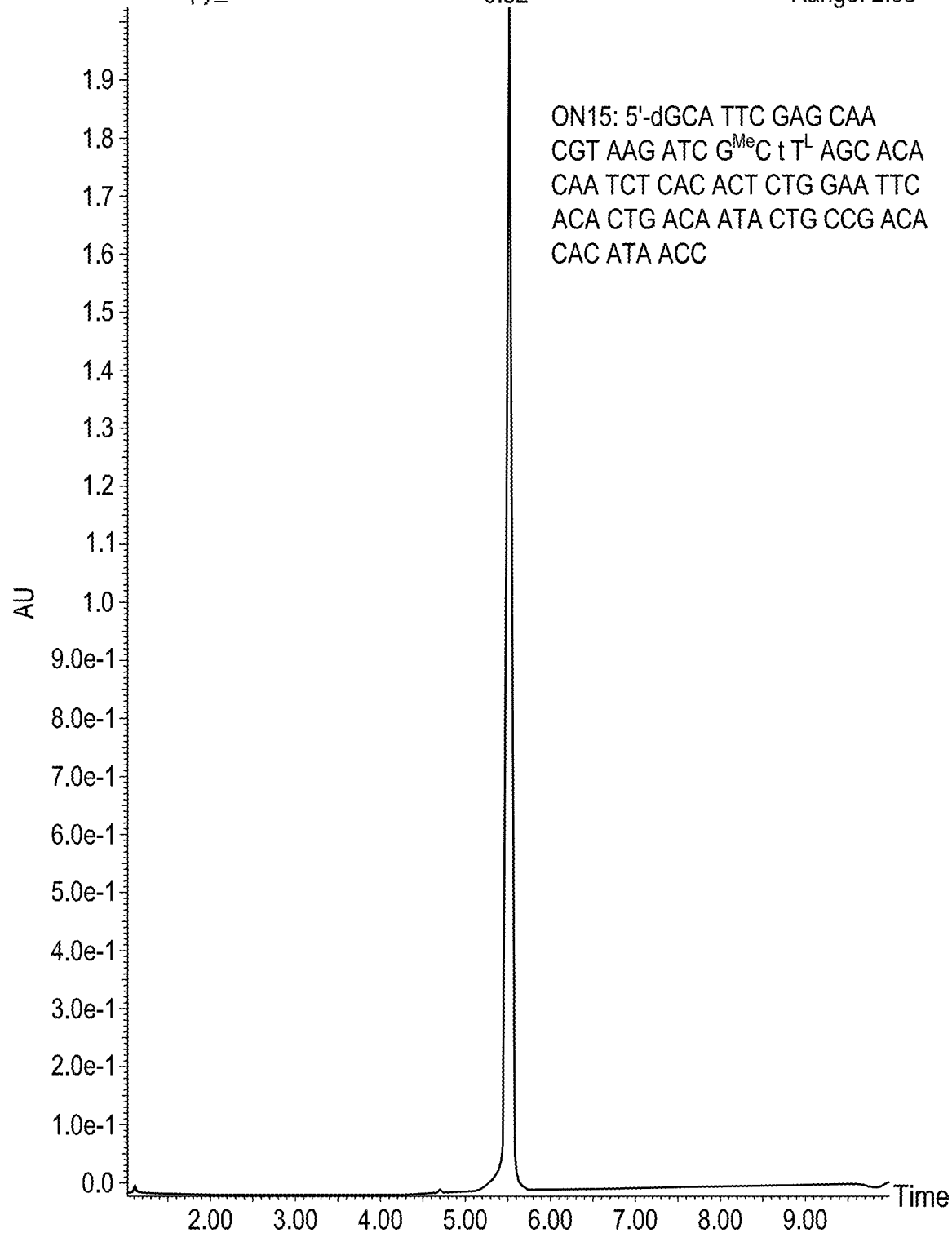
FIG. 19 shows the UV trace from HPLC of HPLC/mass spec for modified oligonucleotide ON15: 5'-dGCA TTC GAG CAA CGT AAG ATC G $^{Me}$C t T$^L$ AGC ACA CAA

FIG. 19 shows the UV trace from HPLC of HPLC/mass spec for modified oligonucleotide ON15: 5'-dGCA TTC GAG CAA CGT AAG ATC G $^{Me}$C t T$^L$ AGC ACA CAA TCT CAC ACT CTG GAA TTC ACA CTG ACA ATA CTG CCG ACA CAC ATA ACC (SEQ ID NO: 15).

FIG. 20 shows the $^1$H NMR spectrum of 5'-O-(4,4'-dimethoxytrityl)-3'-O-propargyl-LNA thymidine (6).

FIG. 21 shows the $^{13}$C NMR spectrum of 5'-O-(4,4'-dimethoxytrityl)-3'-O-propargyl-LNA thymidine (6).

FIG. 22 shows the $^1$H NMR spectrum of 5'-O-(4,4'-dimethoxytrityl)-3'-O-propargyl-5-methyl LNA cytidine (7).

FIG. 23 shows the $^{13}$C NMR spectrum of 5'-O-(4,4'-dimethoxytrityl)-3'-O-propargyl-5-methyl LNA cytidine (7).

FIG. 24 shows the UV melting studies (derivatives of melting curves). DNA:RNA hybrid duplex containing a triazole linkage are stabilized by the introduction of LNA next to the triazole linkage (compare ON2 and ON3) For sequences see Table 5.

FIG. 25 shows LNA triazole stabilisation of oligonucleotides to 3'-exonuclease digestion. The unmodified ON (lanes 2-4) and LNA ON (lanes 6-8) were fully digested within 5 min whereas the LNA-triazole-LNA ON was still visible after 30 min (lane 12).

FIG. 26 shows LNA triazole DNA template is correctly amplified by PCR. A) 2% agarose gel using template GCA TTC GAG CAA CGT AAG ATC GMeCtTL AGC ACA CAA TCT CAC ACT CTG GAA TTC ACA CTG ACA ATA CTG CCG ACA CAC ATA ACC (SEQ ID NO: 1) where t represent triazole linkage and TL is LNA thymidine. Lane 1; 25 bp ladder. Lane 2; PCR reaction using modified template. Lane 3; negative control, PCR reaction with primers but no template. Lane 4; positive control, PCR reaction with unmodified template. B) UV trace from HPLC of HPLC/mass spec and ESI mass spectrum of the PCR product (both strands). [M+A] strand 1: calc. 25053, found 25055. Strand 2: calc. 25496, found 25497.

General Synthetic Procedures

All reagents were purchased from Sigma-Aldrich, Alfa Aesar, Fisher Scientific, or Link Technologies and used without further purification. Pyridine (from KOH) and POCl$_3$ were freshly distilled before use, and THF was obtained using the MBraun SPS Bench Top solvent purification system (SPS). All air/moisture sensitive reactions were carried out under inert atmosphere (argon) in oven-dried glassware. Reactions were monitored by thin layer chromatography (TLC) using Merck Kieselgel 60 F24 silica gel plates (0.22 mm thickness, aluminium backed). The compounds were visualized by UV irradiation at 254/265 nm and by staining in p-anisaldehyde solution. Column chromatography was carried out under pressure (Flash Master Personal) using Biotage Isolute SPE columns. Columns were primed with $CH_2Cl_2$ containing 1% pyridine prior to use. $^1H$ and $^{13}C$ spectra were measured on a Bruker AVII 500 spectrometer at 500 MHz and 126 MHz, respectively. Chemical shifts are given in ppm and were internally referenced to the appropriate residual solvent signal, all coupling constants (J) are quoted in Hertz (Hz). Assignment of compounds was aided by COSY, HSQC, HMBC, and DEPT-135 experiments. High-resolution mass spectra were measured on a Bruker 9.4 FT-ICR-MS mass spectrometer, and samples were run in MeOH.

Synthesis of 5'-O-(4,4'-dimethoxytrityl)-3'-O-propargyl-LNA thymidine (6)

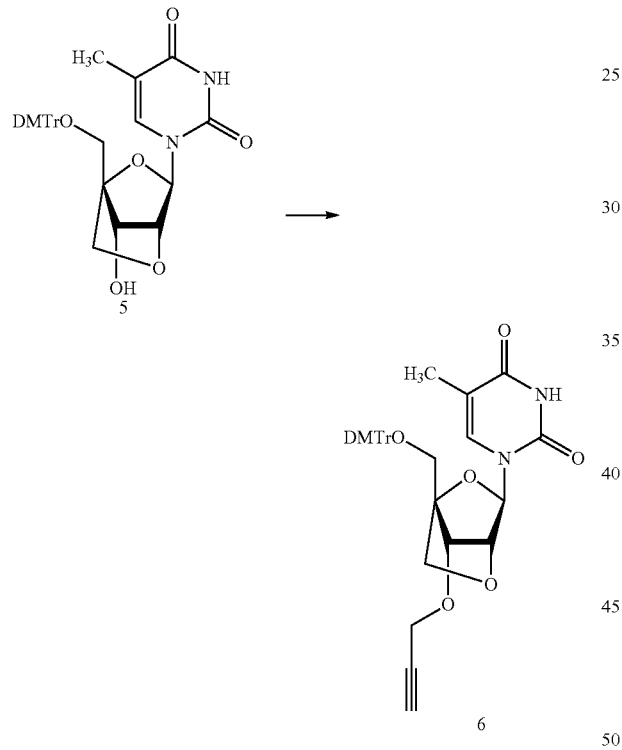

Nucleoside $5^{S1}$ (2.00 g, 3.50 mmol) was co-evaporated with anhydrous THF (3×15 mL) and re-dissolved in anhydrous THF (24 mL). The solution was cooled to 0° C. and NaH (60% suspension in mineral oil, 0.348 g, 14.5 mmol) was added in portions over 5 min. The reaction mixture was stirred on ice for 30 min and at room temperature for 1 h. Propargyl bromide (0.374 mL, 4.20 mmol) was added at 0° C. and the reaction was stirred on ice for 30 min and at room temperature for 16 h. Solvent was removed at reduced pressure and the residue was dissolved in EtOAc (100 mL) and washed with brine (2×50 mL). The organic phase was dried ($Na_2SO_4$) and concentrated and the resulting crude was purified using column chromatography (EtOAc in hexane, 10% to 80%, v/v) to obtain compound 6 (1.68 g, 2.75 mmol, 79%) as a white foam. $R_f$=0.4 (70% EtOAc in hexane, v/v). ESI HRMS m/z 633.2208 ([M+Na]+, $C_{35}H_{34}O_8N_2Na^+$ calc. 633.2207. $^1H$ NMR (500 MHz, DMSO-$d_6$) δ 11.47 (s, 1H, NH), 7.59 (d, J=1.1 Hz, 1H, H-6), 7.46-7.45 (m, 2H, DMTr), 7.36-7.31 (m, 6H, DMTr), 7.28-7.25 (m, 1H, DMTr), 6.93 (d, J=8.8 Hz, 4H, DMTr), 5.52 (s, 1H, H-1'), 4.60 (s, 1H, H-2'), 4.37-4.32 (m, 2H, H-3', C$\underline{H}_2$—C≡CH), 4.29 (dd, J=15.9, 2.4 Hz, 1H, C$\underline{H}_2$—C≡CH), 3.75 (s, 6H, $OCH_3$), 3.72-3.70 (d, J=8.0 Hz, 1H, H-5''), 3.69-3.68 (d, J=8.0 Hz, 1H, H-5''), 3.58 (t, J=2.4 Hz, 1H, C≡C$\underline{H}$), 3.39 (d, J=11.8 Hz, 1H, H-5'), 3.36-3.34 (m, 1H, H-5', merged with $H_2O$ signal from DMSO-$d_6$), 1.56 (d, J=1.1 Hz, 3H, $CH_3$).$^{13}C$ NMR (126 MHz, DMSO) δ 164.3 (C4), 158.7 (DMTr), 150.3 (C2), 145.0, 135.6, 135.4 (DMTr), 134.5 (C6), 130.25, 130.18, 128.5, 128.1, 127.3, 113.8 (DMTr), 109.1 (C5), 87.1 (C4'), 87.0 (C1'), 86.3 (DMTr), 80.2 ($\underline{C}$≡CH), 78.6 (C≡$\underline{C}$H), 76.5 (C2'), 75.8 (C3'), 72.1 (C5''), 58.4 (C5'), 57.4 ($\underline{C}H_2$—C≡CH), 55.5 ($OCH_3$), 12.9 ($CH_3$).

Synthesis of 5'-O-(4,4'-dimethoxytrityl)-3'-O-propargyl-5-methyl LNA cytidine (7)

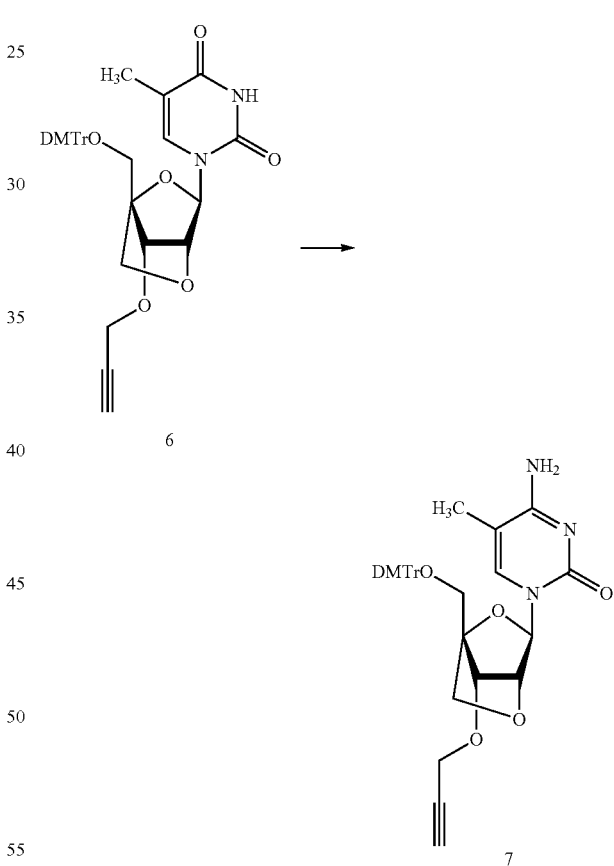

Nucleoside 6 (0.408 g, 0.668 mmol) was co-evaporated with anhydrous pyridine (3×10 mL) and re-dissolved in anhydrous pyridine (5 mL). The solution was cooled to 0° C. and N-methylimidazole (0.7 mL, 8.8 mmol) was added. The reaction mixture was stirred at 0° C. for 15 min, whereupon a freshly distilled $POCl_3$ (0.25 mL, 2.7 mmol) was added dropwise. The reaction was stirred at 0° C. for 30 min and then at room temperature for an additional 30 min Concentrated aqueous ammonia (5 mL) was added and the reaction was stirred at room temperature for 16 h. The solvents were removed under reduced pressure. The residue was dissolved in CH$_2$Cl$_2$ (50 mL) and washed with brine (2×30 mL). The aqueous phase was back extracted with CH$_2$Cl$_2$ (2×30 mL). The combined organic phase was dried (Na$_2$SO$_4$), and concentrated under reduced pressure. The crude was then purified using column chromatography (0% to 7% MeOH/CH$_2$Cl$_2$) to obtain nucleoside 7 (0.233 g, 0.382 mmol, 57%) as a white foam. R$_f$=0.5 (8% MeOH in CH$_2$Cl$_2$, v/v). ESI HRMS m/z 608.2406 ([M−H]$^-$, C$_{35}$H$_{34}$O$_7$N$_3$$^-$ calc. 608.2402. $^1$H NMR (500 MHz, DMSO-d$_6$) δ 7.57 (s, 1H, H-6), 7.47-7.45 (m, 2H, DMTr), 7.41 (broad s, 1H, N—H), 7.37-7.31 (m, 6H, DMTr), 7.28-7.25 (m, 1H, DMTr), 6.93 (d, J=8.8 Hz, 4H, DMTr), 6.85 (broad s, 1H, NH), 5.50 (s, 1H, H-1'), 4.56 (s, 1H, H-2'), 4.34-4.30 (m, 2H, H-3', CH$_2$—C≡CH), 4.25 (dd, J=16.0 Hz, 2.4 Hz, 1H, CH$_2$—C≡CH), 3.75 (s, 6H, OCH$_3$), 3.68 (s, 2H, H-5"), 3.56 (t, J=2.4 Hz, 1H, C≡CH), 3.36 (s, 2H, H-5', merged with H$_2$O signal from DMSO-d$_6$), 1.62 (s, 3H, CH$_3$).$^{13}$C NMR (126 MHz, DMSO) δ 166.0 (C4), 158.7 (DMTr), 155.1 (C2), 144.9 (DMTr), 136.8 (C6), 135.7, 135.5, 130.25, 130.18, 128.5, 128.2, 127.3, 113.83, 113.81 (DMTr), 101.4 (C5), 87.5 (C1'), 86.8 (C4'), 86.3 (DMTr), 80.1 (C≡CH), 78.6 (C≡CH), 76.5 (C2'), 75.5 (C3'), 72.0 (C5"), 58.5 (C5'), 57.4 (CH$_2$—C≡CH), 55.5 (OCH$_3$), 14.0 (CH$_3$).

Preparation of solid support carrying 5'-O-(4,4'-dimethoxytrityl)-3'-O-propargyl-5-methyl LNA cytidine (8)

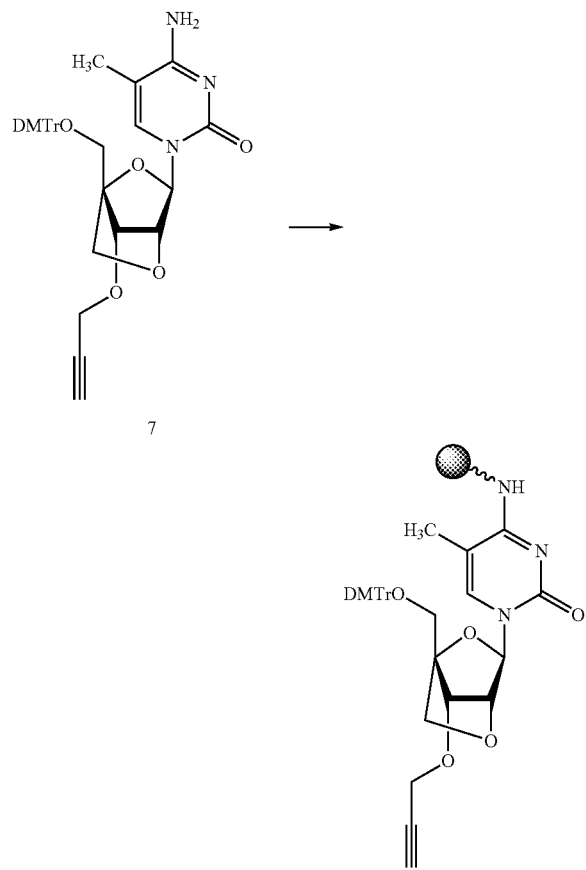

Amino-SynBase resin 500/100 (Link Technologies, Glasgow, UK) (500 Å pore size, loading 69 μmol/g, 4.06 g, 0.28 mmol of amine) was activated using 3% solution of trichloroacetic acid in CH$_2$Cl$_2$ for 3 h in a stoppered glass vessel fitted with a sinter and tap. The solvents were removed by filtration and the support was washed with triethylamine:diisopropylethylamine (9:1), CH$_2$Cl$_2$, and diethyl ether. The support was dried under vacuum for 1 h and re-suspended in anhydrous pyridine (10 mL). A solution of succinic anhydride (0.813 g, 8.13 mmol) and DMAP (160 mg, 1.3 mmol) in anhydrous pyridine (5 mL) was added and the vessel was rotated at room temperature for 20 h. The solvents were removed by filtration, and the support was washed with pyridine, CH$_2$Cl$_2$, and diethyl ether and dried under high vacuum for 1 h. 500 mg of the activated resin was taken forward and soaked in 1 mL of anhydrous pyridine for 10 min. Diisopropyl carbodiimide (DIC) (93 μL, 0.60 mmol), 1-hydroxybenzotriazole (HOBT) (93 μL, 0.69 mmol), and compound 7 (86 mg, 0.14 mmol) were added to the reaction vessel, and the vessel was rotated for 20 h at room temperature. Pentachlorophenol (45 mg, 0.17 mmol) was added, and the vessel was rotated for an additional 3 h. The solvents were removed by filtration, and the support was washed with pyridine, CH$_2$Cl$_2$, and diethyl ether. Piperdine (10% in DMF, 2 mL) was added and the vessel was rotated for 5 min at room temperature. The solvent was removed by filtration and the support was washed with CH$_2$Cl$_2$ and diethyl ether. Capping reagent (oligonucleotide synthesis grade, acetic anhydride/pyridine/THF:N-methylimidazole in THF, 1:1, 2 mL) was added and the vessel was rotated at room temperature for 1 h. The solvent was removed by filtration, and the resin was washed with pyridine, CH$_2$Cl$_2$, and diethyl ether and dried under high vacuum overnight. Loading of nucleoside 7 on the support determined by cleaving the DMT group and was found to be 26 μmol/g.

Synthesis and Purification of oligonucleotides
Synthesis of DNA Oligonucleotides Standard DNA phosphoramidites, solid supports and reagents were purchased from Link Technologies and Applied Biosystems. LNA phosphoramidites were obtained from Exiqon. Automated solid phase synthesis of oligonucleotides (trityl off) was performed on an Applied Biosystems 394 synthesiser. Synthesis was performed on 1.0 μmole scale involving cycles of acid-catalyzed detritylation, coupling, capping, and iodine oxidation. Standard DNA phosphoramidites were coupled for 60 s while extended coupling time of 10 min was used for LNA phosphoramidites. Coupling efficiencies and overall synthesis yields were determined by the inbuilt automated trityl cation conductivity monitoring facility and were ≥98.0% in all cases. The oligonucleotides were then cleaved from the solid support and protecting groups from the nucleobase and backbone were removed by exposure to concentrated aqueous ammonium hydroxide for 60 min at room temperature followed by heating in a sealed tube for 5 h at 55° C.

Synthesis of RNA Oligonucleotides

2'-TBS protected RNA phosphoramidite monomers with t-butylphenoxyacetyl protection of the A, G and C nucleobases were used to assemble RNA oligonucleotides. Benzylthiotetrazole (BTT) was used as the coupling agent, t-butylphenoxyacetic anhydride as the capping agent and 0.1 M iodine as the oxidizing agent (Sigma-Aldrich). Coupling time of 10 min was used and coupling efficiencies of >97% were obtained. Cleavage of oligonucleotides from the solid support and protecting groups from the nucleobase and backbone were removed by exposure to concentrated aqueous ammonia/ethanol (3/1 v/v) for 2 h at room temperature followed by heating in a sealed tube for 2 h at 55° C.

Removal of 2'-TBS Protection of RNA Oligonucleotides

After cleavage from the solid support and removal of the protecting groups from the nucleobases and phosphodiesters in ammonia/ethanol as described above, oligonucleotides were concentrated to a small volume in vacuo, transferred to 15 mL plastic tubes and freeze dried (lyophilised). The residue was dissolved in DMSO (300 µL) and triethylamine trihydrofluoride (300 µL) was added after which the reaction mixtures were kept at 65° C. for 2.5 h. Sodium acetate (3 M, 50 µL) and butanol (3 mL) were added with vortexing and the samples were kept at −80° C. for 30 min then centrifuged at 13,000 rpm at 4° C. for 10 min. The supernatant was decanted and the precipitate was washed twice with ethanol (0.75 mL) then dried under vacuum.

Purification of Oligonucleotides (DNA or RNA)

The fully deprotected oligonucleotides were then purified by reverse-phase high performance liquid chromatography (HPLC) on a Gilson system using a Luna 10 µm C8(2) 100 Å pore Phenomenex column (250×10 mm) with a gradient of acetonitrile in triethylammonium bicarbonate (TEAB) over 20 min at a flow rate of 4 mL per minute. Buffer A: 0.1 M TEAB, pH 7.5; buffer B: 0.1 M TEAB, pH 7.5, with 50% acetonitrile were used. Elution was monitored by UV absorption between 260-295 nm.

Synthesis of 3'-alkyne-5-methyl dC oligonucleotides and 3'-alkyne-5-methyl LNA-C oligonucleotides 3'-Alkyne-5-methyl dC oligonucleotides were synthesized on 1.0 µmole scale using 5'-O-(4,4'-dimethoxytrityl)-3'-O-propargyl-5-methyldeoxycytidine solid support (33 µmole/g loading on AM polystyrene, Applied Biosystems).[S2] The resin was packed into a twist column and the desired oligonucleotides were assembled and purified by standard phosphoramidite oligonucleotide synthesis (described above). 3'-Alkyne-5-methyl LNA-C oligonucleotides were synthesized by a similar procedure using the solid support 8. Purified oligonucleotides were characterised by electrospray mass spectrometry. Mass spectra of oligonucleotides were recorded either using a Bruker micrOTOFTM II focus ESI-TOF MS instrument in ES− mode or a XEVO G2-QTOF MS instrument in ES− mode (Table 1).

Synthesis of 5'-azide modified oligonucleotides

Trityl off oligonucleotides were assembled at 1.0 µmole scale and were treated with a 0.5 M solution of methyltriphenoxyphosphonium iodide in DMF (1.0 mL) while attached to the solid support in a synthesis column.[S3] The solution was periodically passed through the column using two 1 mL syringes for 20 min at room temperature. The resin was then washed several times with DMF. In a separate vessel 50 mg of sodium azide was taken up in 1 mL DMF and heated to 70° C. for 10 min. The mixture was allowed to cool to room temperature and the supernatant was passed back and forth through the synthesis column using two 1 mL syringes.[S4] The synthesis column was left at 55° C. for 5 h and during this time the solution was occasionally passed back and forth. The column was then washed with DMF followed by acetonitrile and dried by the passage of a stream of argon. The resultant 5'-azide oligonucleotide was cleaved from solid support and deprotected by exposure to concentrated aqueous ammonium hydroxide for 60 min at room temperature followed by heating in a sealed tube for 5 h at 55° C. and purified as described above. Purified oligonucleotides were then characterised by mass spectrometry (Table 1).

Synthesis of 13-Mer Oligonucleotides Incorporating a Single Triazole Linkage

Representative Procedure

A mixture of 5'-azide oligonucleotide (130 nm) and 3'-alkyne oligonucleotide (100 nm) was freeze dried and re-dissolved in milli-Q water (250 µL). The solution was flushed with a stream of argon and to this was added an aqueous solution of CuSO$_4$ (20 µL, 100 mM), an aqueous solution of sodium ascorbate (40 µL, 500 mM), and tris-hydroxypropyltriazole ligand[S5] (5 mg). The resulting mixture was degassed with a stream of argon and left at room temperature for 2 h with occasional shaking. Reagents were then removed by NAP-10 gel-filtration and the ligated triazole oligonucleotide was purified by HPLC (as described above) and characterized by mass spectrometry (Table 1).

Synthesis of 13-Mer Oligonucleotides Incorporating Two Triazole Linkages

Representative Procedure

A 5'-azide oligonucleotide, a 3'-alkyne oligonucleotide, a 5'-azide-3'-alkyne oligonucleotide and a splint (40 nm each) were mixed with NaCl (200 µL, 3 M). Milli-Q water was added to raise the total volume to 1940 µL. The mixture was annealed by heating to 80° C. and then cooling slowly to room temperature. The content was then kept at 4° C. for 1 h. CuSO$_4$ (aqueous, 20 µL, 100 mM), sodium ascorbate (aqueous, 40 µL, 500 mM), and tris-hydroxypropyltriazole ligand[5] (4 mg) were added. Thus a final concentration of 20 µM of each oligo in 300 mM NaCl and a final volume of 2 mL was obtained. The reaction mixture was left at 4° C. for 3 h and then at room temperature for 1 h. Reagents were then removed by NAP-10 gel-filtration and the ligated triazole oligonucleotide was purified by denaturing 20% polyacrylamide gel electrophoresis and characterized by mass spectrometry (Table 1). Splint used: 5'-dTTTTTT GCTAGAGAAGTCG TTTTTT (SEQ ID NO: 16) (For ON8 and ON9), 5'-dTTTTTTGCTGGAGAGGTCGTTTTTT (SEQ ID NO: 17) (for ON13 and ON14).

Synthesis of an 81-Mer Template Incorporating a Single LNA-Triazole Linkage

ON32 and ON18 (Table 1, 70 nm of each) and a splint (70 nm) were mixed with NaCl (200 µL, 3 M) and total volume was brought to 1940 µL by the addition of milli-Q water. The mixture was annealed by heating to 80° C. and then cooling slowly to room temperature. CuSO$_4$ (aqueous, 20 µL, 100 mM), sodium ascorbate (aqueous, 40 µL, 500 mM), and tris-hydroxypropyltriazole ligand (4 mg) were added. The reaction mixture was left at room temperature for 3 h. Reagents were then removed by NAP-10 gel-filtration and the ligated triazole oligonucleotide was purified by denaturing 12% polyacrylamide gel electrophoresis, and characterized by mass spectrometry (ON15, Table 1). Splint used: 5'-dTGTGTGCTAGCGATCTTA (SEQ ID NO:18).

TABLE 1

Mass spec analysis of modified oligonucleotides

| ON code | Sequence | Calc mass | Found mass |
|---|---|---|---|
| ON2 | 5'-dCGACG$^{Me}$Ct T$^L$TGCAGC (SEQ ID NO: 5) | 3978 | 3978 |
| ON3 | 5'-dCGACG$^{Me}$CtTTGCAGC (SEQ ID NO: 6) | 3950 | 3950 |
| ON5 | 5'-dCGACG$^{Me}$C$^L$tTTGCAGC (SEQ ID NO: 7) | 3978 | 3978 |
| ON6 | 5'-dCGACG$^{Me}$C$^L$tT$^L$TGCAGC (SEQ ID NO: 8) | 4006 | 4006 |
| ON8 | 5'-dCGA$^{Me}$CtT$^L$TCT$^{Me}$CtT$^L$AGC (SEQ ID NO: 9) | 3971 | 3972 |
| ON9 | 5'-dCGA$^{Me}$CtTTCT$^{Me}$CtTAGC (SEQ ID NO: 10) | 3915 | 3915 |
| ON11 | 5'-dCGACG$^{Me}$Ct$^{Me}$C$^L$TGCAGC (SEQ ID NO: 11) | 3977 | 3977 |
| ON12 | 5'-dCGACG$^{Me}$Ct$^{Me}$CTGCAGC (SEQ ID NO: 12) | 3949 | 3949 |
| ON13 | 5'-dCGA$^{Me}$Ct$^{Me}$C$^L$TCT$^{Me}$Ct$^{Me}$C$^L$AGC (SEQ ID NO: 13) | 3969 | 3970 |
| ON14 | 5'-dCGA$^{Me}$Ct$^{Me}$CTCT$^{Me}$Ct$^{Me}$CAGC (SEQ ID NO: 14) | 3913 | 3914 |
| ON15 | 5'-dGCA TTC GAG CAA CGT AAG ATC G$^{Me}$CtT$^L$ AGC ACA CAA TCT CAC ACT CTG GAA TTC ACA CTG ACA ATA CTG CCG ACA CAC ATA ACC (SEQ ID NO: 15) | 24783 | 24781 |
| ON16 | 5'-dCGACG$^{Me}$C-(alkyne) | 1829 | 1829 |
| ON17 | 5'-dCGA$^{Me}$C(3'-alkyne) | 1210 | 1210 |
| ON18 | 5'-dGCATTCGAGCAACGTAAGATCG $^{Me}$C(3'-alkyne) (SEQ ID NO: 19) | 7110 | 7110 |
| ON19 | 5'-dCGACG$^{Me}$C$^L$-(3'-LNA alkyne) | 1857 | 1857 |
| ON20 | 5'-dN$_3$-$^{Me}$C$^L$TGCAGC | 2148 | 2148 |
| ON21 | 5'-dN$_3$-T$^L$TGCAGC | 2149 | 2149 |
| ON22 | 5'-dN$_3$-$^{Me}$CTGCAGC | 2120 | 2120 |
| ON23 | 5'-dN$_3$-TTGCAGC | 2121 | 2121 |
| ON24 | 5'-dN$_3$-$^{Me}$CAGC | 1197 | 1197 |
| ON25 | 5'-dN$_3$-TAGC | 1198 | 1198 |
| ON26 | 5'-dN$_3$-$^{Me}$C$^L$AGC | 1225 | 1225 |
| ON27 | 5'-dN$_3$-T$^L$AGC | 1226 | 1226 |
| ON28 | 5'-dN$_3$-TTCT$^{Me}$C(3'-alkyne) | 1506 | 1506 |
| ON29 | 5'-dN$_3$-$^{Me}$CTCT$^{Me}$C(3'-alkyne) | 1505 | 1505 |
| ON30 | 5'-dN$_3$-T$^L$TCT$^{Me}$C(3'-alkyne) | 1534 | 1534 |
| ON31 | 5'-dN$_3$-$^{Me}$C$^L$TCT$^{Me}$C(3'-alkyne) | 1533 | 1533 |
| ON32 | 5'-dN$_3$-T$^L$AG CAC ACA ATC TCA CAC TCT GGA ATT CAC ACT GAC AAT ACT GCC GAC ACA CAT AAC C (SEQ ID NO: 20) | 17673 | 17673 | t denotes triazole linkage

Ultraviolet Melting Studies

UV DNA melting curves were recorded in a Cary 4000 Scan UV-Visible Spectrophotometer using 3 μM of each oligonucleotide in a 10 mM phosphate buffer containing 200 mM NaCl at pH 7.0. Samples were annealed by heating to 85° C. (10° C./min) and then slowly cooling to 20° C. (1° C./min). As these six successive cycles (heating and cooling) were performed at a gradient of 1° C./min, the change in UV absorbance at 260 nm was recorded. The melting temperature was calculated from the 1$^{st}$ derivative of the melting curve using in built software.

Results from the application of the above described method are depicted in FIGS. 1 to 4.

Additional $T_m$ Data

TABLE 2

Thermal melting ($T_m$) data for duplexes incorporating a single triazole linkage ($^{Me}C$-$^{Me}C$ step).

| ON Code | ON Sequence | DNA target $T_m{}^a$ | DNA target $\Delta T_m{}^b$ | RNA target $T_m{}^a$ | RNA target $\Delta T_m{}^b$ |
|---|---|---|---|---|---|
| ON33 | 5'-d CGACG$^{Me}$Cp$^{Me}$CTGCAGC (SEQ ID NO: 21) | 68.7 | | 69.1 | |
| ON11 | 5'-dCGACG$^{Me}$Ct$^{Me}$C$^L$TGCAGC (SEQ ID NO: 11) | 63.5 | -5.1 | 68.6 | -0.5 |
| ON12 | 5'-d CGACG$^{Me}$Ct$^{Me}$CTGCAGC (SEQ ID NO: 12) | 62.0 | -6.4 | 63.4 | -5.8 |
| ON34 | 5'-d CGACG$^{Me}$Cp$^{Me}$C$^L$TGCAGC (SEQ ID NO: 22) | 72.0 | +3.3 | 74.7 | +5.6 |

$^a$Melting temperatures ($T_m$) were obtained from the maxima of the first derivatives of the melting curves (A$_{260}$ vs. temperature) recorded in a buffer containing 10 mM phosphate and 200 mM NaCl at pH 7.0 using 3.0 μM concentrations of each strand.
$^b\Delta T_m$ = change in $T_m$ for a modified duplex relative to the unmodified duplex (ON33), $^{Me}C$ is 5-methylcytosine, $^{Me}C^L$ is 5-methylcytosine LNA, t denotes a triazole linkage and p denotes a normal phosphodiester linkage. DNA target 5'-dGCT GCA GGC GTC G (SEQ ID NO: 23), RNA target 5'-rGCU GCA GGC GUC G (SEQ ID NO: 24).

TABLE 3

Mismatch discrimination of oligonucleotides incorporating a single triazole linkage ($^{Me}C$-T step) against RNA targets containing a mismatch nucleotide opposite the thymine nucleobase on 3'-side of the triazole linkage.

| | | RNA Target 3'-rGCUGCGMACGUCG | | | |
|---|---|---|---|---|---|
| ON Code | ON SEQUENCE | $T_M{}^a$ M = A | $\Delta T_M$ G | $\Delta T_M$ C | $\Delta T_M$ U |
| ON1 | 5'-dCGACG$^{Me}$CpTTGCAGC (SEQ ID NO: 25) | 62.8 | -3.9 | -16.3 | -13.7 |
| ON2 | 5'-dCGACG$^{Me}$CtT$^L$TGCAGC (SEQ ID NO: 5) | 62.0 | -3.3 | -15.6 | -13.4 |
| ON3 | 5'-dCGACG$^{Me}$CtTTGCAGC (SEQ ID NO: 6) | 56.6 | -2.2 | -16.1 | -12.9 |
| ON4 | 5'-dCGACG$^{Me}$CpT$^L$TGCAGC (SEQ ID NO: 26) | 68.9 | -4.8 | -15.2 | -13.7 |

$^a$See Table 2. $\Delta T_m$ = change in $T_m$ relative to the fully matched duplex (M = A). $^{Me}C$ is 5-methylcytosine, $^{Me}C^L$ is 5-methylcytosine LNA, t denotes a triazole linkage and p denotes a normal phosphodiester linkage.

TABLE 4

Thermal melting ($T_m$) data for duplexes incorporating two triazole linkages ($^{Me}C$-$^{Me}C$ steps).

| ON Code | Sequence | DNA target $T_m^a$ | $\Delta T_m/mod^b$ | RNA target $T_m^a$ | $\Delta T_m/mod^b$ |
|---|---|---|---|---|---|
| ON35 | 5'-dCGA$^{Me}$Cp$^{Me}$CTCT$^{Me}$Cp$^{Me}$CAGC (SEQ ID NO: 27) | 66.6 | | 70.1 | |
| ON13 | 5'-dCGA$^{Me}$Ct$^{Me}$C$^L$TCT$^{Me}$Ct$^{Me}$C$^L$AGC (SEQ ID NO: 13) | 56.4 | −5.1 | 67.1 | −1.5 |
| ON14 | 5'-dCGA$^{Me}$Ct$^{Me}$CTCT$^{Me}$Ct$^{Me}$CAGC (SEQ ID NO: 14) | 51.9 | −7.3 | 59.1 | −5.5 |
| ON36 | 5'-dCGA$^{Me}$Cp$^{Me}$C$^L$TCT$^{Me}$Cp$^{Me}$C$^L$AGC (SEQ ID NO: 28) | 72.2 | +2.8 | >75 | >+2.5 |

$^{a,b}$see Table 2 footnote. DNA target: 5'-dGCT GGA GAG GTC G (SEQ ID NO: 39), RNA target: 5'-rG CUA GAG AAG UC G (SEQ ID NO: 40)

CD Spectroscopy

CD spectra (200-340 nm) were recorded on a Chirscan Plus spectropolarimeter using a Quartz optical cells with a path length of 3.0 mm Scans were performed at 20° C. using a step size of 0.5 nm, a time per point of 1.0 s and a bandwidth of 2 nm, and the average of four scans is presented. Samples from UV melting studies (3 μM of each oligonucleotide in a 10 mM phosphate buffer containing 200 mM NaCl at pH 7.0) were used directly and were annealed by heating to 85° C. and then slowly cooled to 20° C. prior to recording CD spectrum. The average trace was smoothed (20 points) using in built software. A CD spectrum of only buffer was also recorded and was subtracted from the collected data. Finally, spectra were baseline-corrected using the offset at 340 nm.

Results from the application of the above described method are depicted in FIGS. 5 and 6.

Snake Venom Phosphodiesterase Stability 5 nm of oligonucleotide was dissolved in 50 μL buffer (100 mM Tris-HCl, 20 mM MgCl$_2$, pH=9.0). 10 μL of this solution was removed as a control (zero min) and was diluted with H$_2$O (10 μL). To the remaining solution was added 30 μL H$_2$O followed by 10 μL aqueous solution of Phosphodiesterase 1 from *Crotalus adamanteus* venom (from Sigma Aldrich, catalogue number P3243, 0.45 units, dissolved in 700 μL H$_2$O). The reaction was incubated at 37° C. and aliquots (20 μL) were taken at different time intervals, mixed with formamide (20 μL) and stored at −20° C. The samples were then analysed by denaturing 20% polyacrylamide gel electrophoresis.

Results from the application of the above described method are depicted in FIG. 7.

Linear Copying of an 81-Mer Template Incorporating a Single LNA-Triazole Linkage A reaction mixture was prepared by mixing 10 μL of 10× NEB buffer 2* in a total reaction volume of 100 μL with template, primer or template+primer (110 μmol of each), 0.2 mM dNTP and 1.0 μL of DNA polymerase 1, Large Klenow fragment (5u/μL). Reaction mixture was left at 37° C. for 2.5 h. Phenol:chloroform:isoamyl alcohol (25:24:1, v/v) solution (100 μL) was added and mixture was vortexed for 30 seconds, centrifuged for 5 min at 5000 rpm. Aqueous phase was collected and sodium acetate (10 μl, 3 M, pH 5.2) and ethanol (330 μL) were added. The mixture was left at −80° C. for 4 h and then centrifuged (13000 rpm) for 20 min at 4° C. The supernatant was removed and the resulting pellet was dissolved in 20 μL H$_2$O. 10 μL sample was used for mass and another 10 μL was analysed by denaturing 10% polyacrylamide gel electrophoresis. Similar gels were obtained when reaction mixture was directly (prior to precipitation) loaded on the gel. Incubation of reaction mixture for 1.5 h showed truncated product in addition to full length product presumably stalling the reaction at the triazole step. The product was analysed by mass spectrometry.

*(10× NEB buffer2 was supplied with the enzyme). 1× NEB buffer 2=50 mM NaCl, 10 mM Tris-HCl, 10 mM MgCl$_2$, 1 mM DTT (pH 7.9 at 25° C.).

Results from the application of the above described method are depicted in FIG. 8.

PCR of an 81-Mer Template Incorporating a Single LNA-Triazole Linkage

PCR amplification of the modified template (ON15) was achieved using GoTaq DNA polymerase. 10 μL of 5× buffer (Promega gree PCR buffer) was used in a total reaction volume of 50 μL with 12.5 ng of the DNA template, 0.5 μM of each primer, 0.2 mM dNTP and 1.25 unit of GoTaq polymerase. PCR cyclic conditions: 95° C. (initial denaturation) for 2 min then 3 cycles of 95° C. (denaturation) for 15 s, 54° C. (annealing) for 20 s and 72° C. extension for 5 min. Next 20 cycles 95° C. (denaturation) for 15 s, 54° C. (annealing) for 20 s and 72° C. extension for 30 s. This was followed by leaving the PCR reaction mixture at 72° C. for 5 min. The PCR amplicon was analysed by loading onto 2% agarose gel, and was precipitated following the procedure described for linear copying for mass analysis. Primers used: 5'-dGCATTCGAGCAACGTAAG (SEQ ID NO: 29), 5'-dGGTTATGTGTGTCGGCAG (SEQ ID NO: 30) (for modified template). The unmodified template 5'-dACGTTAGCACGAAGAGGCATCTTAGCACACAATCTCACACTCTGGAATTCACACTGACAATACTCGCGAACACACCCAAT (SEQ ID NO: 2) was used as a control. Primers used: 5'-dATTGGGTGTGTTCGCGAG (SEQ ID NO: 31), 5'-dACGTTAGCACGAAGAGGC (SEQ ID NO: 32). Mass analysis for control: [M+A] strand 1: Calc. 24764, found 24765. Strand 2: Calc.25167, found 25168.

Results and Discussion

In initial studies we introduced LNA on one or both sides of the triazole linkage (FIG 1d-f).

13-mer oligonucleotides containing a central MeC-T step were synthesised. The ON sequence used was taken from our previous study.[13] Oligonucleotides were mixed with complementary DNA and RNA targets, and the thermal stabilities of the resulting duplexes were recorded by UV melting (Table 5). Interestingly, the thermal stability of the DNA:RNA duplex containing the triazole linkage with LNA on its 3'-side (ON2) was comparable to that of the unmodified duplex with ON1 ($\Delta Tm=-0.8°$ C., FIG. 24). LNA significantly improved the stability of the modified DNA:RNA duplex relative to the duplex with only the triazole linkage (an increase of 5.4° C. in Tm, compare ON2 with ON3, RNA target in Table 5). Thus, incorporation of LNA on the 3'-side of the triazole linkage counteracts the drop in the thermal stability caused by the triazole in the context of DNA:RNA duplexes. Duplexes containing a central MeC-t-MeC step also showed similar trends (Table 2). In contrast, 3'-LNA induced only a small increase of 2.9° C. in the thermal stability of dsDNA compared to the duplex containing only the triazole linkage (compare ON2 and ON3 with DNA target) and the stability of the triazole-LNA duplex was still very low compared to the unmodified dsDNA (ON1 vs ON2, $\Delta Tm=-6.0°$ C.). For duplexes carrying no triazole linkage, LNA had the expected larger effect on binding to RNA targets (ON4, RNA target, $\Delta Tm=6.1°$ C.) compared to DNA targets (ON4, DNA target $\Delta Tm=3.3°$ C.). Preferential binding of LNA modified oligonucleotides for RNA targets is well known, and is due to the LNA sugar preferring the 3'-endo conformation.[16,17] Surprisingly, the presence of LNA on the 5'-side of the triazole had no significant additional stabilising effect on DNA:RNA hybrids or DNA duplexes (Table 5, ON5 and ON6).

TABLE 5

Thermal melting ($T_m$) data for duplexes containing a single triazole linkage.

| ON CODE | ON SEQUENCE (5'-3') | DNA TARGET $T_M^A$ | $\Delta T_M^B$ | RNA TARGET $T_M^A$ | $\Delta T_M^B$ |
|---|---|---|---|---|---|
| ON1 | CGACG$^{Me}$CTTGCAGC (SEQ ID NO: 25) | 64.2 | | 62.8 | |
| ON2 | CGACG$^{Me}$CtT$^L$TGCAGC (SEQ ID NO: 5) | 58.2 | -6.0 | 62.0 | -0.8 |
| ON3 | CGACG$^{Me}$CtTTGCAGC (SEQ ID NO: 6) | 55.3 | -8.9 | 56.6 | -6.2 |
| ON4 | CGACG$^{Me}$CT$^L$TGCAGC (SEQ ID NO: 26) | 67.5 | +3.3 | 68.9 | +6.1 |
| ON5 | CGACG$^{Me}$C$^L$tTTGCAGC (SEQ ID NO: 7) | 52.7 | -11.5 | 55.5 | -7.2 |
| ON6 | CGACG$^{Me}$C$^L$tT$^L$TGCAGC (SEQ ID NO: 8) | 58.4 | -5.8 | 62.9 | +0.1 |

$^A$Melting temperatures ($T_m$) were obtained from the maxima of the first derivatives of the melting curves ($A_{260}$ vs. temperature) recorded in a buffer containing, 10 mM phosphate and 200 mM NaCl at pH 7.0 using 3.0 μM concentrations of each strand.
$^B\Delta T_m$ = change in $T_m$ for a modified duplex relative to the unmodified duplex. T$^L$ is LNA thymidine, $^{Me}$C is 5-methylcytosine and t is a triazole linkage (FIG. 1a). DNA target: 5'-dGCT GCA AGC GTC G (SEQ ID NO: 33). RNA target: 5'-rGCU GCA AGC GUC G (SEQ ID NO: 34).

For therapeutic oligonucleotides improved thermal stability must also be accompanied by efficient mismatch discrimination. The ability of the studied oligonucleotides to discriminate between matched and mismatched RNA strands was assessed by mixing them with targets containing a mismatch nucleotide opposite the thymine nucleobase on 3'-side of the triazole linkage (T-X mismatch where X=C, T or G). The oligonucleotides containing triazole-linked 3'-LNA were found to maintain the fidelity of Watson-Crick base pairing, and effectively discriminated against mismatched targets with efficiency parallel to that of unmodified oligonucleotides (Table 3.).

TABLE 6

Thermal melting ($T_m$) data for duplexes incorporating two triazole linkages.

| ON CODE | ON SEQUENCE (5'-3') | DNA TARGET $T_M^A$ | $\Delta T_M/MOD^B$ | RNA TARGET $T_M^B$ | $\Delta T_M/MOD^B$ |
|---|---|---|---|---|---|
| ON7 | CGA$^{Me}$CTTCT$^{Me}$CTAGC (SEQ ID NO: 35) | 57.1 | | 58.8 | |

TABLE 6-continued

Thermal melting ($T_m$) data for duplexes incorporating two triazole linkages.

| ON CODE | ON SEQUENCE (5'-3') | DNA TARGET $T_M^A$ | $\Delta T_M/MOD^B$ | RNA TARGET $T_M^B$ | $\Delta T_M/MOD^B$ |
|---|---|---|---|---|---|
| ON8 | CGA$^{Me}$CtT$^L$TCT$^{Me}$CtT$^L$AGC (SEQ ID NO: 9) | 48.0 | -4.5 | 57.1 | -0.8 |
| ON9 | CGA$^{Me}$CtTTCT$^{Me}$CtTAGC (SEQ ID NO: 10) | 42.3 | -7.4 | 47.1 | -5.8 |
| ON10 | CGA$^{Me}$CT$^L$TCT$^{Me}$CT$^L$AGC (SEQ ID NO: 36) | 62.2 | +2.5 | 70.0 | +5.6 |

$^{A,B}$See Table 5 footnote. DNA target; 5'-dGCT AGA GAA GTC G (SEQ ID NO: 37). RNA target; 5'-rGCU AGA GAA GUC G (SEQ ID NO: 38).

Next, oligonucleotides incorporating two triazole internucleotide linkage steps were prepared by templated CuAAC click ligation reactions in the presence of a complementary splint. The ligated oligonucleotides were purified by denaturating 20% polyacrylamide gel electrophoresis and were evaluated for their binding affinity for complementary DNA/RNA strands (Table 6). Pleasingly, oligonucleotides containing two triazole-3'-LNA-linkages (MeC-T steps) showed a significant improvement in binding affinity for their RNA targets relative to oligonucleotides incorporating two triazole linkages without 3'-LNA (an increase of 5.0° C./modification in Tm, compare ON8 and ON9, RNA target). When compared to unmodified ON7, a drop of only 0.8° C./modification was observed (ON8, RNA target). These stability studies suggest that DNA:RNA duplexes can tolerate multiple LNA-triazole linkages, which is not feasible for triazole linkages alone due to the greater lowering of Tm. Since the improvement in binding affinity is specific for DNA:RNA hybrids, triazole-linked LNA could find use in selective probes for RNA targeting. Oligonucleotides incorporating two MeC-t-MeC steps showed similar trends (Table 4).

The global structures of the modified duplexes were also studied by CD-spectroscopy (FIGS. 5 and 6). Both modified and unmodified duplexes showed similar CD spectra suggesting that neither LNA nor triazole-linkage induced any significant change in the global geometry of the studied duplexes.

3'-Exonuclease stability studies using snake venom phosphodiesterase 1 (SVPD, from *Crotalus adamanteus* venom) showed that the combination of triazole and 3'-LNA is more resistant to degradation than unmodified oligonucleotides or those containing only LNA (FIG. 7), and the combination of 5'-LNA-triazole-3'LNA was highly stabilising (FIG. 25). Evidence for the enzyme pausing at the modified backbone linkage is clearly visible (FIG. 25 lane 12). The presence of the triazole seems to protect the unmodified nucleotides on its 3'-side possibly by reducing binding to the enzyme.

Finally, we set out to see if the triazole-linkage in combination with LNA at its 3'-side can be read through by DNA polymerases. To evaluate this, an 81-mer PCR template containing triazole LNA was prepared by a splint assisted CuAAC click ligation reaction. PCR amplification of this modified template was achieved using Gotaq DNA polymerase (FIG. 26). The PCR reaction requires a long extension time for first few cycles (5 min), in agreement with a previous report of LNA-modified templates being amplified by PCR.27 The amplicon was shown by agarose gel electrophoresis and mass spectrometry to be the fully extended product. A linear copying experiment for the same template using DNA polymerase 1, Large Klenow fragment and a reaction time of 2.5 h also gave a fully extended product. Although this extension time is longer than required for templates with only a triazole linkage8 (no LNA) it demonstrates that the combination of LNA and triazole can be reliably read through by DNA polymerases.

While specific embodiments of the invention have been described for the purpose of reference and illustration, various modifications will be apparent to a person skilled in the art without departing from the scope of the invention as defined by the appended claims.

REFERENCES

1. A. H. El-Sagheer and T. Brown, *Chem Soc Rev*, 2010, 39, 1388-1405.
2. T. Fujino, T. Suzuki, K. Okada, K. Kogashi, K. I. Yasumoto, K. Sogawa and H. Isobe, *J Org Chem*, 2016, 81, 8967-8976.
3. K. Kogashi, K. Okada, M. Mattarella, T. Suzuki, K. Yasumoto, K. Sogawa and H. Isobe, *Chem Asian J*, 10, 2683-2688.
4. H. Isobe and T. Fujino, *Chem Rec*, 2014, 14, 41-51.
5. A. M. Varizhuk, D. N. Kaluzhny, R. A. Novikov, A. O. Chizhov, I. P. Smirnov, A. N. Chuvilin, O. N. Tatarinova, G. Y. Fisunov, G. E. Pozmogova and V. L. Florentiev, *J Org Chem*, 2013, 78, 5964-5969.
6. A. M. Varizhuk, V. B. Tsvetkov, O. N. Tatarinova, D. N. Kaluzhny, V. L. Florentiev, E. N. Timofeev, A. K. Shchyolkina, O. F. Borisova, I. P. Smirnov, S. L. Grokhovsky, A. V. Aseychev and G. E. Pozmogova, *Eur J Med Chem*, 2013, 67, 90-97.
7. A. H. El-Sagheer and T. Brown, *Acc Chem Res*, 2012, 45, 1258-1267.
8. A. H. El-Sagheer, A. P. Sanzone, R. Gao, A. Tavassoli and T. Brown, *Proc Natl Acad Sci USA*, 2011, 108, 11338-11343.
9. A. H. El-Sagheer and T. Brown, *Chemical Commun*, 2011, 47, 12057-12058.
10. C. N. Birts, A. P. Sanzone, A. H. El-Sagheer, J. P. Blaydes, T. Brown and A. Tavassoli, *Angew Chem Int Ed*, 2014, 53, 2362-2365.
11. A. Dallmann, A. H. El-Sagheer, L. Dehmel, C. Mügge, C. Griesinger, N. P. Ernsting and T. Brown, *Chem Eur J*, 2011, 17, 14714-14717.

12. V. Madhuri and V. A. Kumar, Nucleosides, *Nucleotides and Nucleic Acids,* 2012, 31, 97-111.
13. A. H. El-Sagheer and T. Brown, *Chem Sci,* 2014, 5, 253-259.
14. A. Shivalingam, A. E. S. Tyburn, A. H. El-Sagheer and T. Brown, *J Am Chem Soc,* 2017, 139, 1575-1583.
15. M. J. Palframan, R. D. Alharthy, P. K. Powalowska and C. J. Hayes, *Org Biomol Chem,* 2016, 14, 3112-3119.
16. S. K. Singh and J. Wengel, *Chem Commun,* 1998, 1247-1248.
17. S. Obika, D. Nanbu, Y. Hari, J. I. Andoh, K. I. Morio, T. Doi and T. Imanishi, *Tetrahedron Lett,* 1998, 39, 5401-5404.
18. H. Kaur, B. R. Babu and S. Maiti, *Chem Rev,* 2007, 107, 4672-4697.
19. J. K. Watts, *Chem Commun,* 2013, 49, 5618-5620.
S1. S. Obika, T. Uneda, T. Sugimoto, D. Nambu, T. Minami, T. Doi, T Imanishi, Bioorg Med Chem 2001, 9, 1001-1011.
S2. A. H. El-Sagheer, A. P. Sanzone, R. Gao, A. Tavassoli and T. Brown, Proc Natl Acad Sci U S A, 2011, 108, 11338-11343.
S3. G. P. Miller and E. T. Kool, Org Lett, 2002, 4, 3599-3601.
S4. G. P. Miller and E. T. Kool, J Org Chem, 2004, 69, 2404-2410.
S5. T. R. Chan, R. Hilgraf, K. B. Sharpless and V. V. Fokin, Org Lett, 2004, 6, 2853-2855.

The invention claimed is:

1. An oligonucleotide having a 5' and a 3' end and a sequence of nucleosides linked together by inter-nucleoside linkages, comprising a triazole linker moiety having a 5' and a 3' end and a locked nucleoside positioned at the 3' end of the triazole linker moiety;
wherein the triazole linker moiety is a group of Formula A or Formula B:

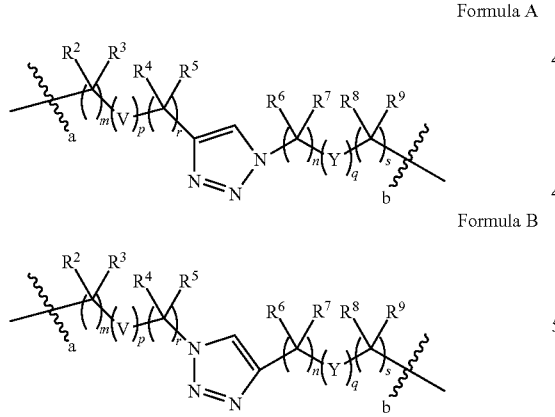

wherein:
- ⌇a denotes the 5' end of linker moiety, wherein the 5' end of the linker moiety is linked to the locked nucleoside;
- ⌇b denotes the 3' end of the linker moiety, wherein the 3' end of the linker moiety is linked to the nucleoside;
- $R^2$, $R^3$, $R^4$, $R^5$, $R^6$, $R^7$, $R^8$ and $R^9$ are each independently selected from hydrogen or (1-4C)alkyl, wherein each (1-4C)alkyl is optionally substituted with one or more $NH_2$, or OH or SH;
- V and Y are independently selected from O, S or $NR^x$, wherein $R^x$ is selected from hydrogen or (1-4C)alkyl;

m, n, r and s are integers independently selected from 0, 1 or 2; and
p and q are integers independently selected from 0 or 1; with the proviso that the sum of integers m, n, p, q, r and s is either 0, 1, 2, 3, 4, 5 or 6; and
the locked nucleoside has the general structure:

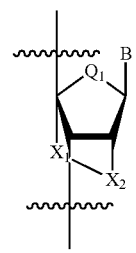

wherein:
- $Q_1$ is selected from $CR^pR^q$, O, S or $NR^a$, wherein $R^p$ and $R^q$ are each indepenedently selected from H, (1-4C)alkyl or halo and $R^a$ is selected from hydrogen or (1-4C)alkyl;
- B is a nucleobase; and
- one of $X_1$ and $X_2$ is selected from $(CR^aR^b)_x$, wherein x is selected from 1 or 2 and the other is selected from $CR^aR^b$, O, $NC^c$ or S, wherein $R^a$ and $R^b$ are independently selected from hydrogen, (1-2C)alkyl, hydroxy, amino, halo or mercapto, and $R^c$ is selected from hydrogen or a (1-6C)alkyl; or one of $X_1$ and $X_2$ is O and the other is $NR^2$.

2. The oligonucleotide according to claim 1, wherein the locked nucleoside is either directly attached to the 3' end of the triazole linker moiety or it is positioned 2, 3 or 4 nucleosides along from the 3' end of the triazole linker moiety.

3. The oligonucleotide according to claim 1, wherein the locked nucleoside is directly attached to the 3' end of the triazole linker moiety.

4. An oligonucleotide according to claim 1, further comprising an additional locked nucleoside is present in the portion of the oligonucleotide attached to the 5' end of the triazole linker moiety.

5. The oligonucleotide according to claim 4, wherein the additional locked nucleoside is either directly attached to the 5' end of the triazole linker moiety or is positioned 2, 3 or 4 nucleosides along from the 5' end of the triazole linker moiety.

6. The oligonucleotide according to claim 4, wherein the additional locked nucleoside is directly attached to the 5' end of the triazole linker moiety.

7. The oligonucleotide according to claim 1, wherein
R$^2$, R$^3$, R$^4$, R$^5$, R$^6$, R$^7$, R$^8$ and R$^9$ are each independently selected from hydrogen or (1-4C)alkyl;

V and Y are independently selected from O or NR$^x$, wherein R$^x$ is selected from hydrogen or (1-4C)alkyl;

m, n, r and s are integers independently selected from 0 to 2; and p and q are integers independently selected from 0 or 1;

with the proviso that the sum of integers m, n, p, q, r and s is either 0, 1, 2, 3, 4 or 5.

8. An oligonucleotide according to claim 1, wherein
R$^2$, R$^3$, R$^4$, R$^5$, R$^6$, R$^7$, R$^8$ and R$^9$ are hydrogen;

V and Y are O;

m, n, r and s are integers independently selected from 0 or 1; and p and q are integers independently selected from 0 or 1;

with the proviso that the sum of integers m, n, p, q, r and s is either 1, 2, 3, 4 or 5.

9. The oligonucleotide according to claim 1, wherein the triazole linker moiety -has the formula selected from any one of the following:

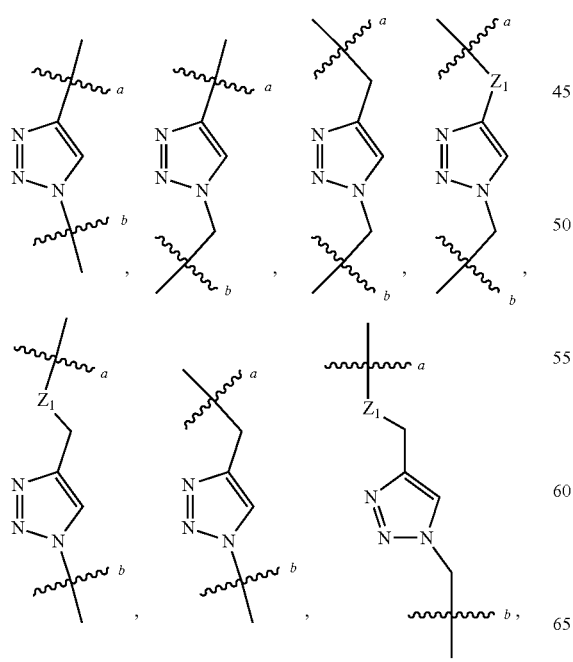

-continued

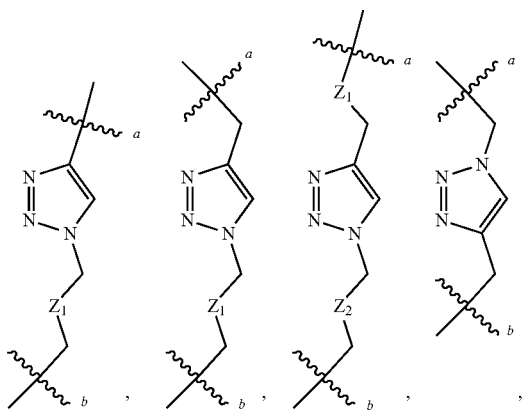

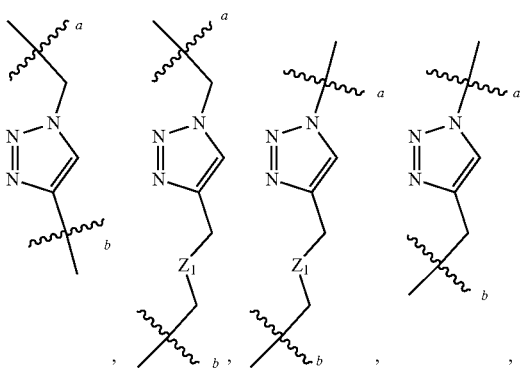

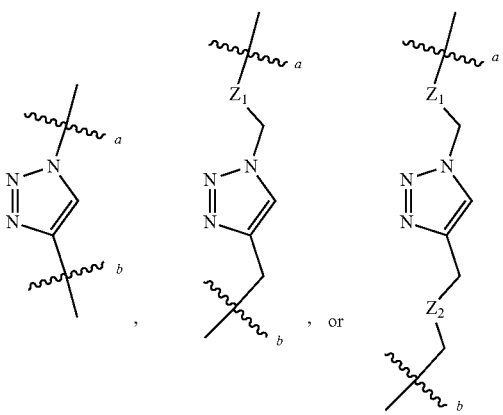

wherein:

Z$_1$ ands Z$_2$ are independently selected from O or NH;

z,31 denotes the 5' end of the linker moiety; and z,32 denotes the 3' end of linker moiety.

10. An oligonucleotide according to claim 1, wherein the linker moiety has the structural formula :

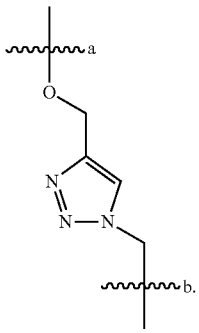

11. The oligonucleotide according to claim 1, wherein $Q_1$ is selected from $CH_2$, $CF_2$, O or S.

12. The oligonucleotide according to claim 1, wherein $Q_1$ is O.

13. The oligonucleotide according to claim 1, wherein one of $X_1$ and $X_2$ is selected from O, $NR^c$ or S and the other of $X_1$ and $X_2$ is $CH_2$, wherein $R^c$ is selected from hydrogen or a (1-6C)alkyl.

14. The oligonucleotide according to claim 1, wherein $X_1$ is $CH_2$ and $X_2$ is O.

15. An oligonucleotide comprising one or more dinucleotide moieties of the formula:

Formula (II)

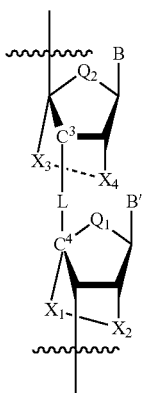

wherein:

$C^3$ is a 3' carbon;

$C^4$ is a 4' carbon;

$Q_1$ is selected from $CR^P R^q$, O, S or $NR^a$, wherein $R^P$ and $R^q$ are each independently selected from H, (1-4C)alkyl or halo and $R^a$ is selected from hydrogen or (1-4C)alkyl;

$Q_2$ is selected from $CR^P R^q$, O, S or $NR^a$, wherein $R^P$ and $R^q$ are each independently selected from H, (1-4C)alkyl or halo and $R^a$ is selected from hydrogen or (1-4C)alkyl;

B and B' are each independently: a nucleobase;

one of $X^1$ and $X^2$ is selected from $(CR^a R^b)_x$, wherein x is selected from 1 or 2 and the other is selected from $CR^a R^b$, O, $NR^c$ or S, wherein $R^a$ and $R^b$ are independently selected from hydrogen, (1-2C)alkyl, hydroxy, amino, halo or mercapto, and $R^C$ is selected from hydrogen or a (1-6C);

one of $X_3$ and $X_4$ is $(CR^d R^e)_y$, wherein y is selected from 1 or 2 and the other is $CR^d R^e$, O, $NR^f$ or S, wherein $R^d$ and $R^e$ are independently selected from hydrogen, (1-2C)alkyl, hydroxy, amino, halo or mercapto, and $R^f$ is selected from hydrogen or a (1-6C) alkyl; or one of $X_3$ and $X_4$ is O and the other is $NR^c$; or one of $X_3$ and $X_4$ is H and the other is selected from H, OH or $NH_2$;

and L is a linker moiety is a group of Formula A or Formula B shown below:

Formula A

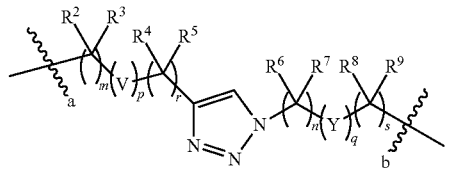

Formula B

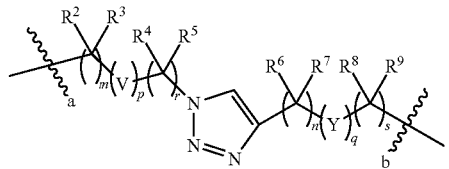

wherein:

<span style="font-family:monospace">⌇a</span> denotes the 5' end of the linker moiety;

<span style="font-family:monospace">⌇b</span> denotes the 3' end of linker moiety;

$R^2$, $R^3$, $R^4$, $R^5$, $R^6$, $R^7$, $R^8$ and $R^9$ are each independently selected from hydrogen or (1-4C)alkyl, wherein each (1-4C)alkyl is optionally substituted with one or more $NH_2$, OH or SH;

V and Y are independently selected from O, S or $NR^x$, wherein $R^x$ is selected from hydrogen or (1-4C)alkyl;

m, n, r and s are integers independently selected from 0, 1 or 2; and p and q are integers independently selected from 0 or 1;

with the proviso that the sum of integers m, n, p, q, r and s is either 0, 1, 2, 3, 4, 5 or 6.

16. An oligonucleotide according to claim 15, wherein $Q_2$ is selected from $CH_2$, $CF_2$, O or S.

17. An oligonucleotide according to claim 15, wherein $Q_2$ is O.

18. An oligonucleotide according to claim 15, wherein one of $X_3$ and $X_4$ is selected from O, $NR^f$ or S and the other of $X_1$ and $X_2$ is $CH_2$, wherein $R^f$ is selected from hydrogen or a (1-6C)alkyl.

19. An oligonucleotide according to claim 15, wherein one of $X_3$ and $X_4$ is O, and the other of $X_3$ and $X_4$ is $CH_2$.

20. An oligonucleotide according to claim 15, wherein $X_3$ is $CH_2$ and $X_4$ is O.

21. An oligonucleotide according claim 15, wherein the dinucleotide moiety has one of the structural formulae shown below:

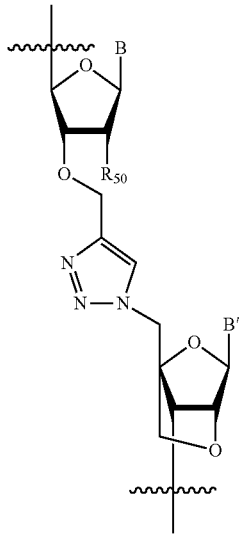

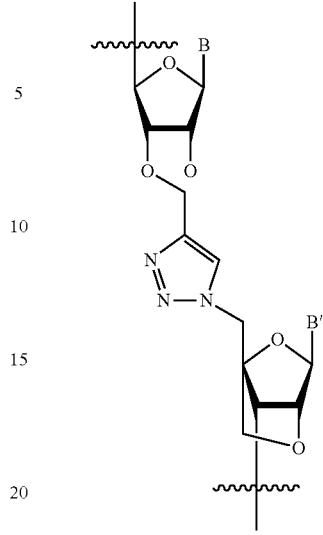

wherein B and B' are each independently a nucleobase and $R_{50}$ is H, OH, $OCH_3$ or F.

22. A method of amplifying a polynucleotide sequence in a polymerase chain reaction (PCR); wherein an oligonucleotide according to claim 1 is a template for amplifying a polynucleotide sequence in a polymerase chain reaction (PCR).

* * * * *